(12) United States Patent
Toshima et al.

(10) Patent No.: US 7,287,853 B2
(45) Date of Patent: Oct. 30, 2007

(54) SPECTACLE AND CONTACT LENS SELECTING SYSTEM AND METHOD THEREOF

(75) Inventors: Akio Toshima, Akashi (JP); Takehiko Yoshida, Higashiosaka (JP)

(73) Assignee: Vision Optic Co., Ltd., Osaka (JP)

( * ) Notice: Subject to any disclaimer, the term of this patent is extended or adjusted under 35 U.S.C. 154(b) by 509 days.

(21) Appl. No.: 10/500,658

(22) PCT Filed: Jan. 6, 2003

(86) PCT No.: PCT/JP03/00003

§ 371 (c)(1),
(2), (4) Date: Jul. 2, 2004

(87) PCT Pub. No.: WO03/057038

PCT Pub. Date: Jul. 17, 2003

(65) Prior Publication Data

US 2005/0073648 A1    Apr. 7, 2005

(30) Foreign Application Priority Data

Jan. 4, 2002    (JP) .............................. 2002-000200

(51) Int. Cl.
*A61B 3/10* (2006.01)
(52) U.S. Cl. ...................................... 351/205; 351/206
(58) Field of Classification Search ................ 351/205, 351/206, 209, 245; 340/575, 945; 600/558
See application file for complete search history.

(56) References Cited

FOREIGN PATENT DOCUMENTS

| JP | 2000-107129 | 4/2000 |
| JP | 2000-122011 | 4/2000 |
| JP | 2001-350982 | 12/2001 |

*Primary Examiner*—Timothy Thompson
(74) *Attorney, Agent, or Firm*—Keating & Bennett, LLP

(57) ABSTRACT

A spectacle and contact lens selecting system includes an input unit for inputting information related to a state of eyes of a user, an eyeball optical model deciding unit for deciding an eyeball optical model corresponding to the information related to the state of the eyes input by the input unit, an eyeball accommodation range determination unit for examining optical performance of an eyeball within a range of accommodation of the user in the decided eyeball optical model to determine the range of accommodation of the eyeball, a lens power selecting unit for examining optical performance when the user wears spectacles or contact lenses to select a lens power, and a wearing state display unit for displaying a wearing state of the spectacles or the contact lenses to be selected.

12 Claims, 60 Drawing Sheets

Fig. 9

LENS SELECTION CRITERION DATABASE

| NAME |
|---|
| CUSTOMER CODE |
| AGE |
| LENS POWER |
| LENS FUNCTION: THICKNESS / WEIGHT / ENDURANCE / UV-PROTECTION |
| COLORS |
| BUDGET |
| INTENDED USE |

Fig. 10

LENS DATABASE

| MANUFACTURER'S NAME |
|---|
| MODELS |
| PURPOSE OF USE |
| LENS FUNCTION: THICKNESS / WEIGHT / ENDURANCE / UV-PROTECTION |
| COLORS |
| PRICES |
| LENS POWER |

Screen at the top of site

Personal computer screen
information collecting screen

PD measurement screen

Measure the position of your
pupil at the center of lens

PD measurement system

Facial image selection screen

On which face do you want to try spectacles?

○ Use model face

Male  Female

○ Use my self-portrait

Self-portrait upload screen

Which is your picture data?

1. Use digital camera picuture data
GO→

2. Use picture data obtained
by scanner
GO→

Upload facial portrait in accordance of help navigation

Use digital camera picture<help navigation

>
1.
2.
3.
4.

Store

Saved-item confirmation screen

Purchased frame confirmation screen

Fig. 22

Lens power selecting screen for getting spectacles

Which lens power data do you use
for the spectacles on this order?

○ Use lens power data tested on this site

○ Use lens without vision correction

○ Use prescription data from ophthalmologist
or data of card form spectacle store

Fig. 23

Prescription data entry screen

Enter lens power

- PD [ mm ]

- Right eye [ S ▼ ] [ C ▼ ] [ AX ▼ ]

- Left eye [ S ▼ ] [ C ▼ ] [ AX ▼ ]

- Pull-down display on lens power data
  ...
  +0.25
  −0.25
  −0.50
  −0.75
  −1.00
  ...

- Pull-down display on astigmatic axis data
  180°±22.5°
  135±22.5°
  90±22.5°
  45±22.5°
  0±22.5°

Fig. 24
Lens thickness comparison
Which lens do you want for your spectacles?
Itemization of purchase
XYZ 5550
Price for complete set of spectacles
5,000 YEN
Colored lens
Pink 40% 
Price for colored lens
+2,000 YEN
Total 7,000 YEN
Thickness are displayed in accordance with your lens power.
| Standard lens | Thin lens | Thin lens without distortion |
|---|---|---|
| 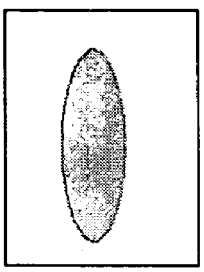 | 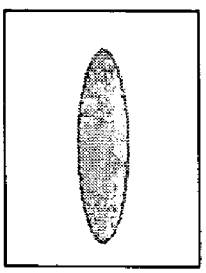 | 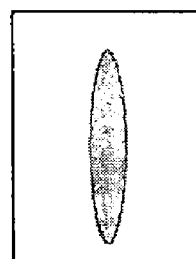 |
| Lens price +0 YEN | Lens price +3,000 YEN | Lens price +5,000 YEN |

Fig. 26

USER INFORMATION DATABASE

| NAME |
|---|
| DATE OF BIRTH |
| ADDRESS |
| PHONE NUMBER |
| CONDITION OF EYES |
| REQUEST CONCERNING SPECTACLES |
| USER INFORMATION IDENTIFICATION (ID) |
| USER PASSWORD |
| USER CODE |
| FACSIMILE NUMBER |
| E-MAIL ADDRESS |
| URL |
| COMPUTER ENVIRONMENTS |

Fig. 27

DATA INPUT FROM FRAME SELECTION INFORMATION INPUT MEANS

| | | |
|---|---|---|
| SELECTION CRITERIA (IN TEXT DATA) | FASHION | |
| | BUDGET | |
| | FUNCTION | |
| | FITNESS TO THE FACE | |
| FUNCTION 1 (FRONT VIEW OF FACE IMAGE) | 1. DISTANCE BETWEEN RIGHT AND LEFT PUPILS | |
| | 2. WIDTHS FROM CENTER OF RIGHT AND LEFT PUPILS TO FEET OF EARS | |
| | 3. OPENING ANGLES OF TEMPLES DETERMINED BASED ON 2 | |
| FUNCTION 2 (SIDE VIEW OF FACE IMAGE) | 1. DISTANCE FROM FEET OF EARS TO TOPS OF CORNEAS | |
| | 2. BENDING POSITIONS OF TEMPLES | |
| | 3. DISTANCES BETWEEN TOPS OF CORNEAS AND FOOT OF NOSE | |
| | 4. OPENING ANGLES OF PAD BRIDGES DETERMINED BASED ON 3 | |

FIG. 28

FRAME FUNCTIONAL STRUCTURE DATABASE

| SIZE | ACTUAL SIZE (44φ ~62φ) | |
|---|---|---|
| FEATURE | SHAPE-MEMORY ALLOY | |
| | SUPER-LIGHT WEIGHT | |
| | SUPER-ELASTICITY | |
| | SIMULTANEOUS FUNCTION AS SUNGLASSES | |
| | PORTABILITY | |
| | OTHERS | |
| FUNCTION 1 (FRONT VIEW OF FACE IMAGE) | 1. DISTANCE BETWEEN RIGHT AND LEFT PUPILS | |
| | 2. WIDTHS FROM CENTER OF RIGHT AND LEFT PUPILS TO FEET OF EARS | |
| | 3. OPENING ANGLES OF TEMPLES DETERMINED BASED ON 2 | |
| FUNCTION 2 (SIDE VIEW OF FACE IMAGE) | 1. DISTANCE FROM FEET OF EARS TO TOPS OF CORNEAS | |
| | 2. BENDING POSITIONS OF TEMPLES | |
| | 3. DISTANCES BETWEEN TOPS OF CORNEAS AND FOOT OF NOSE | |
| | 4. OPENING ANGLES OF PAD BRIDGES DETERMINED BASED ON 3 | |

Fig. 29

FRAME DECORATIVE STRUCTURE DATABASE

| | |
|---|---|
| | WELLINGTON |
| | LLOYD |
| | OVAL |
| | SQUARE |
| SHAPE | TONNEAU |
| | BOSTON |
| | BUTTERFLY |
| | AUTO (DROP) |
| | RIMLESS (TWO-POINT, THREE-POINT) |
| | METAL + NYLON RIMMED |
| | CELLULOID + NYLON RIMMED |
| MATERIAL | METAL |
| | CELLULOID |
| | BROW LINE |
| | COMBINATION |
| | OTHERS |
| BRAND | VARIOUS BRANDS |
| COLOR | VARIOUS COLORS |

Fig. 36

Personal computer screen
information collecting screen

Give us information of your personal computer: needed to get spectacles fitted to your eyes Resolution
○ 600×800    ○ *X*
○ *X*

How long is this line on your monitor screen in centimeters?

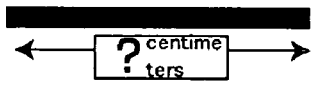

Fig. 37

Entry of personal information and wearing conditions

These items are important information for deciding optimal lens power. Enter correctly.

Name  [               ]

Sex   ○ male   ○ female

Date of Birth  [    ] year [    ] month [    ] day

Height  [    ] cm

Fig. 38

> Entry of personal information and wearing conditions
>
> These items are important information for deciding optimal lens power. Enter correctly.
>
> In which situation do you mainly use?
> - ○ Reading
> - ○ Deskwork
> - ○ Personal comput    er
> - ○ Driving
>
> What is your profession?
> - ○ Office work
> - ○ Sales
> - ○ Domestic help
> - ○ Student
> - ○ Others  [          ]

Fig. 39

> Lens power check (right eye)
>
> Follow the following instructions. The right eye is tested. First, four zones hatched with parallel lines are displayed. Move 1 m or more away from the screen and then come up to the position where you can clearly see the lines of any one of the four zones. Remove the spectacles and contact lenses at this step. When watching the displayed target, cover your left eye with a hand so as not to touch the eye.

Fig. 47
Fig. 48
Example where target appears as three lines
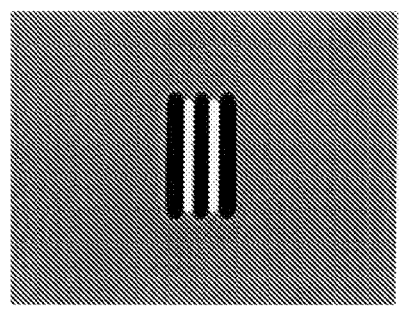
Example where target does not appear as three lines
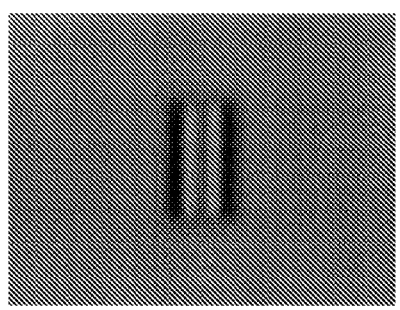

Measurement of near point distance

First, come close as much as possible. Then, move away to the position where you can clearly see three lines. Measure the distance from the screen and the eye and input it in centimeters.

Measurement of near point distance

First, come close as much as possible. Then, move away to the position where you can clearly see three lines. Measure the distance from the screen and the eye and input it in centimeters.

Fig. 63

STEP 1 Entry of personal information and wearing conditions.

These items are important information to be used for determining the optimal lens power. Enter them correctly.

STEP1

Name

Sex

○ Male ○ Female

Birthday

[2001] Year [12] Month [31] Day

Height

[    ] cm

◁◁ Return          Next ▷▷

Fig. 68

| | | | | | |
|---|---|---|---|---|---|
| ∎ | ∎ | Ⅲ | Ⅲ | Ⅲ | No zone provides the viewing of three lines. |
| 1 | 2 | 3 | 4 | 5 | |
| Ⅲ | Ⅲ | Ⅲ | Ⅲ | Ⅲ | |
| 10 | 9 | 8 | 7 | 6 | |

Measurement of far point vision

Click on the zone that provides the viewing of three lines. If no zone provides the viewing of three lines, click on the "No zone provides the viewing of three lines."

Measurement of near point distance

First, come as close to the screen as possible, and then go away to where you can clearly see the three lines. Measure the distance between the screen and your eye with a scale and then input the distance in cm.

Fig. 76
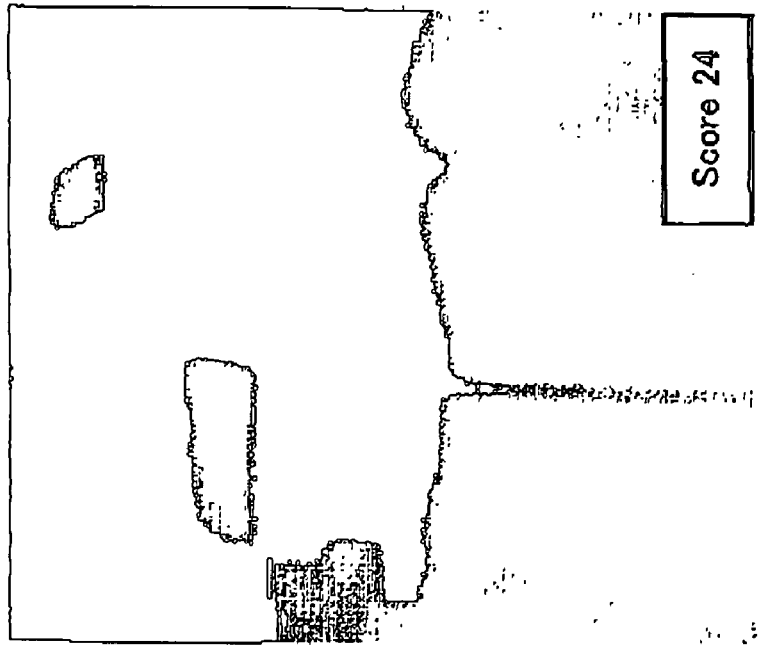
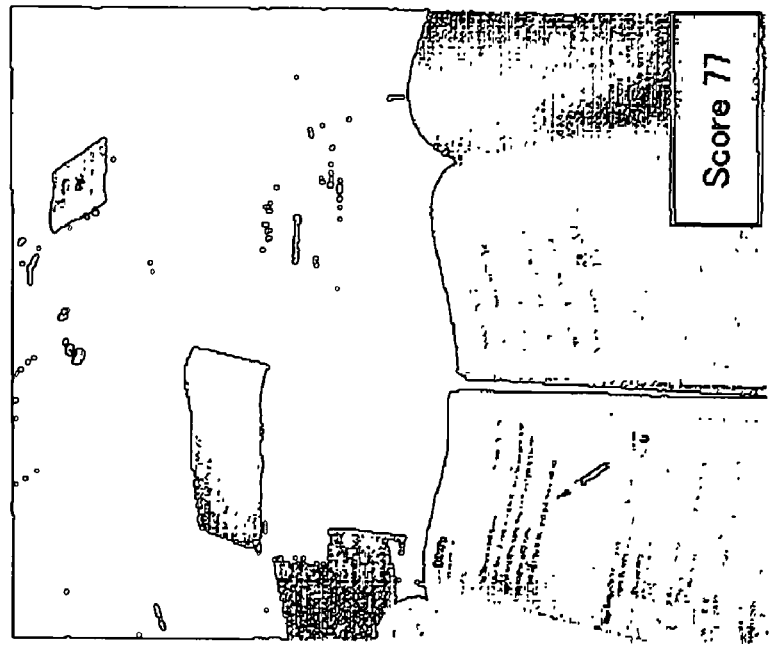

Fig. 77

⟨Presentation of the way of viewing before and after correction⟩

| | 0.3 m | 0.5~0.6 m | 5 m |
|---|---|---|---|
| Right eye | | | |
| Uncorrected eye | Score ○ | Score ○ | Score ○ |
| Corrected eye with lens −3.0D | Score ○ | Score ○ | Score ○ |

The way of viewing is indicated in a total of six images, with 3 steps of distances in the horizontal direction and 2 steps of uncorrected and corrected eyes in the vertical direction.
This method of representation can display the difference between two lenses with lens 1 and lens 2 represented on the vertical direction.

SPECTACLE AND CONTACT LENS SELECTING SYSTEM AND METHOD THEREOF

BACKGROUND OF THE INVENTION

1. Field of the Invention

The present invention relates to a spectacle and contact lens selecting system and a method thereof, and in particular, to a spectacle and contact lens selecting system and a method thereof, which enable the selection of spectacles and contact lenses fitted to each person on a computer network.

2. Description of the Related Art

Conventionally known methods for selecting spectacles lenses are methods which utilize eyeball models. Well known eyeball models are the Gullstrand eyeball model and the Le-Grand eyeball model.

These eyeball models have been used entirely for the design and evaluation of spectacles lenses. For the design of spectacles lenses, one standard model prepared as an optical eye model would make it possible to design lenses having various powers for standard eyes. This is sufficient for the design irrespective of the eye structure of a person because he/she can select among spectacles lenses prepared in every power of 0.25 D by actually wearing them, thereby ensuring that he/she finds spectacles lenses suitable for correction. That is, selection is flexible.

Currently, on the other hand, to measure uncorrected or corrected vision, one goes to see an ophthalmologist or has his/her vision measured at spectacles shops using optometers.

Recently, for example, virtual malls are available over networks such as the Internet. However, none of the spectacles shops available in these virtual malls provides a system for measuring the uncorrected and corrected vision on an on-line basis.

However, to solely determine the power of spectacles lenses suitable for the eyes of an individual, an optical model such as the eyeball model assumed to be commonly applicable to everyone would cause significant error in optical calculation thereby making the determination impossible. The determination can be made only by constructing an eyeball model for each person.

Use of the conventional eyeball models will create the following problems.

Since the conventional eyeball model is based on measurements made on eyes of people from Europe and the United States, they cannot be used for constructing a model having values close to those obtained by measuring living eyes of other races, e.g., Japanese people. For example, Japanese have a smaller radius of curvature of the cornea than do people from Europe and the United States.

A model is prepared based on an average of measurements. Literature shows that in such data, the depth of the anterior chamber of the eye varies with age or the length of the eye axis is correlated with the degree of myopia for low degrees of shortsightedness. Thus, it is necessary to construct an eyeball model according to the age and the degree of myopia of each individual.

Although the lens of the eye has a refractive index that is unevenly distributed, the average refractive index is used. The simplified double structure provided to the lens of the eye causes a significant error in tracking rays of light.

On the other hand, where difficulty is found in visiting medical care providers or spectacles shops such as due to the time required and the distance traveled for the visit, there has been a need for implementing a system which enables one to remotely measure his/her vision over the Internet.

In particular, a person's current spectacles or contact lenses may no longer properly correct their vision. In this case, it would be very convenient to remotely measure his/her uncorrected and corrected vision in order to determine whether he/she needs to buy new spectacles or contact lenses.

Moreover, if a user can see himself/herself wearing spectacles or contact lenses when selecting spectacles or contact lenses, the selection of spectacles or contact lenses is facilitated.

SUMMARY OF THE INVENTION

To overcome the problems described above, preferred embodiments of the present invention provide a system and method for determining a spectacles/contact lens power suitable for an individual, and for confirming wearing condition.

A spectacle and contact lens selecting system according to a preferred embodiment of the present invention includes an input unit for inputting information related to the condition of the eyes of a user, an eyeball optical model deciding unit for deciding an eyeball optical model corresponding to the information related to the condition of the eyes input by the input unit, an eyeball accommodation range determination unit for examining optical performance of an eyeball within a range of accommodation of the user in the eyeball optical model decided by the eyeball optical model deciding unit to determine the range of accommodation of the eyeball, a lens power selecting unit for examining optical performance when the user wears spectacles or contact lenses to select a lens power, and a wearing state display unit for generating and displaying a wearing state of the spectacles or the contact lenses to be selected.

In the spectacle and contact lens selecting system, the input unit is preferably configured so as to allow the user to input information about the eyes of the user, such as a wearing condition of the user, an age, a near point distance, a far point distance, or a vision at a constant distance.

In the spectacle and contact lens selecting system, the eyeball optical model deciding unit preferably includes a start eyeball optical model deciding unit for deciding a start eyeball optical model based on the information about the eyes of the user, such as an age and an approximated lens power.

In the spectacle and contact lens selecting system set, the eyeball optical model deciding is preferably configured such that at least one of a focal state in the eyeball of the user at an accommodation midpoint calculated from a near point distance and a far point distance of the user and a focal state in the eyeball of the user in a non-accommodative state calculated from the far point distance of the user is optimized.

The spectacle and contact lens selecting system preferably further includes an eyeball optical model validity examination unit for examining the validity of the eyeball optical model at a limit of accommodation on at least one of a near point side and a far point side.

In the spectacle and contact lens selecting system, the eyeball accommodation range determination unit is preferably configured to determine a range of accommodation of optical dimensions of the eyeball at an accommodation midpoint.

The spectacle and contact lens selecting system preferably further includes an eyeball optical model image generating unit for generating and displaying an image of an eyeball optical model in which the range of accommodation of the eyeball is determined.

The spectacle and contact lens selecting system preferably further includes an eyeball optical model focal performance examination unit for examining focal performance of the eyeball optical model at a near point or a position within a range of accommodation ability in the vicinity of the near point, at a far point or a position within the range of accommodation ability in the vicinity of the far point, or at a position away from the near point and the far point in a naked eye state of the user.

In the spectacle and contact lens selecting system, the eyeball optical model focal performance examination unit preferably includes a unit for examining a focal state of the eyeball optical model of the user at the near point or the position within the range of accommodation ability in the vicinity of the near point, at the far point or the position within the range of accommodation ability in the vicinity of the far point, or the position away from the near point and the far point after vision correction with the spectacles or the contact lenses.

The spectacle and contact lens selecting system preferably further includes a sharpness score generating unit for generating a visibility sharpness score of the user at least one of before and after vision correction with the spectacles or the contact lenses.

The spectacle and contact lens selecting system preferably further includes a viewed image generating unit for generating an image to be viewed by the user at least one of before and after vision correction with the spectacles or the contact lenses.

In the spectacle and contact lens selecting system set, the wearing state display unit preferably includes an image acquisition unit for acquiring an image of the user, and an image synthesizing unit for synthesizing an image of spectacles or contact lenses to be selected and the acquired image of the user.

A spectacle and contact lens selecting method according to another preferred embodiment of the present invention includes the steps of inputting information related to a state of eyes of a user, deciding an eyeball optical model corresponding to the information related to the state of the eyes input by the input step, examining optical performance of an eyeball within a range of accommodation of the user in the eyeball optical model decided by the step of deciding the eyeball optical model, to determine the range of accommodation of the eyeball, examining optical performance when the user wears spectacles or contact lenses to select a lens power, and generating and displaying a wearing state of the spectacles or the contact lenses to be selected.

In the spectacle and contact lens selecting method, the input step preferably includes the step of inputting information about the eyes of the user, such as a wearing condition of the user, an age, a near point distance, a far point distance, or a vision at a constant distance.

In the spectacle and contact lens selecting method, the step of deciding the eyeball optical model preferably includes the step of deciding a start eyeball optical model based on the information of the eyes of the user, such as an age and an approximated lens power.

In the spectacle and contact lens selecting method, the step of deciding the eyeball optical model preferably includes the step of deciding the eyeball optical model such that at least one of a focal state in the eyeball of the user at an accommodation midpoint calculated from a near point distance and a far point distance of the user and a focal state in the eyeball of the user in a non-accommodative state calculated from the far point distance of the user is optimized.

The spectacle and contact lens selecting method preferably further includes the step of examining validity of the eyeball optical model at a limit of accommodation on at least one of a near point side and a far point side.

In the spectacle and contact lens selecting method, the step of determining the range of accommodation of the eyeball preferably includes the step of determining a range of accommodation of optical dimensions of the eyeball at an accommodation midpoint.

The spectacle and contact lens selecting method set preferably further includes the step of generating and displaying an image of an eyeball optical model in which the range of accommodation of the eyeball is determined.

The spectacle and contact lens selecting method preferably further includes the step of examining focal performance of the eyeball optical model at a near point or a position within a range of accommodation ability in the vicinity of the near point, at a far point or a position within the range of accommodation ability in the vicinity the far point, or at a position away from the near point and the far point in a naked eye state of the user.

In the spectacle and contact lens selecting method, the step of examining the focal performance of the eyeball optical model preferably includes the step of examining a focal state of the eyeball optical model of the user at the near point or the position within the range of accommodation ability in the vicinity of the near point, at the far point or the position within the range of accommodation ability in the vicinity of the far point, or at the position away from the near point and the far point after vision correction with the spectacles or the contact lenses.

The spectacle and contact lens selecting method preferably further includes the step of generating a visibility sharpness score of the user at least one of before and after vision correction with the spectacles or the contact lenses.

The spectacle and contact lens selecting method preferably further includes the step of generating an image to be viewed by the user at least one of before and after vision correction with the spectacles or the contact lenses.

In the spectacle and contact lens selecting method, the step of generating and displaying the wearing state preferably includes the step of acquiring an image of the user, and the step of synthesizing an image of spectacles or contact lenses to be selected and the acquired image of the user.

The above and other elements, steps, characteristics, features and advantages of the present invention will be apparent from the following detailed description of preferred embodiments of the present invention with reference to the accompanying drawings.

BRIEF DESCRIPTION OF THE DRAWINGS

FIG. 9 is a view showing a lens selection criterion database;

FIG. 10 is a view showing a lens database;

FIG. 22 is a schematic view of a lens power selection screen for having spectacles made;

FIG. 23 is a schematic view of a prescription data entry screen;

FIG. 24 is a schematic view of a lens thickness comparison screen;

FIG. 26 is a view showing an example of a database related to user information;

FIG. 27 is a view showing an example of data input by frame selection information input unit;

FIG. 28 is a view showing an example of a database structure related to a functional structure of a frame;

FIG. 29 is a view showing an example of a database structure related to a decorative structure of a frame;

FIG. 36 is a schematic view of a personal computer screen information collecting screen;

FIG. 37 is a schematic view of a user information entry screen;

FIG. 38 is a schematic view of a wearing condition entry screen;

FIG. 39 is a schematic view of a guidance screen displayed at an astigmatism axis measurement step 1;

FIG. 47 is a view showing a state of the user at a far point distance measurement step 5;

FIG. 48 is a view showing an example how the far point distance measurement target is viewed at a far point distance measurement step 5-1;

FIG. 63 is a view showing an example of display of a personal information entry screen;

FIG. 68 is a view showing an example of display of a far point vision test screen;

FIG. 76 is a view showing a example of a relation between a sharpness score and a view; and FIG. 77 is a view showing a example of a screen for confirming an image viewed before and after vision correction.

DETAILED DESCRIPTION OF PREFERRED EMBODIMENTS

Figure 1:
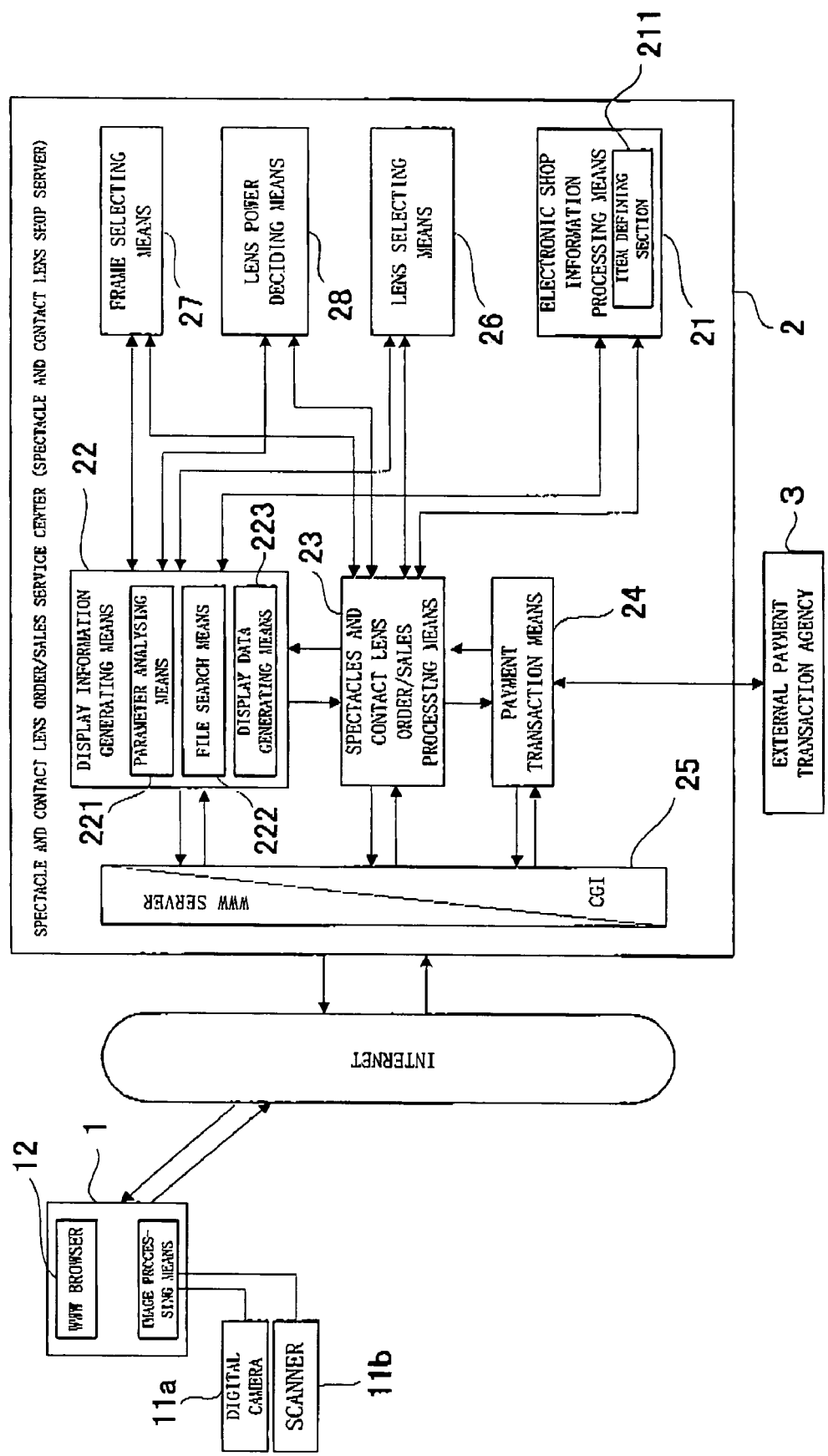
FIG. 1 is a diagram showing an example of a system configuration of a spectacle and contact lens selecting system according to a preferred embodiment of the present invention.

FIG. 1 is a view showing an example of a system configuration of a spectacle and contact lens selecting system according to a preferred embodiment of the present invention. In FIG. 1, the reference numeral 1 denotes a user client, the reference numeral 2 denotes a spectacle order/sales service center, and the reference numeral 3 denotes an external payment transaction agency. They are physically connected to each other via a network. In the following description, the network connecting the user client 1, the spectacle order/sales service center 2, and the external payment transaction agency 3 is preferably the Internet.

The user client 1 is a terminal used when a purchaser of spectacles makes an order for sales through the network, for example, a personal computer having a network connection. The user client 1 is an input/output device serving as an interface with the user who uses it. Although a general keyboard or mouse is used as the input device for inputting information, a dedicated input device such as a pointing device, such as a track ball or a joystick, a touch panel, and a switch may be provided. As an image display device, a general CRT display or a liquid crystal monitor is preferably used. Furthermore, this user client 2001 includes an image input device for acquiring prescription data as image information. Although a digital camera 11a and a scanner 11b are preferably used as the image input device, any devices capable of digitizing and inputting image information, such as a video camera or a television camera may be used. The user client 1 also includes a WWW browser 12 as an interface for providing access to the spectacle order/sales service center 2.

The spectacle order/sales service center 2 is a server for providing the user client 1 who is connected through the Internet with a service to sell spectacles fitted to their vision or in accordance with requests of each user to order. The spectacle order/sales service center 2 includes information processing equipment, such as a personal computer or a work station having a network connection function, and is connected to the user client 1 through the Internet. The spectacle order/sales service center 2 includes an electronic shop information processing unit 21, a display information generating unit 22, a spectacle order/sales processing unit 23, a payment transaction unit 24, a WWW server/CGI 25, a lens selecting unit 26, a frame selecting unit 27, and a lens power deciding unit 28.

The electronic shop information processing unit 21 defines item data, such as spectacle lenses and frames sold by the spectacle order/sales service center 2 using an item defining section 211 through the input/output device. The item data defined herein is stored in an item database as item data information.

In this preferred embodiment, the item data information includes text data, such as a name of a shelf on which items such as frames are displayed, an item number of a spectacle lens or frame, an item name, a price, the description of an item, and item management information, image data of an item, such as a frame and other useful information. The spectacle order/sales service center 2 also includes an input/output device serving as an interface with a creator of an electronic catalog. The input/output device receives the input of the item information, such as text data such as a shelf name, an item category and a price that are necessary for defining an item or image data indicating a shape of an item from the catalog creator. Moreover, this input/output device outputs information including item information, such as an item number and the number of items, delivery destination information of an item, payment information such an external payment transaction agency name, a payment date, and the sum as order information of an item purchased by the user.

An electronic shop opening information database including a shop database, an item database, and a basket database is provided for the electronic shop information processing unit 21. The shop database stores information for opening an electronic shop and information for defining a shop layout to display the item information. The item database stores the defined item data information. The basket database is for accumulating information of an item selected by the user client 1 to be purchased. The electronic shop information processing unit 21 performs a function of storing the transferred item data information in the item database.

The display information generating unit 22 generates display information, such as the electronic catalog in response to a request from the user client 1. The display information generating unit 22 includes a parameter analyzing unit 221, a file search unit 222, and a display data generating unit 223. The parameter analyzing unit 221 analyzes vision test data and frame selection information received from the user client 1 through the WWW server/CGI 25 so as to extract a parameter included in the vision test data and frame selection information. The file search unit 222 searches each database registered and stored by the electronic shop information processing unit 21 based on the parameter extracted by the parameter analyzing unit 221. The display data generating unit 223 generates display data that is displayed as a WWW page based on the data searched by the file search unit 222. More specifically, the display data generating unit 223 functions as a WWW page generator.

The spectacle order/sales processing unit 23 receives a customer ID and an ID of an item to be purchased from the display information generating unit 22 when the item to be purchased (a spectacle lens, a frame or the like) is selected by the user client 1 so as to acquire detailed information of the item to be purchased from the item database based on this information. Then, it stores information of the item in a customer basket database for a target customer in the basket database. Thereafter, a list of items to be purchased by the target customer is acquired from the basket database so as to be transmitted to the display information generating unit 22.

The payment transaction unit 24 receives the customer ID from the display information generating unit 22 when the item is selected to be purchased by the user client 1 so as to retrieve item data information corresponding to the user from the basket database. Then, it requests the external payment transaction agency 3 to transact the payment based on the retrieved item data information. The payment transaction unit 24 is notified of completion of the payment transaction by the external payment transaction agency 3 so as to inform the spectacle order/sales processing unit 23 and the electronic shop information processing unit 21 of completion of the order process. At the same time, it creates itemization data for informing the user client 1 of a purchasing process so as to deliver the data to the display information generating unit 22.

The WWW server/CGI 25 acts as an interface with the user client 1 so as to receive display request information from the user client 1 and to transfer display data to the user client 1.

The frame selecting unit 27 selects a frame selected by the user from the frames displayed in a virtual store. In this case, a frame selecting process described in a spectacle virtual try-on system described below is executed such that the user can select a frame while watching an image of the user wearing a potentially purchased frame.

The lens power deciding unit 28 remotely tests the vision of the user to determine the power of a corrective lens. In this case, a vision test using an eyeball optical model for a remote subjective vision test system described below is executed so as to accurately determine the power of a corrective lens.

The lens selecting unit 26 selects a lens fitted to the user in consideration of the results of the vision test, a budget, and the functions of a lens.

The external payment transaction agency 3 provides a payment service for the ordered spectacles for the spectacle order/sales service center 2 based on a request sent from the payment transaction unit 24 of the spectacle order/sales service center 2.

Next, the schematic operations of the user client 1 and the spectacle order/sales service center 2 will be described.

In the spectacle order/sales service center 2, the WWW server/CGI 25 receives spectacle order page information sent from the user client 1 so as to activate the display information generating unit 22.

Upon activation, the display information generating unit 22 receives the spectacle order page information from the WWW server/CGI 25 such that the parameter analyzing unit 221 analyzes the received spectacle order page information. The parameter analyzing unit 221 outputs information, such as a shop ID for specifying an electronic shop to be displayed, a catalog template for specifying the type of a background screen of an electronic catalog, an item ID of an item to be displayed, and a customer ID for identifying a user as the results of analysis. Based on these data output from the parameter analyzing unit 221, the file search unit 222 searches in the shop database, the item database, and the basket database so as to acquire data required to create a display screen requested by the user client 1.

After acquisition of the data by the file search unit 222, the process proceeds to the display data generating unit 223. The display data generating unit 223 first determines the type of the request from the user client 1. If the request from the user client 1 is other than "selection of an item to be purchased" or "purchase of an item," the display data generating unit 223 uses the results of a search to create data for display by the file search unit 223.

As a result of determination at the step of determining the type of the request from the user client 1, if the type of the request from the user client 1 is "determination of an item to be purchased," that is, if the customer instructs to "add a selected item into the shopping basket" so as to indicate that the displayed item will be purchased, the display data generating unit 223 activates the spectacle order/sales processing unit 23.

Upon activation, the spectacle order/sales processing unit 23 receives the customer ID and the item ID of the item selected to be purchased by the customer from the display data generating unit 223. Then, it acquires detailed item data information for the corresponding item from the item database using the item ID as key information. Then, the item data information acquired at the above-described step is stored in the customer basket database of the customer identified by the customer ID received from the display data generating unit 223 in the basket database. At this time, if the corresponding customer basket database does not exist, a customer basket database corresponding to the customer ID is created so as to store the item data information therein. Furthermore, it retrieves all of the item data information selected by the user from the customer basket database so as to deliver it to the display data generating unit 223. In this case, the display data generating unit 223 creates a list of display information of items to be purchased by the customer from the item data information received from the spectacle order/sales processing unit 23 so as to send it to the user client 1. At this time, the customer can confirm the items to be purchased or cancel a part or all of the items to be purchased based on the information displayed.

As a result of the determination at the step of determining the type of the request from the user client 1, if the type of the request from the user client 1 is "purchase of an item," that is, if the customer makes the decision to purchase the items selected, the display data generating unit 223 activates the payment transaction unit 24 prior to creation of display data.

Upon activation, the payment transaction unit 24 receives the customer ID from the display data generating unit 223. The payment transaction unit 24 searches the item data information of the items to be purchased, which is stored in the customer basket database of the customer identified by the customer ID from the basket database. Based on the item data information obtained as a result of the search, the external payment transaction agency 3 is requested to make a payment transaction. In response to this request, the external payment transaction agency 3 provides a payment transaction service in place of the spectacle order/sales service center 2 and then notifies the spectacle order/sales service center 2 of completion of the payment transaction at its completion. Since the payment transaction carried out by the external payment transaction agency 3 is not substantially different from a conventional one, the detailed description thereof is omitted herein.

When the payment transaction unit 24 is notified of the completion of the payment transaction from the external payment transaction agency 3, it transfers order information including information related to the ordered item, such as an item number and the number of ordered items, delivery destination information indicating destination of the item, and payment information including a name of the external payment transaction agency 3 executing the payment transaction, a payment date, and sum information to the spectacle order/sales service center 2. In the spectacle sales service center 2, the order information received from the WWW server/CGI is displayed by the input/output device. Finally, the payment transaction unit 24 creates itemization data for notification of the completion of the payment transaction and transmits it to the display data generating unit 223. The display data generating unit 223 uses the received itemization data to create a display screen for notification of the completion of the payment transaction and transfer it to the user client 1.

Next, a method of ordering and selling spectacles by the spectacle and contact lens selecting system will be described below.

Figure 2:
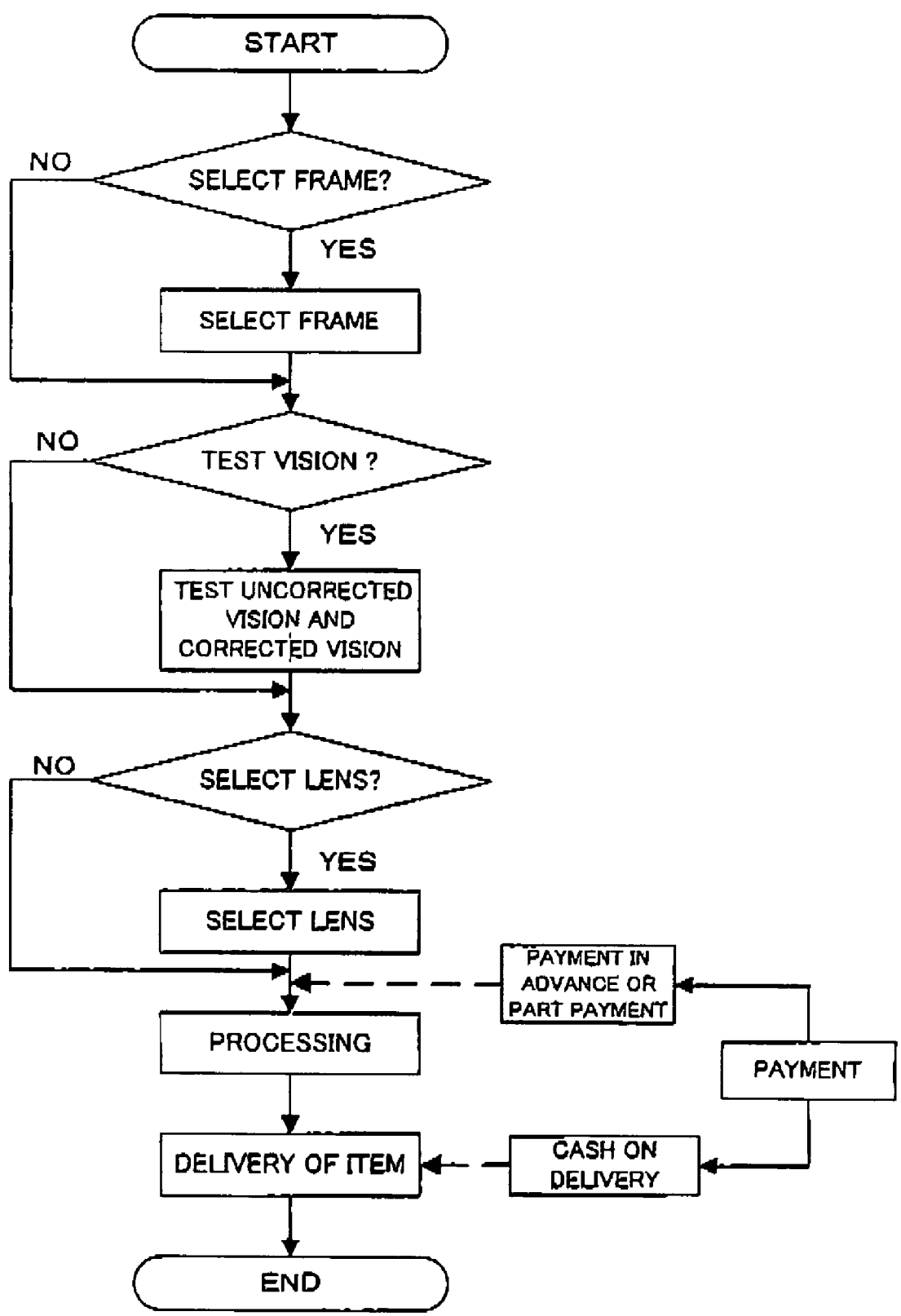
FIG. 2 is a diagram showing a process when a user purchases spectacles or contact lenses.

FIG. 2 is a view showing a process in which the user purchases spectacles or contact lenses. As illustrated, if the user wants to select a frame, a frame is selected, if the user wants to test his/her vision, an uncorrected vision and a corrected vision are tested. If the user wants to select a lens, a lens is selected. In response to notification of payment in advance or part payment from the payment transaction, spectacles or contact lenses are processed or assembled based on the information of the selected frame and the selected lenses and the result of the vision test. Then, the item is delivered to the user cash on delivery. Although the process is herein described as proceeding in the order of the selection of a frame, the vision test, and the selection of a lens, it is sufficient to carry out only the processes required by the request of the user and the order thereof may be arbitrary. For example, vision may be tested first. Then, a lens may be selected, and a frame may be selected at the final step. If the user only wants to change a lens power, only a vision test may be performed such that a lens or a frame can be selected based on the customer database. If the user only wants to replace a frame, only a frame may be selected such that vision may be determined or a lens may be selected based on the customer database.

Figure 3:
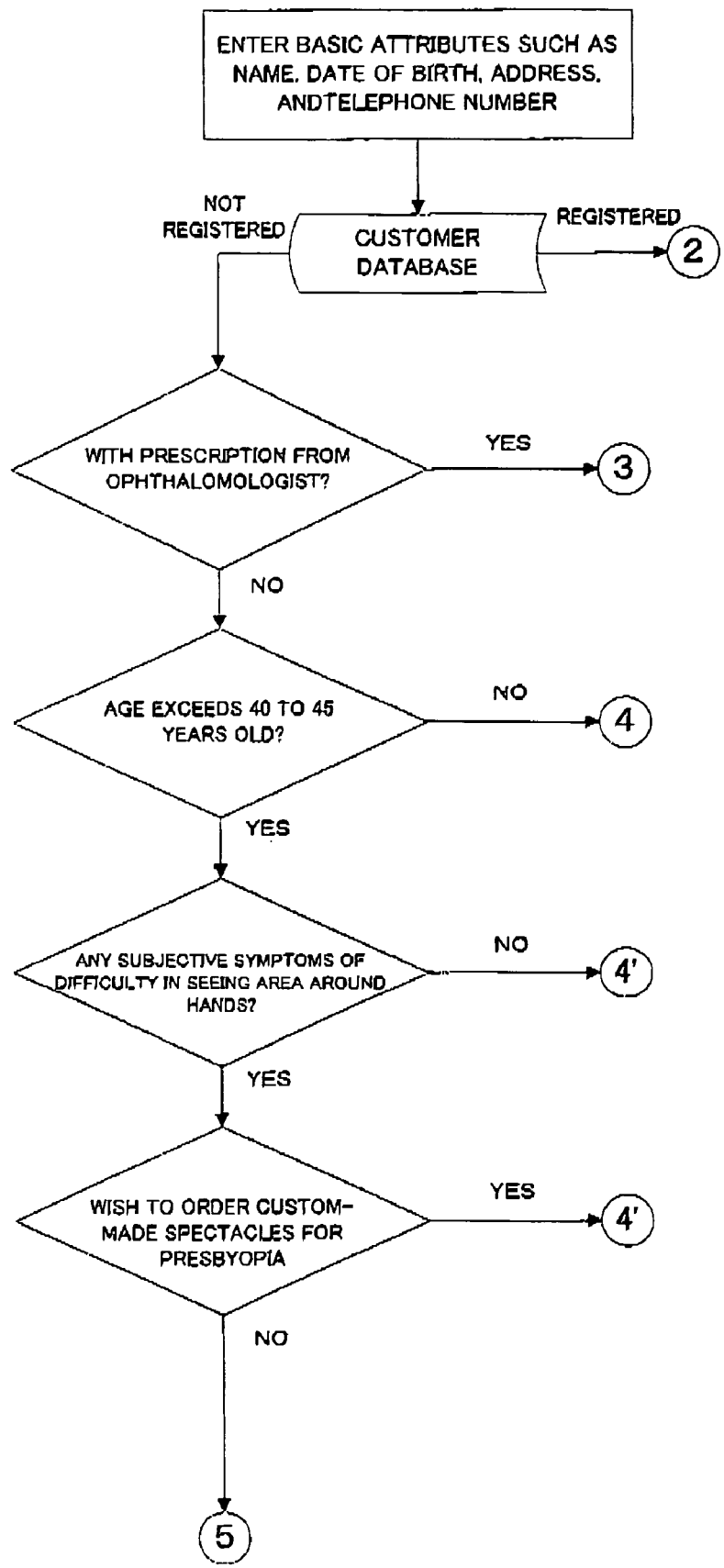
FIG. 3 is a diagram showing a process of categorizing the user in the process of the spectacle and contact lens selecting system.
Figure 4:
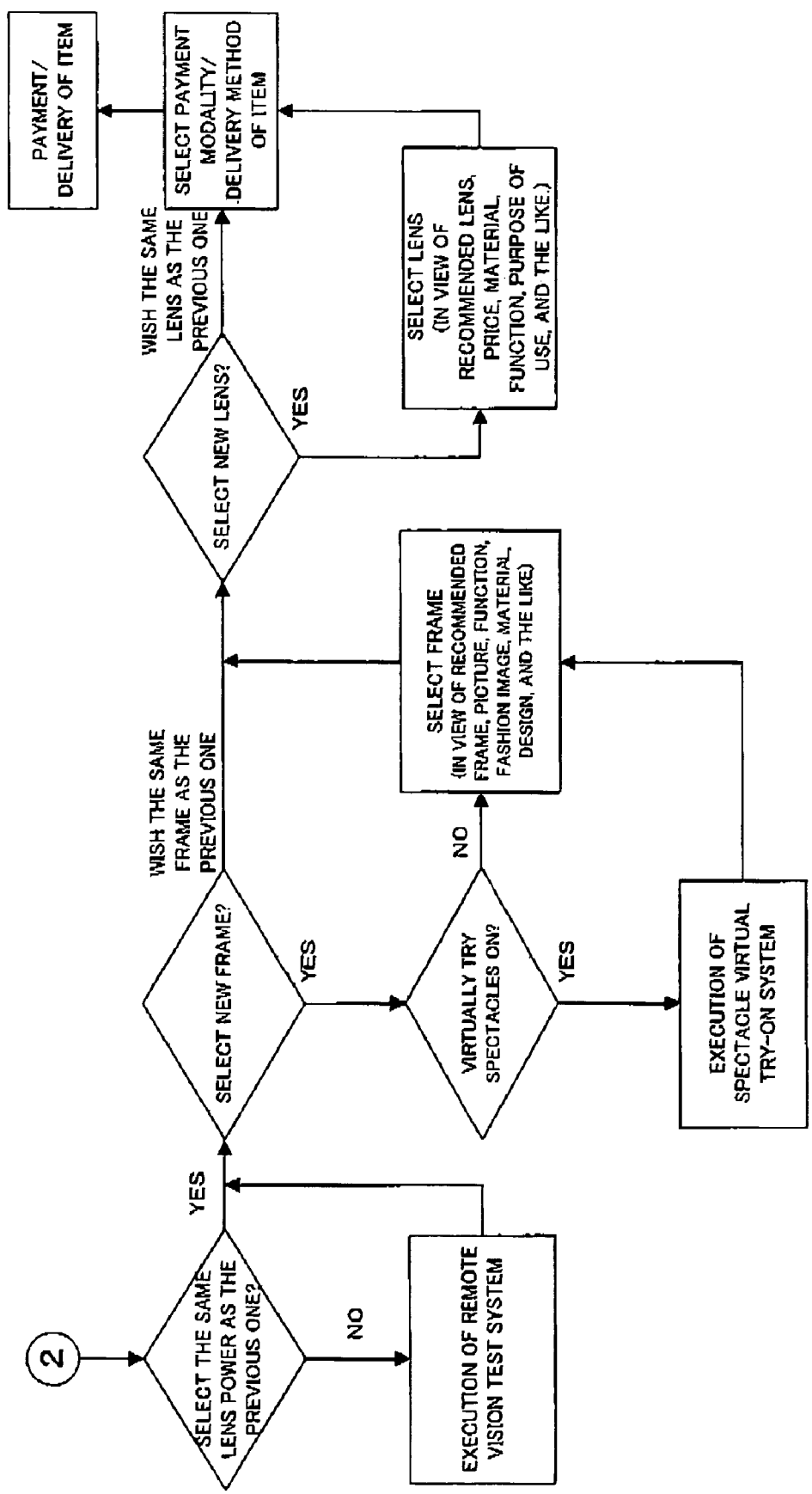
FIG. 4 is a diagram showing a process where the user is a returning customer.
Figure 5:
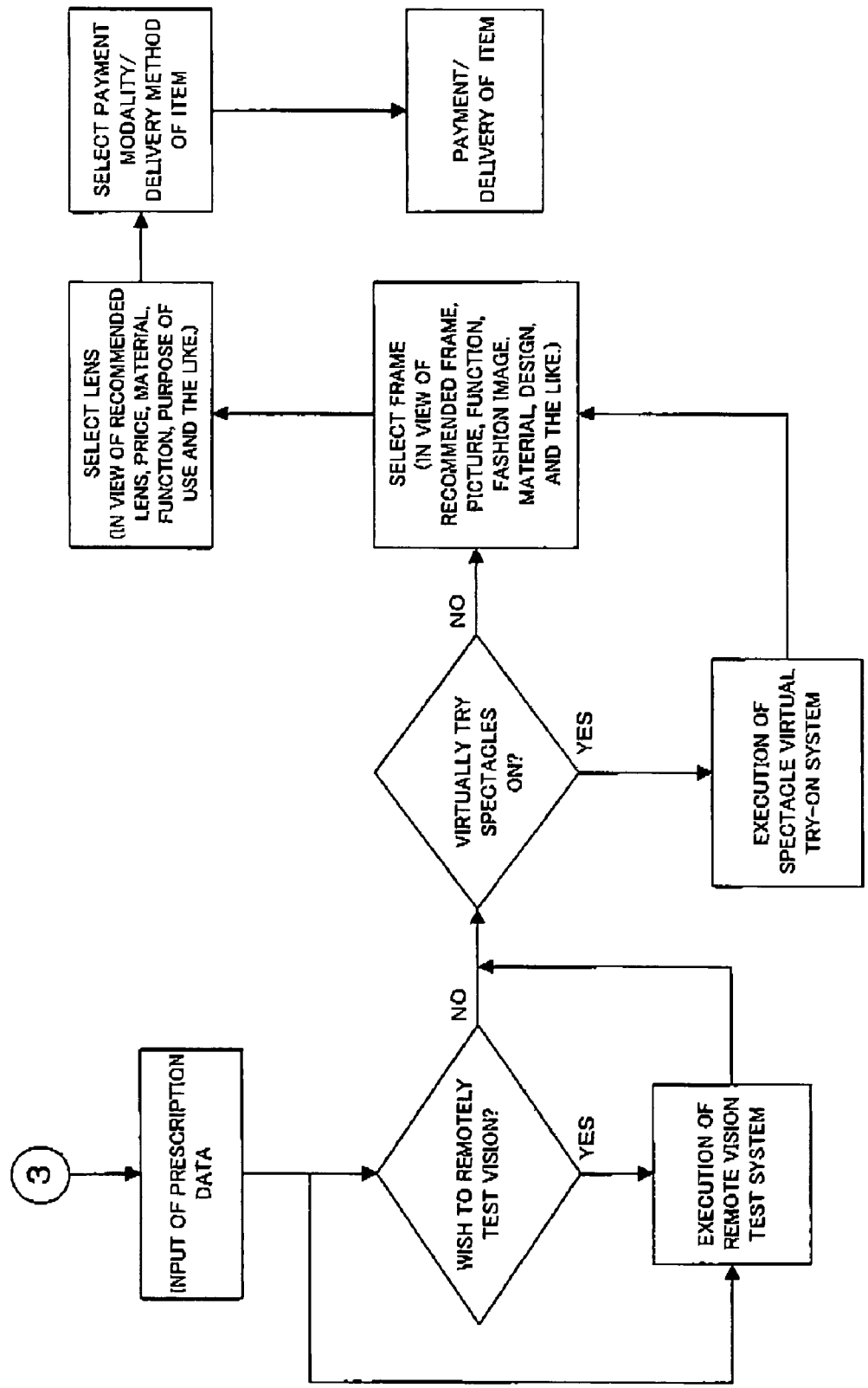
FIG. 5 is a diagram showing a process where the user is not a customer but has a prescription.
Figure 6:
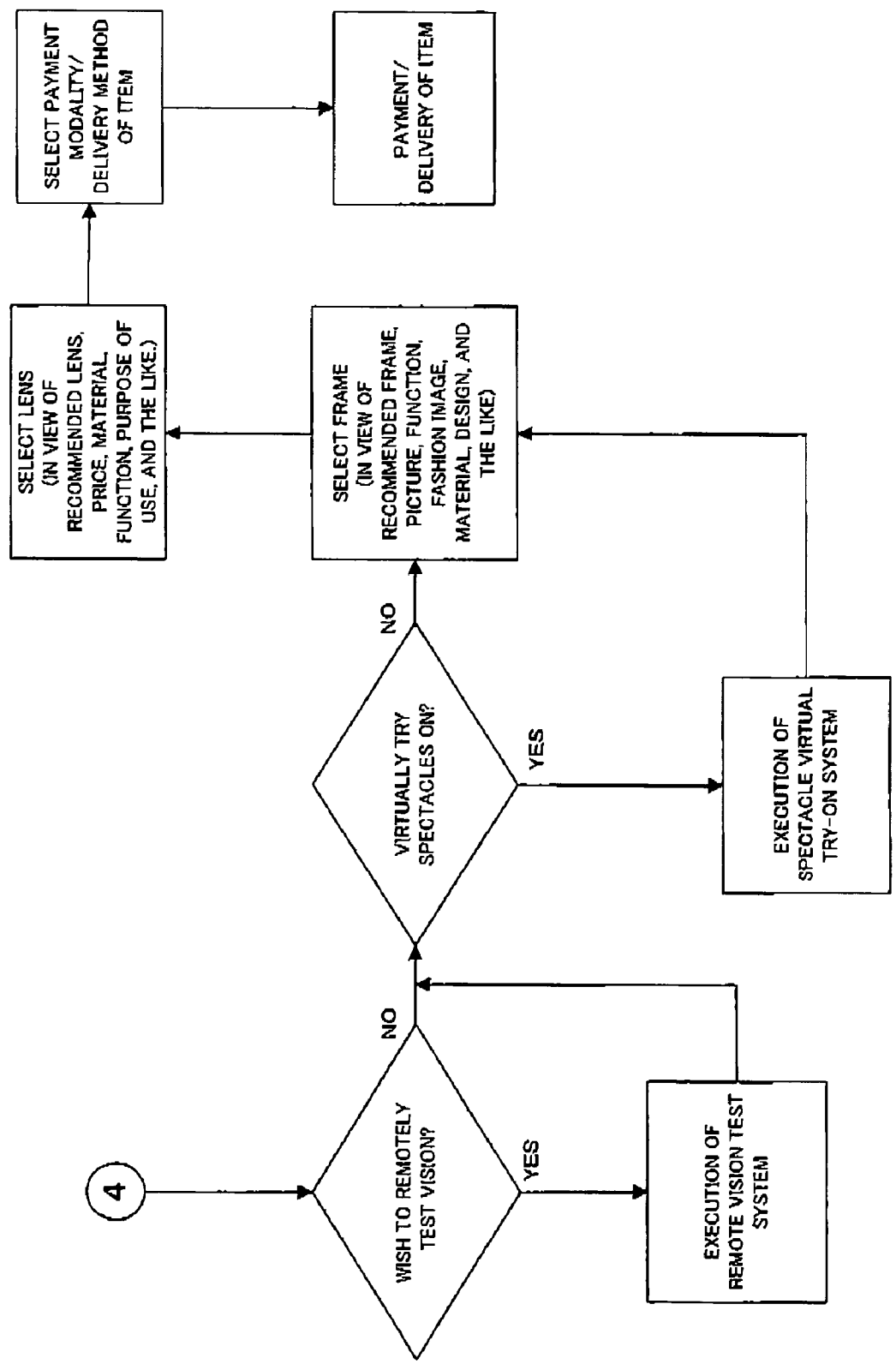
FIG. 6 is a diagram showing a process where the user is not a customer, does not have a prescription, and does not intend to wear a pair of spectacles for presbyopia.
Figure 7:
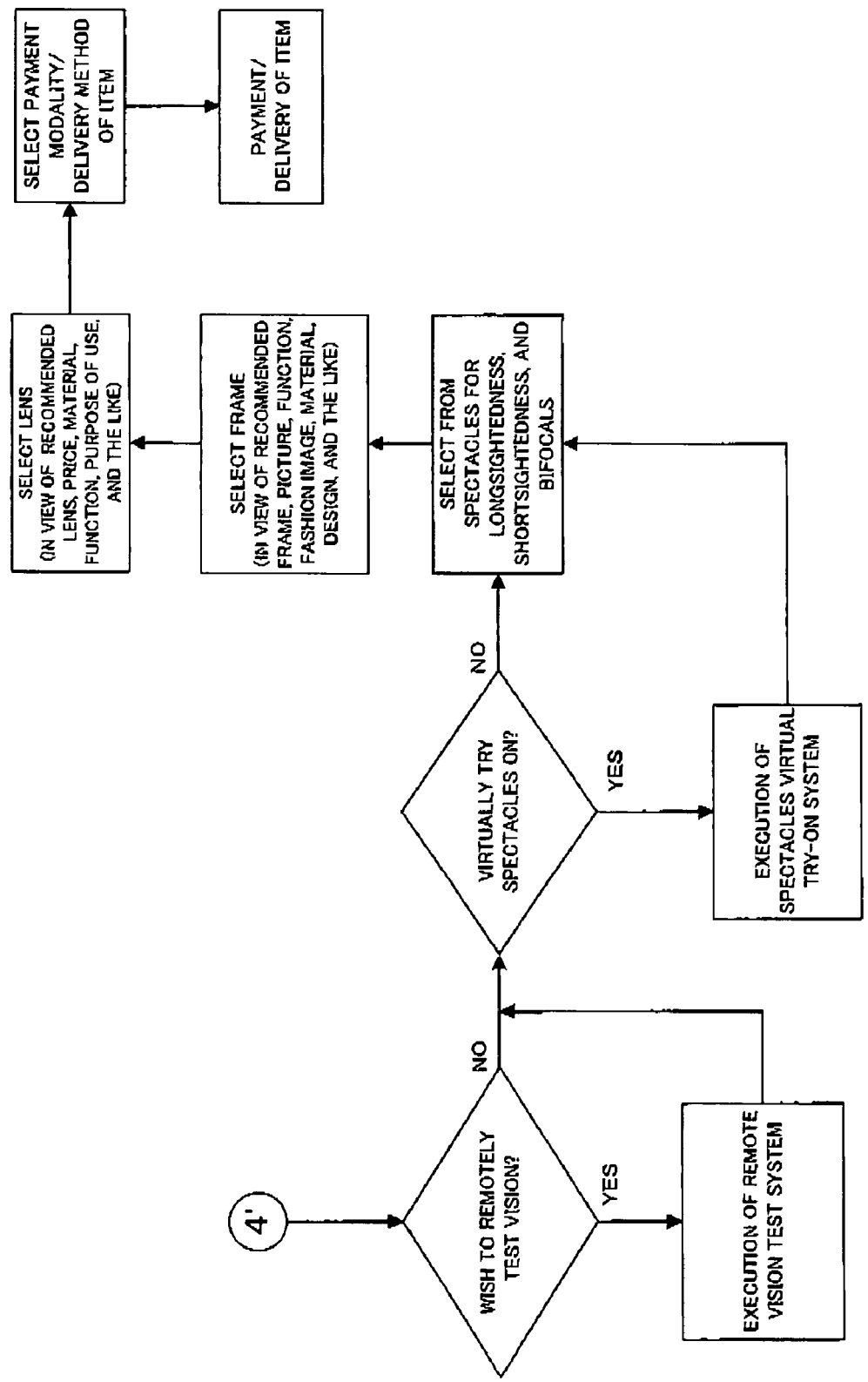
FIG. 7 is a diagram showing a process where the user is not a customer and does not have a prescription with no subjective symptom of presbyopia.
Figure 8:
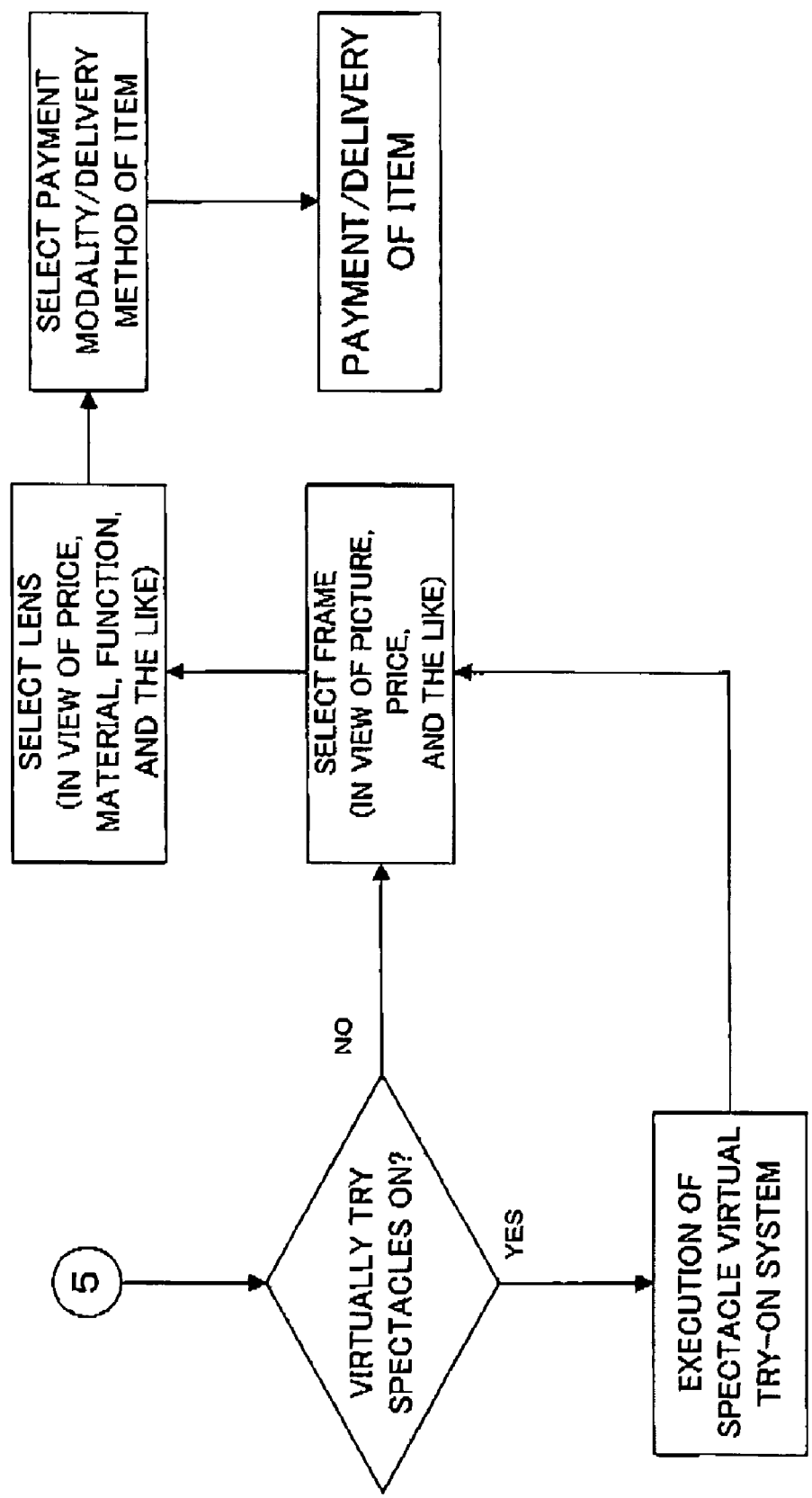
FIG. 8 is a diagram showing a process where the user prefers a pair of ready-made spectacles for presbyopia.

FIGS. 3 to 8 show a process of the spectacle and contact lens selecting system. FIG. 3 is a view showing a process for first categorizing the user. FIG. 4 is a view showing a process where the user is a returning customer. FIG. 5 is a view showing a process where the user is not a customer but has a prescription. FIG. 6 is a view showing a process where the user is not a customer, does not have a prescription, and does not intend to wear a pair of spectacles for presbyopia. FIG. 7 is a view showing a process where the user is not a customer and does not have a prescription with no subjective symptom of presbyopia. FIG. 8 is a view showing a process where the user prefers a pair of ready-made spectacles for presbyopia.

First, when the spectacle order/sales service center 2 accepts the connection from the user client 1, it transmits a basic attribute entry screen for prompting input of basic attributes, such as a name, the date of birth and a telephone number. The user client 1 receives and displays the basic attribute entry screen so as to transmit the basic attributes input by the user to the spectacle order/sales service center 2. The spectacle order/sales service center 2 receives the input basic attributes so as to search the customer database by the spectacle order/sales processing unit 23.

If, as a result of the search, it is determined that the user is a customer who has already purchased spectacles, the process proceeds to FIG. 4 where an inquiry screen for confirming the desires of the user is transmitted to the user client 1. If the user selects "I select the same lenses as the previous ones and the same frame as the previous one" on the inquiry screen, lenses are created based on the vision test data, the frame information data, and the lens information data managed by the customer database (basket database). If the user wants to get new lenses and/or a new frame on the inquiry screen, a step selecting screen for transition to a "lens power deciding step," a "frame selecting step," and a "lens selecting step" is transmitted to the user client 1. If the user selects "I don't want the same lens power as the previous one" on the selection screen, the "lens power decision step" is performed. If "I select new frames," the "frame selecting step" is performed. If "I select new lenses," the "lens selecting step" is performed. At the "lens power deciding step" in this case, a "remote vision test system" described below is performed. At the "frame selecting step", an inquiry screen for making an inquiry whether a spectacle wearing virtual try-on is performed or not is transmitted to the user client 1. If the user selects "I try the spectacles on," the "spectacle virtual try-on system" is performed.

If he/she is not a customer, a prescription confirmation screen for inquiring whether he/she has a prescription from an ophthalmologist or not is transmitted to the user client 1. If the user selects "I have a prescription from a doctor" on the prescription confirmation screen, the process proceeds to FIG. 5 where a prescription entry guidance screen is transmitted to the user client 1. The user inputs the prescription as image data from a scanner in accordance with the guidance of the screen or as text data from the keyboard so as to transmit it to the spectacle order/sales service center 2. Then, as in the above-described case, the step selecting screen for the transition to the "lens power deciding step," the "frame selecting step," and the "lens selecting step" is transmitted to the user client 1 so as to execute each of the processes in response to the request of the user.

If the user selects "I don't have a prescription," an inquiry screen for making an inquiry whether the age of the user exceeds 40 through 45 years old or not is transmitted to the user client 1. If the user selects "I am 40 through 45 years old or below" on the inquiry screen, the process proceeds to FIG. 6 where the step selecting screen for transition to the "lens power deciding step," the "frame selecting step," and the "lens selecting step" is transmitted to the user client 1 so as to execute each of the processes in response to the request of the user.

If the user selects "I am older than 40 through 45 years old," an inquiry screen whether he/she has the subjective symptom that he/she cannot clearly see in the vicinity of his/her hands or not is also transmitted to the user client 1. If the user selects "I don't have any subjective symptoms" on the inquiry screen, the process proceeds to FIG. 7 where the step selecting screen for transition to the "lens power deciding step," the "frame selecting step," and the "lens selecting step" is transmitted to the user client 1 so as to execute each of the processes in response to the request of the user. In this case, since there is a possibility that he/she has presbyopia in view of the age of the user, a "step of selecting the type from farsightedness, shortsightedness and bifocals" is executed.

If the user selects "I have a subjective symptom," the spectacle order-sales service center 2 determines that the user has presbyopia and transmits an inquiry screen for inquiring if he/she prefers custom-made spectacles for presbyopia or not to the user client 1. If the user selects "I prefer custom-made spectacles" on the inquiry screen, the process proceeds to FIG. 7 where the step selecting screen for transition to the "lens power selecting step," the "frame selecting step," and the "lens selecting step" is transmitted to the user client 1 to execute each of the processes in accordance with the request of the user. In this case, the "step of selecting from spectacles for farsightedness, short-sightedness, and bifocals" is further executed.

If the user selects "I prefer ready-made spectacles for presbyopia," the process proceeds to FIG. 8 so as to decide a lens power determined from the age of the user and then to transmit the step selecting screen for transition to the "frame selecting step" and the "lens selecting step" to the user client to execute each of the processes in response to the request of the user.

Although it is described in the above process that the basic information of the user is first input, a user ID and a password may be issued to the user who has registered the basic information in advance so as to enter the user ID and the password when the user connects from the user client 1 to the spectacle order/sales service center 2 for authentication. In this case, it can be determined based on the user ID whether the user is a customer who has already purchased spectacles or not.

Next, a method of providing a service will be specifically described by using an example of a screen displayed on the user client 1.

Figure 11:
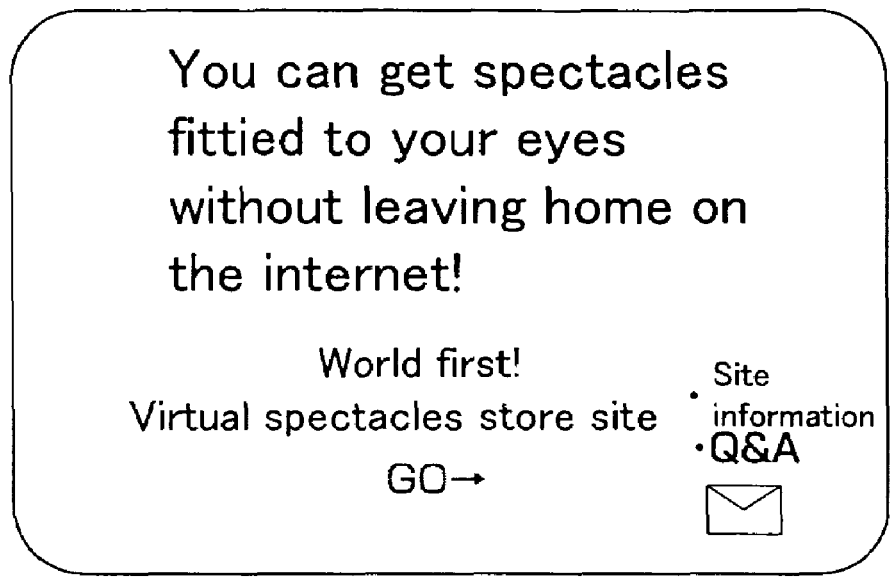
FIG. 11 is a schematic view of a screen at the top of a site.
Figure 12:
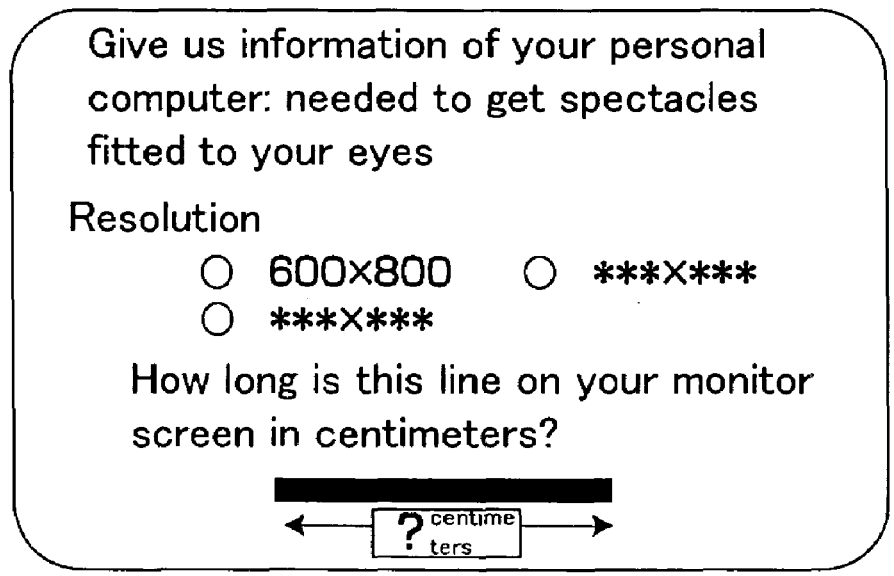
FIG. 12 is a schematic view of a collecting screen of personal computer screen information.

First, the spectacle order/sales service center 2 first transmits a screen at the top of a site (FIG. 11) to the user client 1 and subsequently transmits a personal computer screen information collecting screen (FIG. 12) to the user client 1 so as to instruct the purchaser to enter display (monitor) information, such as the resolution and size of the personal computer screen, thereby acquiring the display information input by the user client 1.

Figure 13:
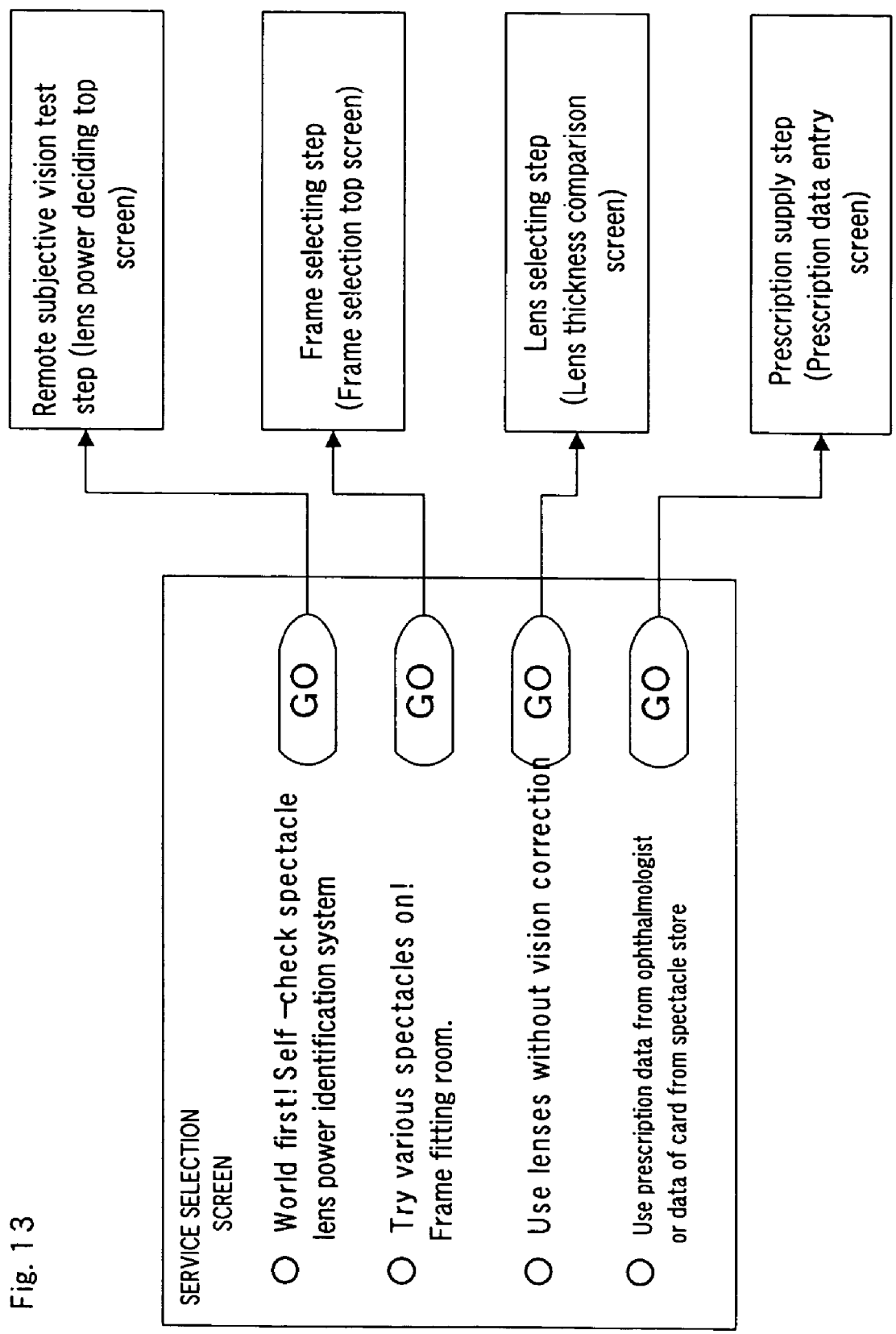
FIG. 13 is a schematic view of a service selection screen.

Next, on a service selecting screen (FIG. 13) transmitted from the spectacle order/sales service center 2, the user clicks any one of the "remote subjective vision test step (World first! Self-check spectacle lens power identification system)," the "frame selecting system (Try various spectacles on! Frame fitting room)," the "lens selecting step (Use lenses without vision correction)," and the "prescription supply step (Use prescription data from an ophthalmologist or data of a spectacle store card)" so as to transmit the intent of the user from the user client to the spectacle order/sales service center 2.

When lens selection criteria is determined at the remote subjective vision test step or the prescription supply step, the process proceeds to the lens selecting step.

Next, the lens selecting step will be described.

When the user decides to use the most recent vision data and therefore clicks "Select the same lenses as the previous ones," when the user decides to have spectacles made based on prescription data from a doctor and therefore clicks "Select lenses in accordance with the prescription," or when the user determines to purchase ready-made spectacles for presbyopia and therefore clicks "Select ready-made spectacles for presbyopia," the lens selecting unit 26 selects lenses based on the respective data.

If the user wants to remotely test his/her vision even though he/she has the most recent vision data or a prescription from a doctor, the user proceeds to the remote vision test step by the vision deciding unit 28 so as to test his/her vision.

Although various lenses are registered as a database (FIGS. 9 and 10) in the spectacle order/sales service center 2, the lens selecting unit 26 transmits a lens selection screen, on which a lens satisfying the request of the user input from the user client 1 or a lens recommended by the spectacle order/sales service center 2 to the user is displayed from them, to the user client 1 based on the most recent vision data, the prescription from a doctor, or data obtained by testing with the remote vision test system. Moreover, if the user is a returning customer, the previously purchased lenses are also displayed on the lens selection screen.

As choices in the selection of lenses, a manufacturer name, a model, a purpose of use, lens functions (a lens thickness, a lens weight, endurance, UV protection), a color, a price, and a lens power are provided. The user specifies these options to search a lens, selects a lens that he/she wants to purchase, and transmits it to the spectacle order sale service center 2.

Next, the frame selecting step will be described.

For example, if data regarding functional and decorative aspect of the frames is provided in the spectacle order/sales service center 2 as in the case where he/she is a returning customer, a frame can be specified in view of fashion, image, design and the like.

The frame selection in the case where the frame data in terms of functions and decoration is present in the spectacle order/sales service center 2 will be described below.

Figure 14:
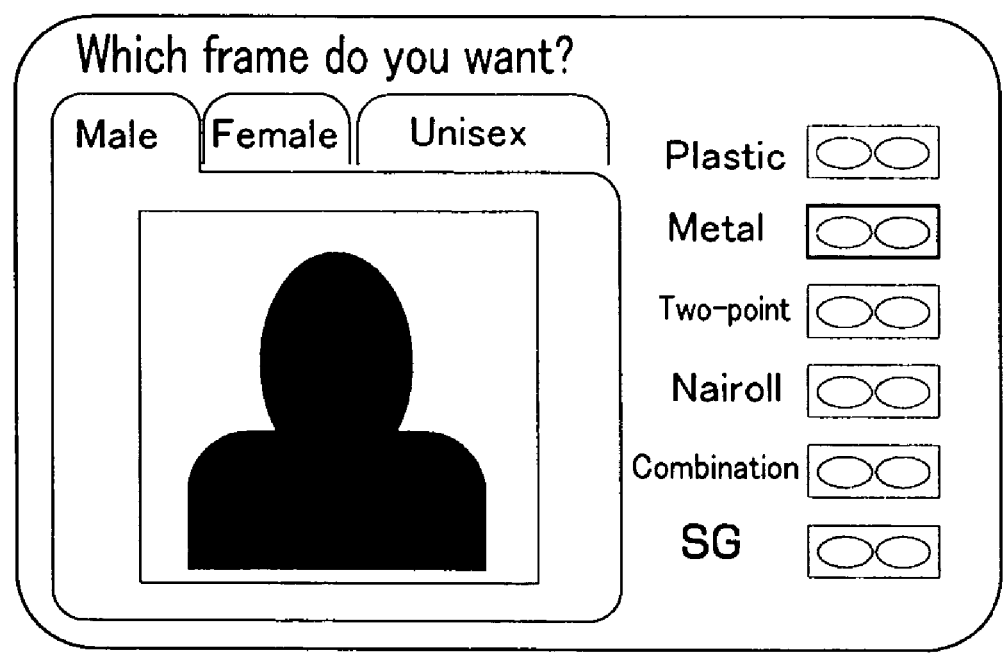
FIG. 14 is a schematic view of a screen at the top of frame selection.

Frames are registered as a database in the spectacle order/sales service center 2. The frame selecting unit 27 transmits a frame selection top screen (FIG. 14), on which typical frames are displayed, to the user client 1. Then, the user answers questions in the form of a questionnaire about fashion, material, design, and budget such that the frame selecting unit 27 selects a frame which seems to be the most suitable based on the data indicating the desires of the user and transmits a frame selection screen to the user client 1.

The frame selection screen categorizes the spectacle frames in accordance with gender/material and displays typical frame images falling within the category.

If he/she is a returning customer, the previously purchased frame is also displayed on the frame selection screen.

Choices of frame include fashion, material, design, price, and other choices. The user reads the options to enter the desired conditions, selects a frame that he/she wishes to purchase from the displayed frame images, and transmits it to the spectacle order/sales service center 2.

At this time, this system is equipped with wearing state display unit to virtually display the selected frame on a model's face or his/her own face.

Figure 25:
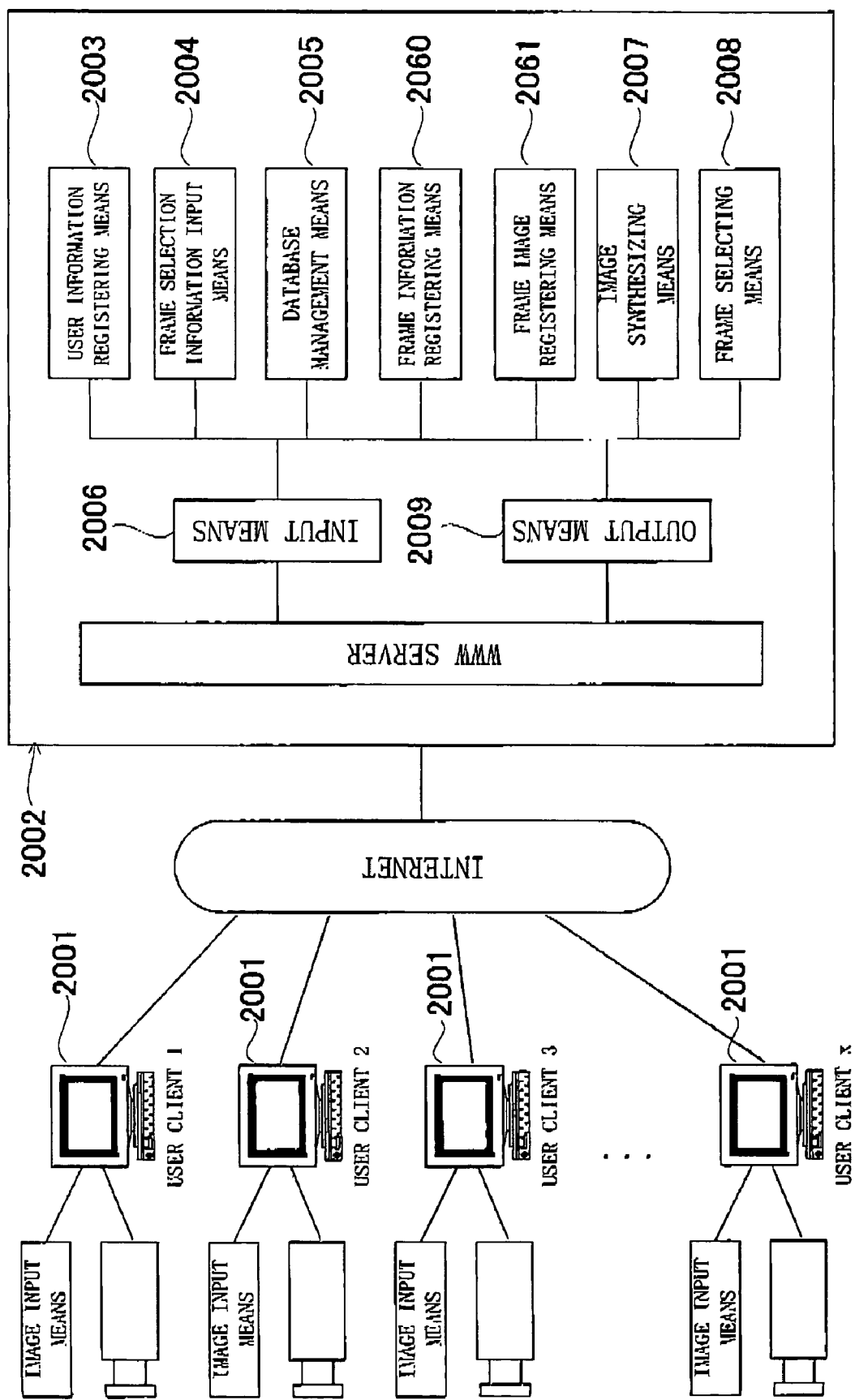
FIG. 25 is a diagram showing an example of a configuration of a lens virtual try-on system equipped for the spectacle and contact lens selecting system according to a preferred embodiment of the present invention.

Next, a preferred embodiment of the wearing state display unit according to the present invention will be described using a spectacle virtual try-on system shown in FIG. 25.

The spectacle virtual try-on system provides a virtual experience in which the user can put various spectacle frames on a face of a model or the user, and is controlled by a user client 2001 and a spectacle order/sales service center 2002. The user client 2001 and the spectacle order/sales service center 2002 are physically connected through a network. In this case, the following description will be given in which the network is the Internet.

The user client 2001 is a terminal used when the user virtually tries spectacles on, and includes, for example, a personal computer having a network connection function. Although a general CRT display or liquid crystal monitor is preferably used as an image display device for displaying a spectacle wearing state, a dedicated image display device such as a head mount display (HMD) or a projection-type display device may be used. Moreover, although a general keyboard or mouse is preferably used as an input device for inputting information such as frame selection information, a dedicated input device such as a pointing device such as a track ball and a joystick, a touch panel, and a switch may be prepared. Furthermore, this user client 2001 includes an image input unit for acquiring a facial image of the user. Although a digital camera is preferably used in this case, any devices capable of digitizing and inputting an image such as a video camera and a scanner may be used. Furthermore, the user client 2001 includes a WWW browser as an interface for accessing the spectacle order/sales service center 2002 so as to receive a service therefrom.

The spectacle order/sales service center 2002 is a server for providing a spectacle virtual try-on service. It includes information processing equipment such as a personal computer and a work station which has a network connection function, and is connected to the user client 2001 through the Internet. The spectacle order/sales service center 2002 includes a WWW server as a contact point for providing a service to the user client 2001. Moreover, the spectacle order/sales service center 2002 includes a user information registering unit 2003 for registering user information including a facial image of the user, a frame selection information input unit 2004 for inputting selection information at the selection of a frame by the user, a database management unit 2005 for conducting access management of the database, a frame information registering unit 2060 for registering the functional structures and the decorative structures of frames to be sold, a frame image registering unit 2061 for registering the images of frames to be sold, an image synthesizing unit 2007 for synthesizing a frame image and a facial image of a model or the user, and a frame selecting unit 2008 for selecting a corresponding frame based on the frame selection information. The spectacle order/sales service center 2002 is connected to the WWW server through an input unit 2006 and an output unit 2009. Each of the units is activated by a CGI of the WWW server as required so as to provide a spectacle virtual try-on service to the user client 2001. Moreover, the WWW server has a user authentication function for authenticating that the user client 2001 is a legitimate user.

The database managed by the database management unit 2005 includes a user information database, a frame selection information database, a frame functional structure database, and a frame decorative structure database as shown in FIGS. 26 to 29.

Next, a process for providing a spectacle virtual try-on service by this system to the user will be described.

First, a service provider activates the frame information registering unit 2060 to input functional structure data and decorative structure data of spectacles to be sold by the keyboard or other suitable input device so as to register them on the databases.

As shown in FIG. 28 the frame functional structure data of each frame includes a size or an actual size (44Ø-62Ø), and features such as a shape-memory alloy, super-light weight, super-elasticity, simultaneous function as sunglasses, portability and so forth. Also included are functions such as the distance between the right and left pupils, the widths from the center of the right and left pupils to the feet of the ears, the opening angles of temples determined based on the widths from the center of the right and left pupils to the feet of the ears, the distances from the feet of the ears to the tops of the corneas, the bending positions of the temples, the distances between the tops of the corneas and the foot of the nose, and the opening angles of pad bridges determined based on the distances between the tops of the corneas and the foot of the nose. As shown in FIG. 29, the frame ornamental structure data includes shapes, such as Wellington, Lloyd, Oval, Square, Tonneau, Boston, Butterfly, and Auto (prop). Materials are rimless (two-point, three-point), metal+nylon rimmed, celluloid+nylon rimmed, metal, celluloid, brow-line, combination and so forth. Brands include various brands, and colors include various colors.

The frame image registering unit 2061 is also activated to input images of the frames of spectacles to be sold from the scanner so as to register them on the database.

Next, when the user accesses the WWW server by using the WWW browser of the user client 2001, the WWW server transmits a user authentication screen. The user authentication screen instructs a user to input user authentication information, such as a user ID and a password. If the user authentication has already been completed at the previous step, it need not be executed again and therefore is skipped.

The database management unit 2005 makes a search in the user information database using the input user authentication information so as to execute the authentication.

If a service is provided for the user for the first time, the user information registering unit 2003 is activated to transmit a basic attribute entry screen to the user client 2001. After the user enters the user's basic attributes, for example, name, address, date of birth, telephone number, eye function (he/she cannot see clearly in the area around his/her hands, etc.), requirements for spectacles in accordance with the screen, a user ID and a password are issued to the corresponding user such that the received basic attribute information of the user is registered on the user information database.

At the completion of the user authentication, the frame selection information input unit 2004 is activated such that a frame selection information entry screen instructing the user to input frame selection information is transmitted to the user client 2001. The frame selection information entry screen is for inputting criteria (fashion, a budget, functions, fitness to the face, etc.) for selection of a frame by the user. The user inputs frame selection criteria such as fashion, a budget, functions, and the fit to the face on the frame selection information entry screen.

Figure 15:
FIG. 15 is a schematic view of a PD measurement screen.

Next, a PD measurement screen (FIG. 15) is transmitted to the user client 2001 for measurement of the position of a pupil such that the pupil is positioned at the center of a lens.

Figure 16:
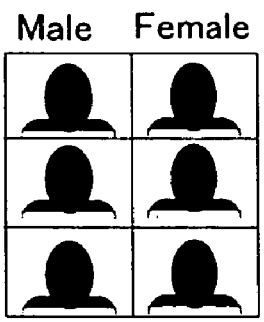
FIG. 16 is a schematic view of a facial image selection screen.
Figures 17A, 17B:
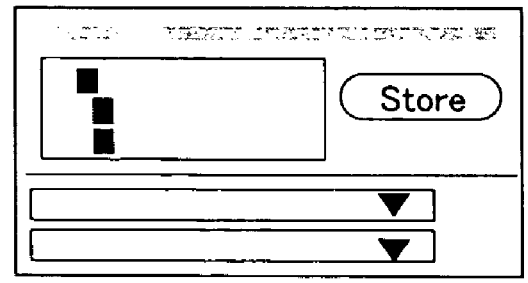
FIG. 17 is a schematic view of a self-portrait upload screen.

When the entry of the frame selection criteria in the text data and the PD measurement are completed, a facial image selection screen (FIG. 16) which asks "On which face do you want to try frames?" is transmitted. If the user selects "Use a model face," the process proceeds to a next virtual frame selection screen. If the user selects "Use my self-portrait," a self-portrait upload screen (FIG. 17) is transmitted.

On the self-portrait upload screen, a screen which asks "Where is your picture data?" is transmitted such that the user selects either "Use digital camera picture data" or "Use picture data obtained by a scanner." The user retrieves front and lateral (both on the right and left sides) facial images into the user client 2001 by the image input device so as to transmit them to the spectacle order/sales service center 2002.

The frame selection information input unit 2004 receives the text data of the frame selection information and the image data (the facial images of the user) transmitted from the user client 2001 so as to register necessary information on the frame selection information database in the following manner.

Figure 30:
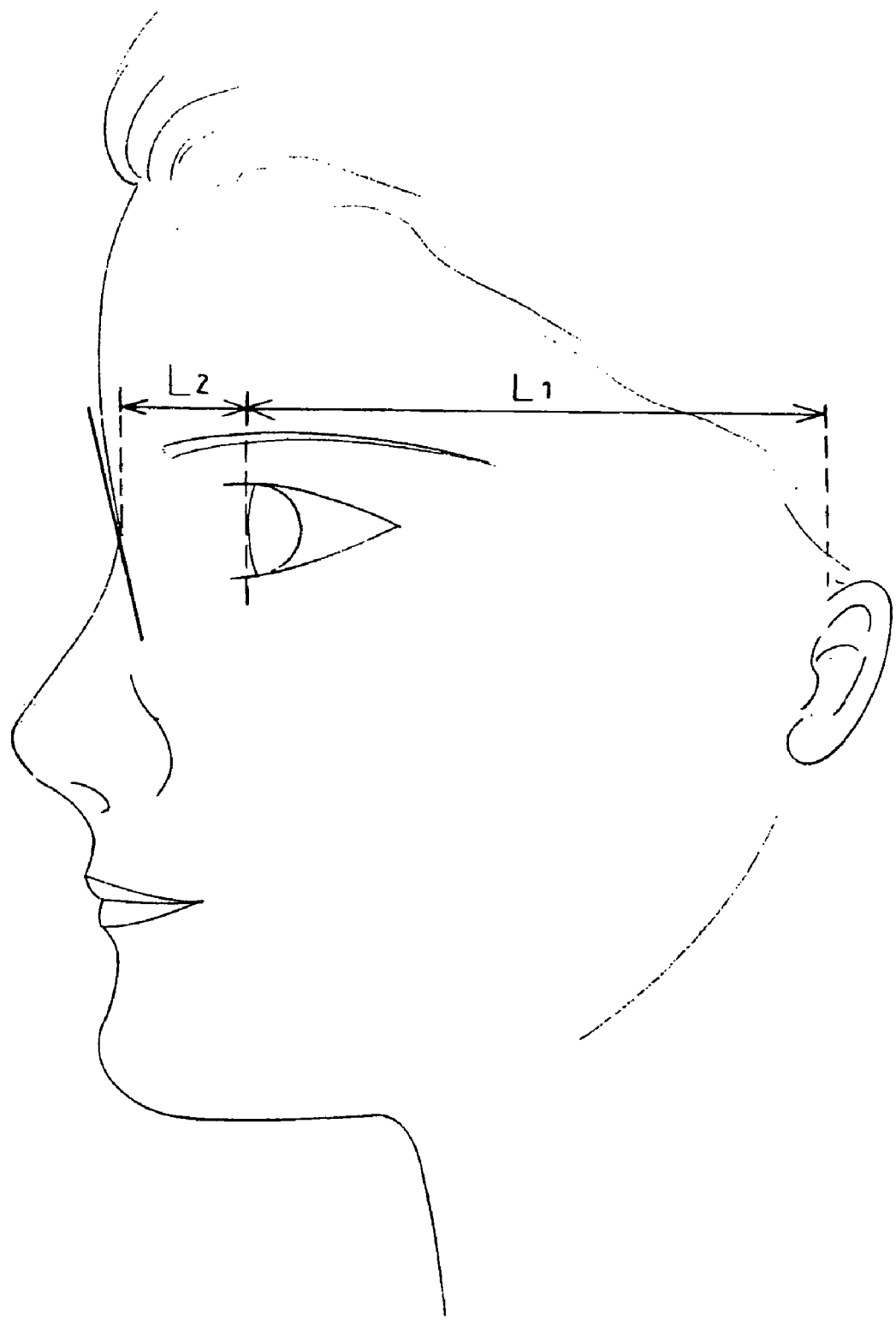
FIG. 30 is a schematic view showing a measurement method on the lateral side of a facial image.

(1) Based on the side images (FIG. 30) of the user, the distances ($L_1$) between the feet of the ears and the tops of the corneas of the user are measured separately for the left and right, and the resulting data is registered. Based on the aforementioned measurements, the positions at which the temples are bent are determined separately for the left and right, and then registered.

(2) Based on the side images of the user, the distances ($L_2$) between the tops of the corneas of the user eyes and the foot of the nose are measured, and an average value of the left and right distances is registered. The distance $L_2$ is usually about 12 mm. Based on the above measurements, the opening angles of the pad bridges are determined and registered.

Figure 31:
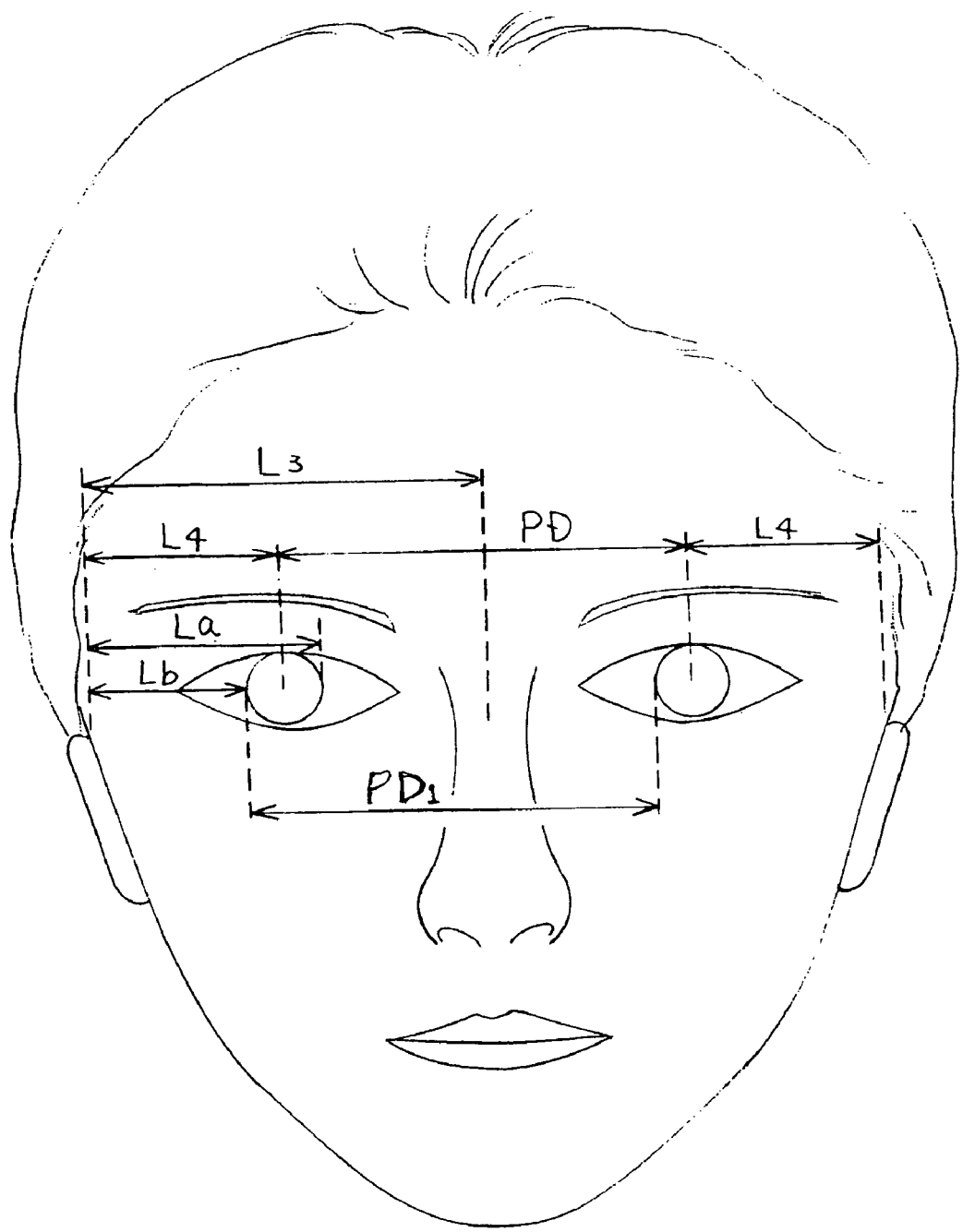
FIG. 31 is a schematic view showing a measurement method on the front side of the facial image.

(3) Based on the front image (FIG. 31) of the user, the widths ($L_3$) from the center of the pupils of the right and left eyes to the feet of the ears are measured separately for the left and right, and are then registered. Based on the above measurements, the opening angles θ of the temples are determined separately for the left and right and are registered.

For the widths from the center of the pupils of the right and left eyes to the ears, the distance between the pupils (PD) is first determined. However, the pupils cannot be precisely detected on the user face image, and therefore the distance between the pupils (PD) is approximated, for example, from the distance ($PD_1$) between the left side of the left eye and the left side of the right eye.

The pupils cannot be detected from the face image. Therefore, to determine the distance ($L_4$) between the pupil of the left eye and the left ear, the distance from the foot of the left ear to the right side of the left eye ($L_a$) and the distance from the foot of the left ear to the left side ($L_b$) of the left eye are determined. Then, the distance ($L_4$) between the pupil of the left eye and the left ear is determined by calculating an average of them. The distance between the right eye and the right ear is also determined in the same manner.

Figure 32:
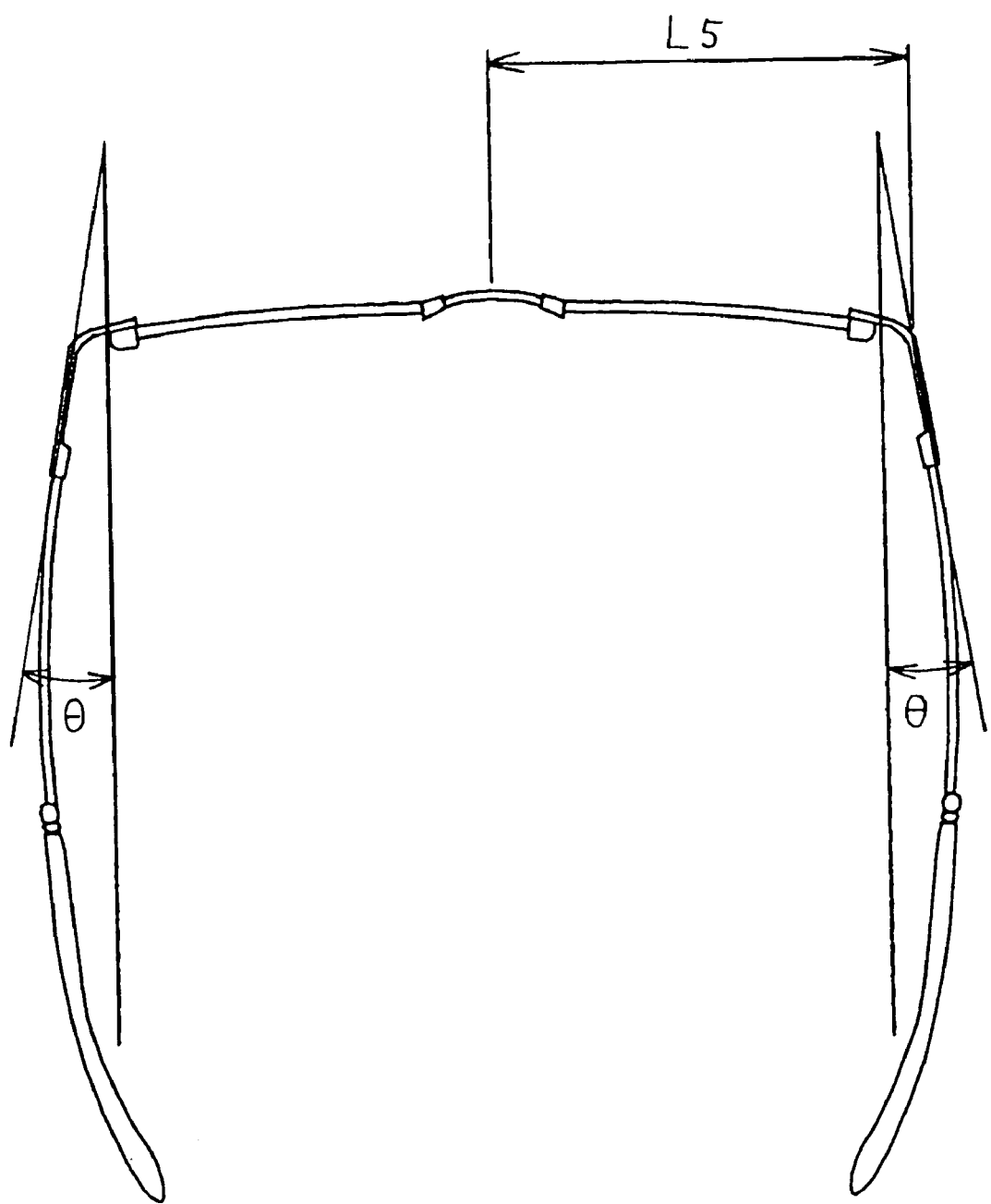
FIG. 32 is a schematic view showing a frame adjusting method.

The opening angles θ of the left and right temples of the spectacle frame are adjusted, for example, by correcting and bending the temples by the amount of angle obtained from the following equation.

$$PD/2 + L_4 - L_5$$

where $L_5$ is the front size of the spectacle frame (Refer to FIG. 32).

(4) When bifocal lenses are specified, an additional bending angle of 5 degrees is provided for the angle of inclination of the lens surface. For this reason, the opening angle of the pad bridges is determined and registered after being corrected with the additional angle of bending.

Thus, the frame selection information input unit 2004 performs computations to create functional structure data, ornamental structure data, and face image data, which are in turn stored by the database management unit 2005 in conjunction with the face image data.

At the spectacle order/sales service center 2002, the frame information registering unit 2060 and the frame image registering unit 2061 store in advance the frame functional structure, the frame ornamental structure, and the frame image of each frame. An appropriate frame is selected corresponding to the functional structure data, ornamental structure data, and face image data according to the frame selection criteria transmitted from the user client 2001.

After the selection of several types of frames conforming to the frame selection information by the frame selecting unit 2008, the virtual frame selection screen (FIG. 18) is transmitted to the user client 2001. On the virtual frame selection screen, "Try various frames and save the ones you like (up to four frames) for now" is displayed so as to instruct the user to select frames that interest him/her. As a result, the user can virtually try the selected frames on and save frames that interest him/her in view of the results of virtual try-on.

On the virtual frame selection screen, search criteria such as "material and price range," "material and brand,""material and price range and brand," etc. are displayed. As choices for material, "Plastic," "Metal," "Two-point,""Nairoll," "Combination," "SG," and other suitable choices are displayed such that a selection can be made. As choices of price range, "5000 to 9999 yen," "10000 to 14999 yen," "15000 to 19999 yen," "20000 to 30000 yen," and other suitable ranges are pull-down displayed such that a selection can be made. As choices of brand, various brand names are pull-down displayed such that a selection can be made. A maximum of four frames are permitted to be saved. If the number of frames exceeds four, the frames are appropriately reselected so as to delete the unnecessary ones.

Figure 18:
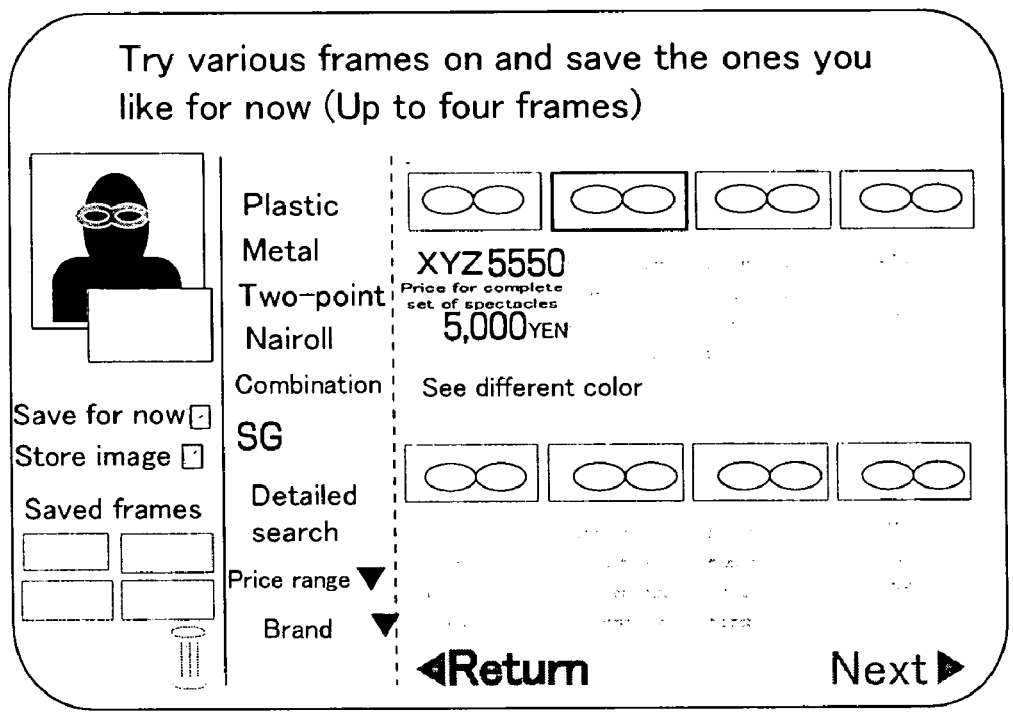
FIG. 18 is a schematic view of a virtual frame selection screen.

An image of each of the selected frames is resized and synthesized so as to fit to the facial image of the user by the image synthesizing unit 2007 to generate a spectacle wearing image. Then, the generated spectacle wearing image is transmitted to the user client 1 as part of the virtual frame selection screen (FIG. 18). At this time, lateral images of the frame may be simultaneously displayed. Furthermore, a spectacle wearing image obtained by synthesizing the image and the lateral images of the user may be generated and displayed by the image synthesizing unit 2007. As a result, the user can confirm the fit on the lateral faces of the frame.

Figure 19:
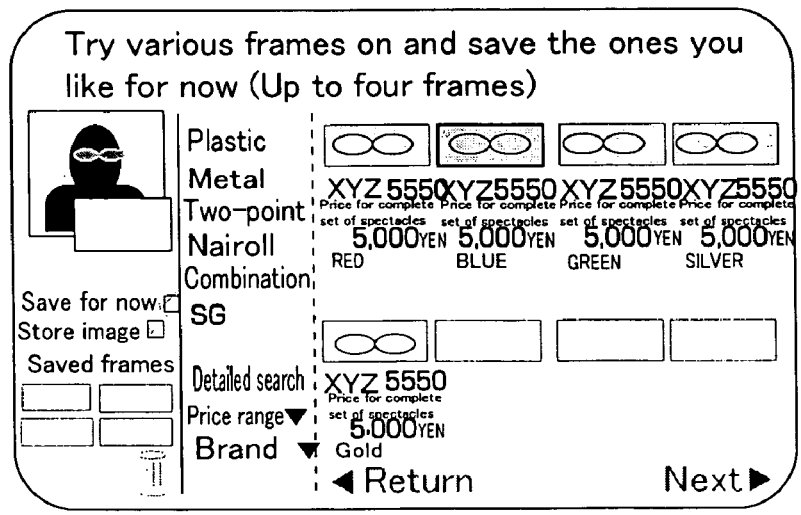
FIG. 19 is a schematic view of a different color display screen.

If "See a different color" is selected on the virtual frame selection screen, a different color display screen (FIG. 19) is transmitted to the user client 2001. On the different color display screen, all different colors of the same model are displayed to show items in different colors. If the number of frames in different colors is less than 8, a field is displayed as a blank.

The user sees a spectacle wearing image displayed on the user client 2001 so as to confirm if the selected frame meets his/her requirements.

If an image of a frame different from the desired one is transmitted or it is desired to see the face with another frame, the user specifies the frame selection information again so as to transmit it to the spectacle order/sales service center 2002. As a result, another frame is selected by the same method as described above. A spectacle wearing image obtained by synthesizing an image of the frame selected by the user and the facial image is generated by the image synthesizing unit 2007 so as to be transmitted to the user client 2001 again.

Figures 20, 21:
FIG. 20 is a schematic view of a saved-item confirmation screen.
FIG. 21 is a schematic view of a purchased frame confirmation screen.

Next, to enable the user to confirm the frames saved on the virtual frame selection screen (FIG. 18) and the different color display screen (FIG. 19), a saved-item confirmation screen (FIG. 20) is transmitted to the user client 2001. On the saved-item confirmation screen, "Confirm the saved frames and select the one that I want to purchase" is displayed. As a result, a frame can be selected simultaneously with a virtual experience.

If the user purchases the frame confirmed through the virtual experience with color lenses, a predetermined part is clicked.

Next, a purchased frame confirmation screen (FIG. 21) is transmitted to the user client 2001 so as to instruct the user to confirm the type of frame and the type of lenses to be purchased. On the purchased frame confirmation screen, an image with the selected frame on, the type of frame and the type of color lenses are displayed. If he/she does not want to purchase an item, he/she clicks "Cancel." If he/she wants to purchases the item, he/she clicks "Buy."

If "Buy" is selected on the purchased frame confirmation screen, a lens power selection screen (FIG. 22) for having spectacles made is transmitted to the user client 2001. On the lens power selection screen for spectacles, the question "Which lens power data do you use for the spectacles on this order?" is displayed. As choices, "Use lens power data tested on this site," "Use lenses without vision correction," and "Use prescription data from an ophthalmologist or data of a card from a spectacle store" are displayed so as to instruct the user to make a selection from the "lens power deciding step," the "lens selection step," and the "prescription supply step."

If "Use prescription data from an ophthalmologist or data of a card from a spectacle store" is selected, the process proceeds to the "prescription supply step" so as to transmit a prescription data entry screen (FIG. 23) to the user client 2001. On the prescription data entry screen, "Enter a lens power" is displayed so as to instruct the following input.

PD (in mm)

Right eye S (pull-down display of lens power data: +0.25, −0.25, −0.50, −0.75, −1.00 and the like), C, AX (pull-down display of astigmatism axis data: 180°±22.50, 135±22.5°, 90±22.5°, 45±22.5°, 0±22.5° and the like)

Left eye S (pull-down display of lens power data: +0.25, −0.25, −0.50, −0.75, −1.00 and the like), C, AX (pull-down display of astigmatism axis data: 180°±22.5°, 135±22.5°, 90±22.5°, 45±22.5°, 0±22.5° and the like)

If "Use lenses without vision correction" is selected on the lens power selection screen for spectacles and if the prescription data is input on the prescription data entry screen, a lens thickness comparison screen (FIG. 24) is transmitted to the user client 2001. On the lens thickness comparison screen, "Which lenses do you want for the spectacles? Thickness is displayed in accordance with your lens power" is displayed to show cross-sectional shapes and lens prices for a "standard lens," a "thin lens," and a "thin lens without distortion" such that the user can compare the thicknesses of the lenses.

When the frame is selected, the process proceeds to the payment system.

As described above, according to the spectacle virtual try-on system, the user can put various spectacle frames on the picture data. In addition, he/she can try various spectacle frames on at home through a network, such as the Internet, without going to a store so as to select the most suitable frame meeting his/her own preferences. Moreover, according to this system, since he/she can confirm himself/herself with the selecting spectacle frame on while wearing his own spectacles or contact lenses, that is, with proper vision, a spectacle frame optimal for him/her can be selected.

In the above-described preferred embodiment, the spectacle virtual try-on system, which allows various spectacle frames to be put on the picture data of the user as the wearing state display unit, has been described. However, not only a spectacle frame but also contact lenses may be virtually tried on by using similar image synthesizing unit. In particular, with color contact lenses, the image of the face greatly changes. Therefore, if the image when wearing them can be confirmed, the user is assured to select suitable contact lenses.

Figure 33:
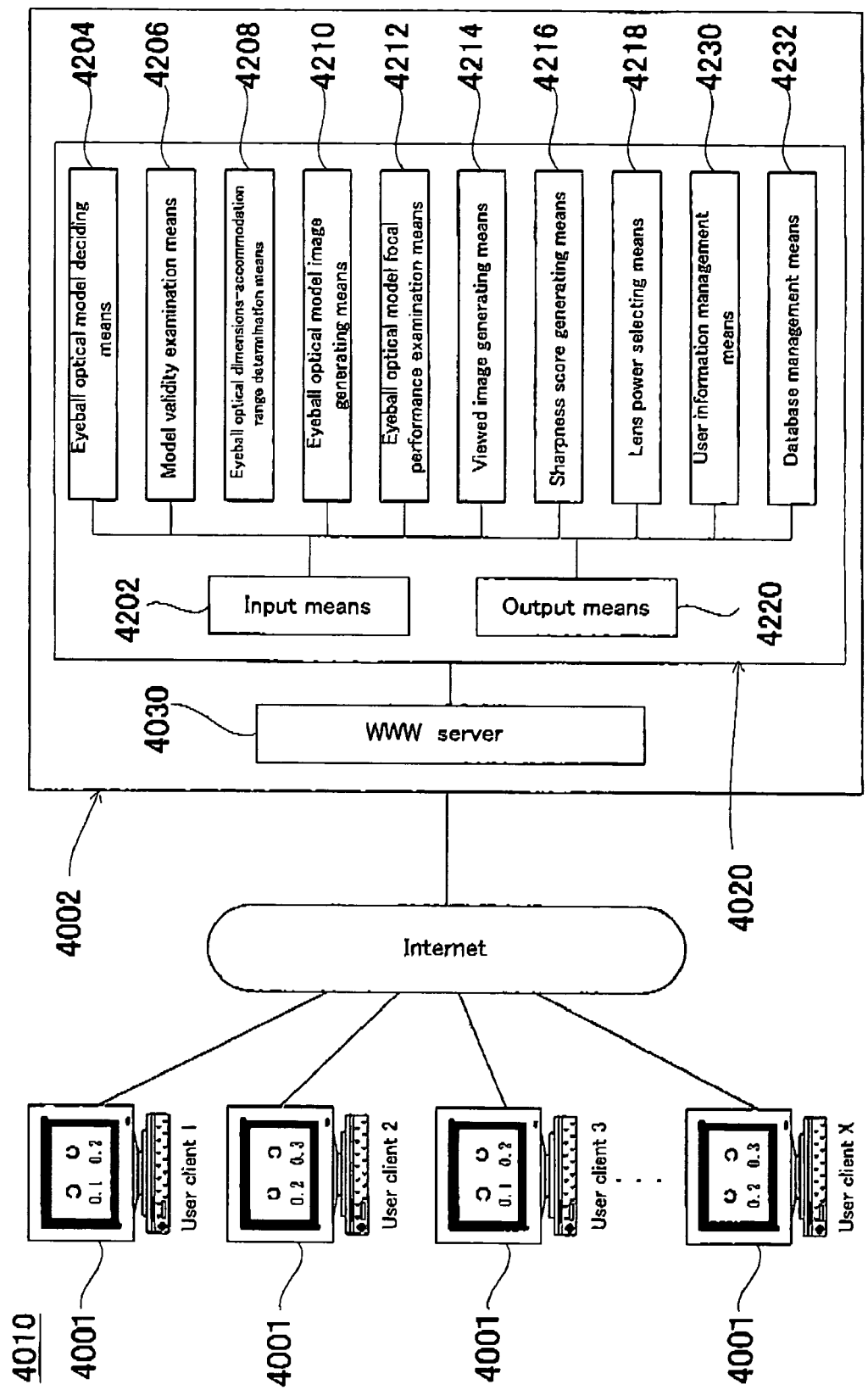
FIG. 33 is a view showing an example of a configuration of a remote subjective vision test system equipped for the spectacle and contact lens selecting system in the preferred embodiment of the present invention.

Next, a first preferred embodiment of lens power determination step is explained below by using a remote subjective vision measurement system as shown in FIG. 33. As illustrated, the remote subjective vision measurement system 10 includes hardware of user clients 4001 and a spectacle order/sales service center 4002. These are physically connected to each other via networks. The following description will be given assuming that the network connecting between the user clients 4001 and the spectacle order/sales service center 4002 is the Internet.

A user client 4001 is a terminal used when the user receives a vision test service. Like the above-described user client 1, a personal computer having an Internet connection function is used as the user client.

A spectacle order/sales service center 4002 is a server for providing a vision test service and includes information processing equipment, such as a personal computer or a work station, having a network connection function so as to be connected to the user client 4001 through the Internet.

The spectacle order/sales service center 4002 includes a WWW server 4030 serving as a contact point for providing a service to the user. Moreover, the spectacle order/sales service center 4002 includes an eyeball optical model deciding unit 4204, a model validity examination unit 4206, an eyeball optical dimensions-accommodation range determination unit 4208, an eyeball optical model image generating unit 4210, an eyeball optical model focal performance examination unit 4212, a viewed image generating unit 4214, a sharpness score generating unit 4216, a lens power selecting unit 4218, a user information management unit 4230, and a database management unit 4232. The spectacle order/sales service center 4002 is connected to the WWW server 4030 through an input unit 4202 and an output unit 4220. Each of the units is activated by a CGI of the WWW server as required so as to provide a vision test service to the user client 4001. Moreover, the WWW server has a user authentication function for authenticating that the user client 4001 is a legitimate user.

The input unit 4202 inputs information about the eyes of a subject, such as wearing conditions of the subject, age, a near point distance, and a far point distance.

The eyeball optical model deciding unit 4204 is designed to determine a start eyeball optical model in accordance with the age of a subject and information regarding the eyes, such as the approximate lens power. The eyeball optical model deciding unit 4204 is designed to determine an eyeball optical model in accordance with such eyeball optical dimensions that the focal state of the eyeball of a subject is optimized at the accommodation midpoint calculated from the near point distance and the far point distance of the subject.

The model validity examination unit 4206 further examines the validity of the eyeball optical model at the accommodation limit on the near point side and/or the far point side.

The eyeball optical dimensions-accommodation range determination unit 4208 is designed so as to determine the range of accommodation of an eyeball at an accommodation midpoint, and in addition displays an image of an eyeball optical model, in which the range of accommodation of the eyeball at the accommodation midpoint is determined.

The eyeball optical model focal performance examination unit 4212 examines a focal state of the eyeball optical model at a near point or a position within the range of accommodation ability in the vicinity of the near point, at a far point or a position within the range of accommodation ability in the vicinity of the far-point, or a position away from the near point and the far point in a naked eye state of the subject. Furthermore, the eyeball optical model focal performance examination unit 4212 examines a focal state of the eyeball optical model of the subject at a near point or a position within the range of accommodation ability in the vicinity of the near point, at a far point or a position within the range of accommodation ability in the vicinity of the far point, or a position away from the near point and the far point after vision correction with spectacles or contact lenses.

The viewed image generating unit 4214 generates visual images viewed by the subject before and/or after the correction by unit of a spectacle or contact lens.

The sharpness score generating unit 4216 derives the sharpness score of the viewing by the subject before and/or after the correction by unit of a spectacle or contact lens.

The lens power selecting unit 4218 examines optical performance when the subject wears spectacles or contact lenses so as to select a lens power.

Figure 34:
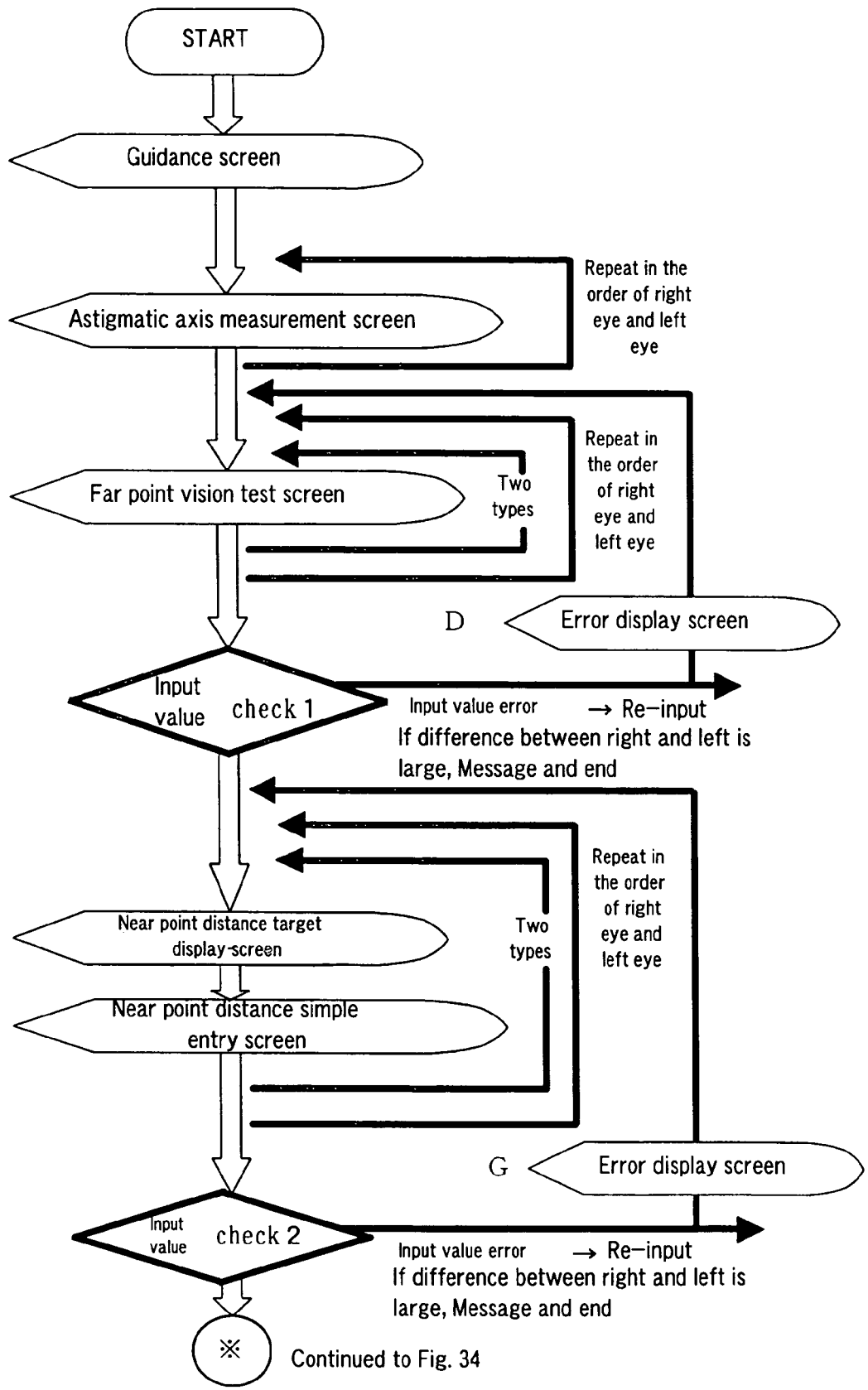
FIG. 34 is a flowchart of screens for lens power decision (No. 1)
Figure 35:
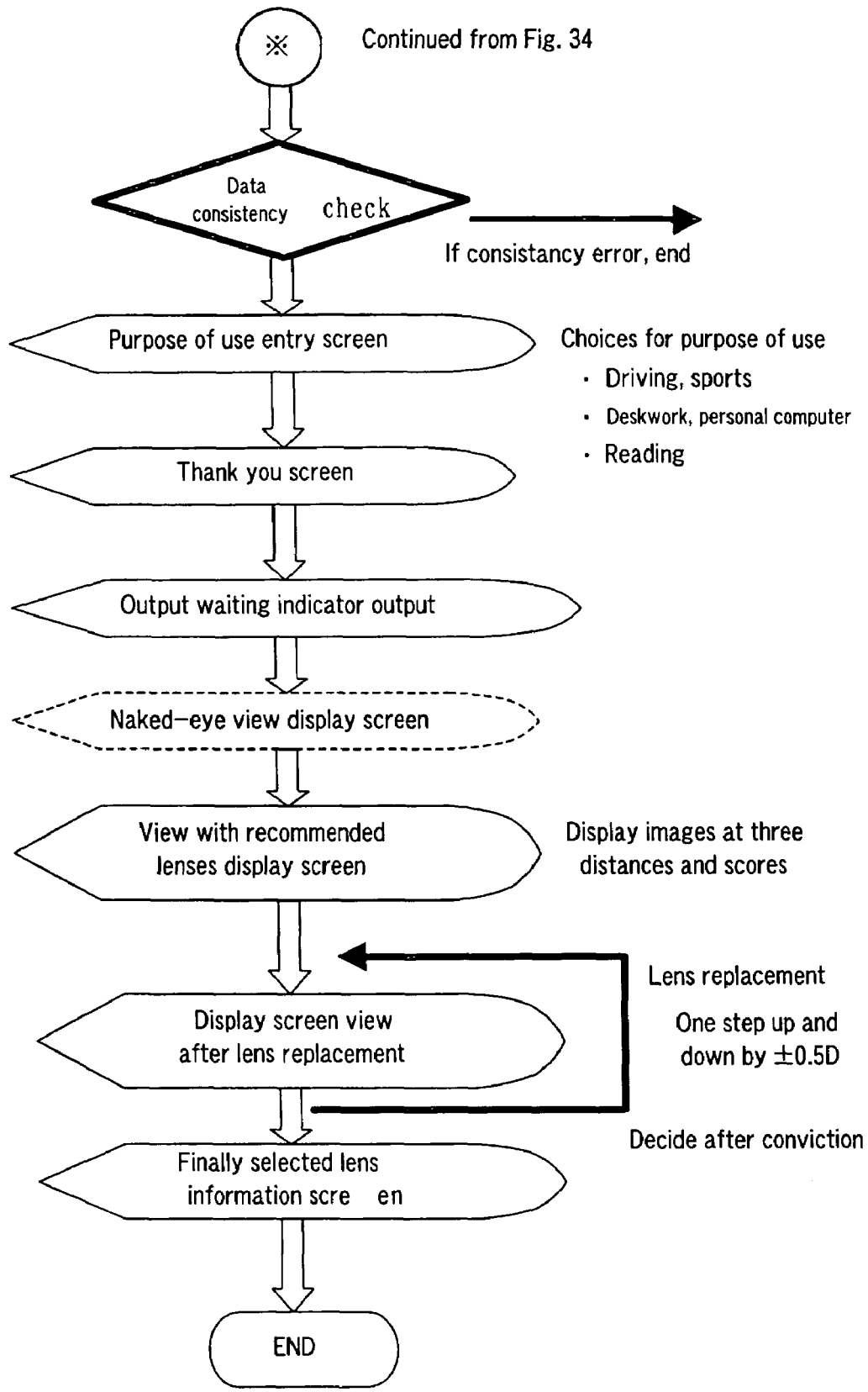
FIG. 35 is a flowchart of screens for lens power decision (No. 2)

Next, a method of testing vision by using this remote subjective vision test system will be described in accordance with a flow of FIGS. 34 and 35.

After the user client 4001 accesses the spectacle order/sales service center 4002 to complete the user authentication, a guidance screen is transmitted to the user client 4001 and displayed.

Next, a personal computer screen information collecting screen (FIG. 36) is transmitted to the user client 4001. On the personal computer screen information collecting screen, "Give us your personal computer information; necessary to get spectacles fitted to your eyes" is displayed so as to instruct the user to enter display information, such as the screen resolution. Then, "How long is this line in centimeters on your monitor screen?" so as to instruct the entry of size of the display.

Next, a user information entry screen (FIG. 37) is transmitted to the user client 4001. On the user information entry screen, the user is instructed to enter user information and data as information identifying the user. The user information includes base attributes such as a user code, a user identifier (ID), a user password, address, name, the date of birth, and telephone number, and data include the purpose of use, a near point distance, a far point distance, age, the previous lens power, vision of both eyes at the previous lens power, the balance of the right and left eyes at the previous lens power, how many years the previous spectacles are used, the type of contact lenses (if also used), desired corrected vision, and a disease related to vision. After the entry of the personal information, a wearing condition entry screen (FIG. 38) is transmitted to the user client 4001. As wearing conditions, the purpose of wearing spectacles or contact lenses (the situations in which he/she wants to wear them, for example, to see the area around his/her hands, to see objects in the distance and to drive a car and the like) or a visual environment (at which distance and in which area he/she often see objects in daily life, if she/he has much work on a personal computer as business activity, and other environmental information).

Next, an uncorrected vision test screen is transmitted to the user client 4001.

An uncorrected vision test is executed in the order of astigmatism axis measurement, a far point vision test, and a near point vision test. Although a measurement method of estimating a far point distance by the measurement at a certain distance (at a distance equal to a length of a human arm) is used in this preferred embodiment, a method of directly measuring a far point distance may also be used.

The astigmatism axis measurement is performed in the following procedure.

An astigmatism axis measurement step 1: First, a guidance screen is transmitted (FIG. 39) to display "Follow the following instructions. The right eye is measured. First, four zones hatched with parallel lines are displayed. Move about 1 m away from the screen and then come up to the position where you can clearly see the lines of any one of the four zones. Remove the spectacles or the contact lenses at this step. When watching a displayed target, cover your left eye with a hand so as not to touch the eye."

Figure 40:
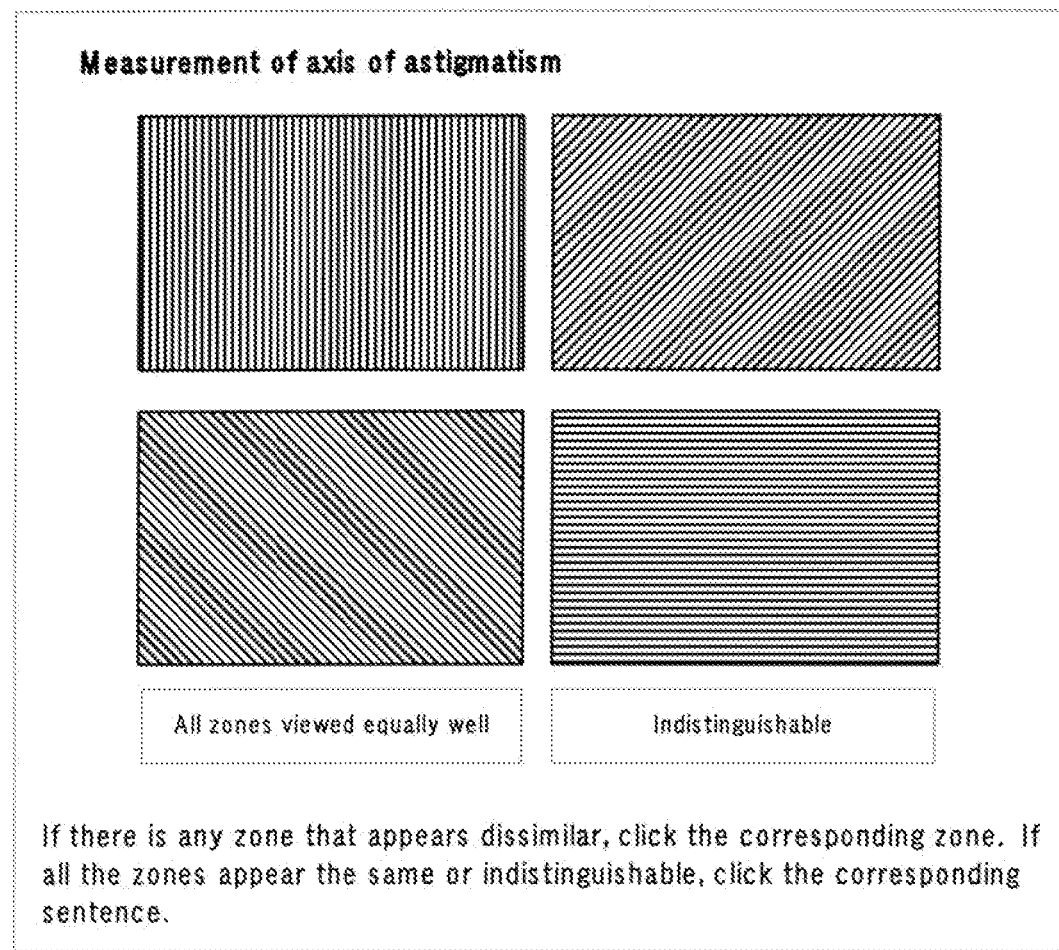
FIG. 40 is a schematic view of an astigmatism axis determination chart displayed at an astigmatism axis measurement step 2.

An astigmatism axis measurement step 2: Next, an astigmatism axis measurement screen is transmitted so as to display an astigmatism axis determination chart including four patterns on the screen (FIG. 40).

Figure 41:
FIG. 41 is a view showing a state of the user at an astigmatism axis measurement step 3.

An astigmatism axis measurement step 3: At this step, the user moves away about 1 m while covering the left eye with the left hand. At this time, the left eye is kept open. A state of the user at this step is shown in FIG. 41.

Figure 42:
FIG. 42 is a view showing a state of the user at an astigmatism axis measurement step 4.

An astigmatism axis measurement step 4: Next, the user brings his/her face gradually closer to the screen and stops at a distance allowing the distinction of four patterns. He/she should be careful not to be too close. A state of the user at this step is shown in FIG. 42.

An astigmatism axis measurement step 5: At this step, it is determined whether the four patterns in the drawing appear the same to the user or any one of them appears darker or brighter. An astigmatism axis measurement step 5-1: If "One of them appears dissimilar," the corresponding pattern is clicked. An astigmatism axis measurement step 5-2: If "All zones viewed equally well" or "Indistinguishable," the comment below the patterns is clicked.

An astigmatism axis measurement step 6: Subsequently, the right eye is covered with the right hand so as to execute the same process for the left eye.

An astigmatism axis determination chart includes linear groups in four directions, at 45 degrees, 90 degrees, 135 degrees, and 180 degrees, each having a plurality of parallel lines as shown in FIG. 40. If the subject is astigmatic, he/she has a clear view in a certain direction but the zone appears as if it were compressed and paled in another direction. Therefore, he/she is instructed to click the zone which appears dissimilar. The reason that the direction in which a view is different is selected is because the direction giving a clear view for an astigmatic may possibly be reversed at 90 degrees, depending on a distance to the object. Therefore, there is a possibility that the axis of astigmatism is erroneously determined if the direction giving a clear view is determined first. Accordingly, in preferred embodiments of the present invention, the principal axis of astigmatism is not determined yet at this step. At a later step of obtaining a far point distance, two far point distances calculated by targets in two directions are compared with each other such that the direction with a longer distance is determined as the principal axis.

Since the subject who is not astigmatic should principally have a uniform view in all the directions, the subject who clicks "All zones viewed equally well" or "Indistinguishable" is regarded as non-astigmatic so that the following measurement is performed only for horizontal and vertical principal axes.

In the case where a resolution of the determination of axis of astigmatism is desired to be enhanced, linear groups in four directions at intermediate angles between the respective four directions, that is, at 22.5 degrees, 67.5 degrees, 112.5 degrees, and 157.5 degrees may be added and displayed for selection.

Next, a far point distance is measured. Primarily, the far point distance measurement examines how far away from the screen the subject can be located while watching the screen in a comfortable manner. He/she stops at the farthest location at which he/she can see without blur (the position at which the screen starts to blur). A distance measured from the screen to the eye corresponds to a far point distance. However, since there is a limit in moving away from the personal computer, the far point distance is calculated by measuring a far point vision at a certain distance.

Figure 43:
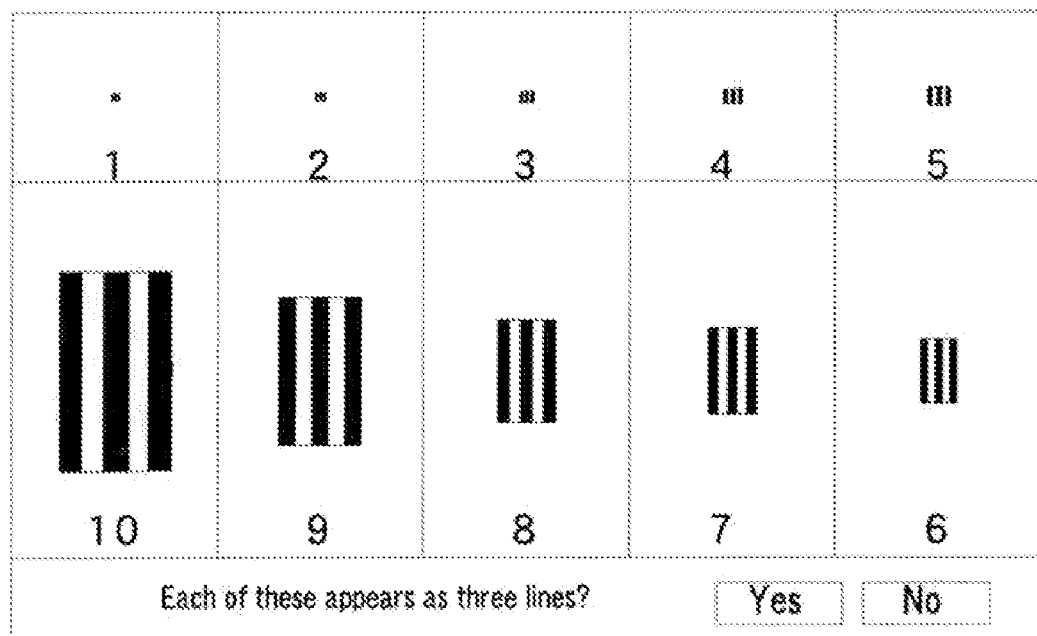
FIG. 43 is a schematic view of a far point distance measurement target displayed at a far point distance measurement step 1.

The far point vision is measured by determining the limit of size of an object that the user can see at a certain distance. The tar point vision in this preferred embodiment does not mean a generally used power unit such as 1.5 but another numerical unit. Hereinafter, the far point vision will be described in detail. The subject fully extends his/her arms while touching a display with fingers. He/she extends the arms with a straight posture. In this state, targets for measuring the far point vision are displayed on the display as shown in FIG. 43. The subject selects the smallest one of the displayed targets, of which three black lines he/she can clearly see. The number assigned to the target selected by the subject is determined as the far point vision. The far point distance is calculated from the far point vision based on the size of the target and the distance from the screen.

The far point vision is measured in the following procedure.

A far point distance measurement step 1: A far point distance measurement screen is transmitted on which far point distance measurement targets, each being different in size with three vertical lines, are displayed in a set (FIG. 43).

Figure 44:
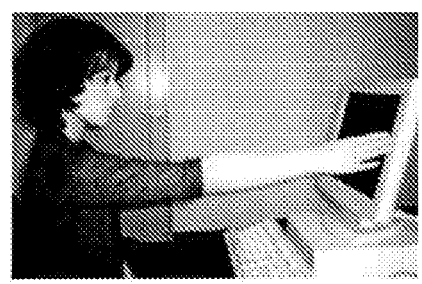
FIG. 44 is a view showing a state of the user at a far point distance measurement step 2.

A far point distance measurement step 2: At this step, the user touches the edge of the personal computer screen with the middle finger while fully extending the right arm to the fingertips. A state of the user at this step is shown in FIG. 44.

Figure 45:
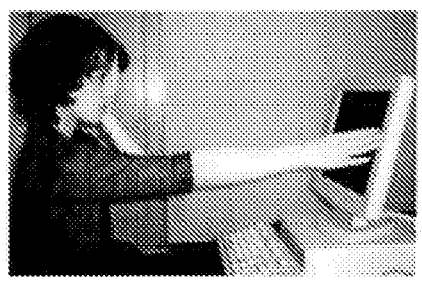
FIG. 45 is a view showing a state of the user at a far point distance measurement step 3.

A far point distance measurement step 3: Next, the user covers the left eye with the left hand so as to see the far point distance measurement targets with the right eye. A state of the user at this step is shown in FIG. 45.

Figure 46:
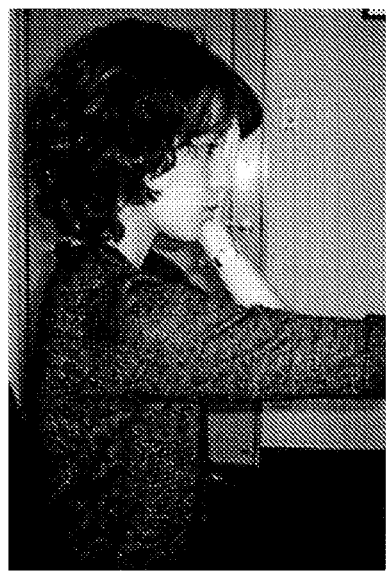
FIG. 46 is a view showing a state of the user at a far point distance measurement step 4.

A far point distance measurement step 4: Next, the user views a far point distance measurement chart displayed on the screen with a straight posture. A state of the user at this step is shown in FIG. 46.

A far point distance measurement step 5: At this step, it is determined whether the user can recognize three lines in the image or not. A state of the user at this step is shown in FIG. 47.

A far point distance measurement step 5-1: If the user cannot recognize three lines in any one of them, he/she clicks "YES."

If the user recognizes three lines (even in the case where they are "blurred"), he/she clicks "NO." The criterion of recognition of the three lines is, for example, shown in FIG. 48.

A far point distance measurement step 5-2: At this step, if the user answers "NO," the far point measurement targets are displayed in order of size so as to repeat a check until the image of which three lines are recognized appears.

A far point distance measurement step 6: Subsequently, the chart on the screen is changed to display far point distance measurement targets, each with three horizontal lines, so as to perform a measurement (not shown).

Figure 49:
FIG. 49 is a view showing a state of the user at a far point distance measurement step 7.

A far point distance measurement step 7: Similarly, the user sees the far point distance measurement targets with the right eye while covering the left eye with the left hand so as to carry out the same check. A state of the user at this step is shown in FIG. 49.

The check for the right eye is completed at this step.

A far point distance measurement step 8: Next, the left eye will be checked. As for the right eye, the user touches the edge of the personal computer screen with the middle finger while fully extending the left arm to the fingertips. He/she covers the right eye with the right hand to see the far point distance measurement targets with the left eye so as to carry out a check for the left eye in the same manner as for the right eye.

Although the far point distance is measured with the targets, each having three vertical lines, in the above description, the measurement is performed in the direction selected by the above-described astigmatism axis measurement and the direction perpendicularly crossing it. If the user is oblique astigmatic, the far point distance should be measured in two directions at 45 degrees and 135 degrees.

Although the screen, on which the targets of all sizes are combined, is first displayed such that the targets are then displayed in order of size in the above description, the present invention is not limited thereto. The targets may be individually displayed from the beginning. On the screen on which a plurality of targets are combined, the smallest target whose three lines can be recognized may be selected and clicked.

Next, a near point distance is measured. The near point distance measurement examines how close the subject can get to the screen while viewing the screen in a comfortable manner. He/she stops the face at the nearest position at which he/she can see without blur. A distance measured between the screen and the eyes corresponds to a near point distance.

The near point distance is measured in the following procedure.

Figure 50:
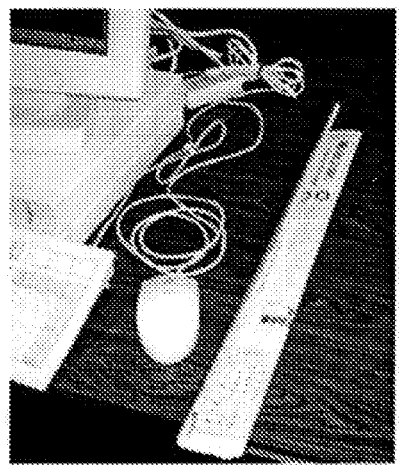
FIG. 50 is a preparatory state for executing a near point distance measurement.

The user folds a sheet of newspaper or copy paper in an elongated form (at a width of about 3 to 5 cm) and puts it beside the personal computer (FIG. 50).

Figure 51:
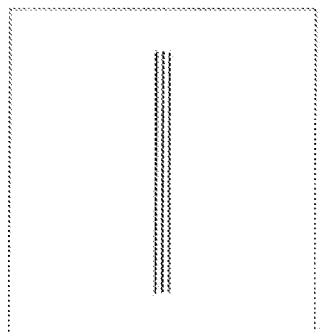
FIG. 51 is a schematic view of a near point distance measurement target displayed at a near point distance measurement step 1.

A near point distance measurement step 1: A near point distance measurement screen is transmitted so as to display a near point distance measurement target with three vertical lines on the screen (FIG. 51).

Figure 52A:
FIG. 52(A) is a view showing a state of the user at a near point distance measurement step 2.

A near point distance measurement step 2: At this step, the user moves his/her face as close to the screen as possible while covering the left eye with the left hand (FIG. 52(A)).

Figure 52B:
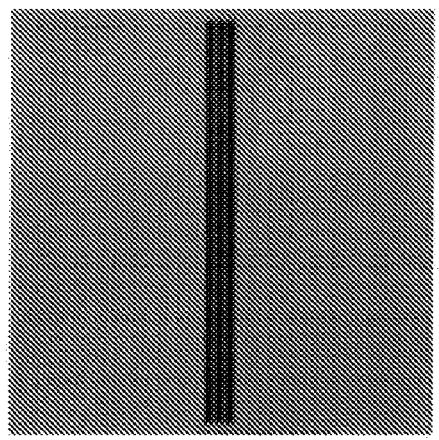
FIG. 52(B) is a view showing a state where a target is viewed with blur.

At this time, he/she verifies that the target is blurred. FIG. 52(B) shows a state where the near point distance measurement target is viewed as blurred.

Figure 53A:
FIG. 53(A) is a view showing a state of the user at a near point distance measurement step 3.
Figure 53B:
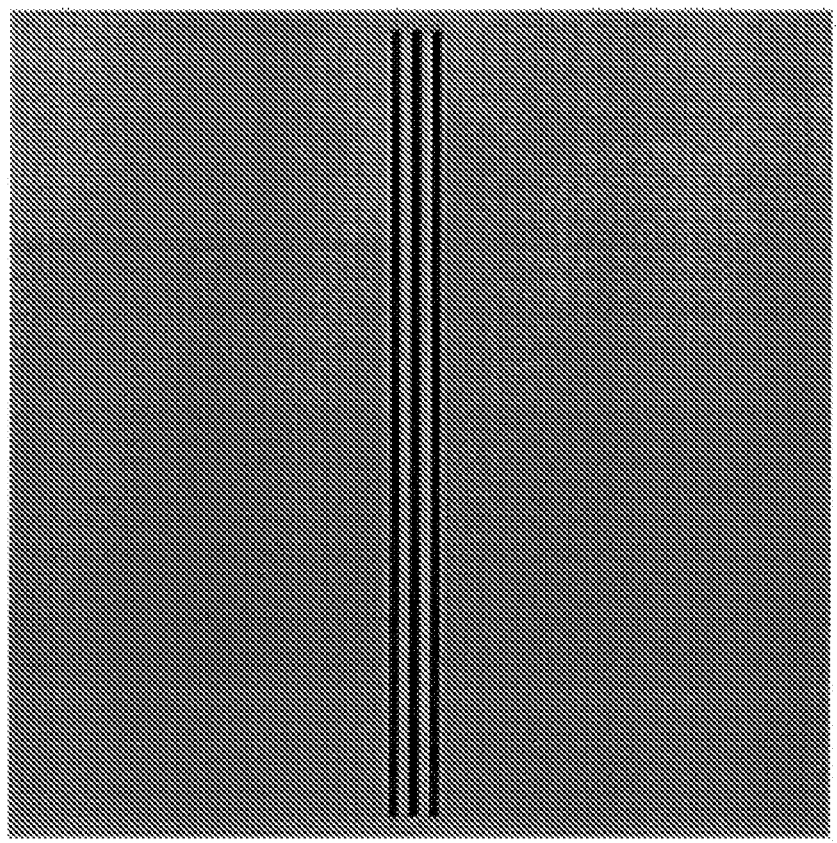
FIG. 53(B) is a view showing a state where a target is viewed clearly.

A near point distance measurement step 3: Next, the user moves his/her face away from the screen until he/she can recognize the three lines displayed on the screen (FIG. 53(A)). He/she should be careful that they may be recognized at the position extremely close to the screen in some cases. A state where the near point distance measurement target is clearly seen is shown in FIG. 53(B).

Figure 54:
FIG. 54 is a view showing a state of the user at a near point distance measurement step 4.

A near point distance measurement step 4: Next, he/she stops at the closest location at which he/she can recognize the target. Then, he/she rests his/her elbows on the desk and puts the folded paper on the temple. He/she marks the paper with the fingers at the eye corner area. A state of the user at this step is shown in FIG. 54.

Figure 55:
FIG. 55 is a view showing a state of the user at a near point distance measurement step 5.

A near point distance measurement step 5: Next, he/she puts the top of the folded paper perpendicularly to the screen without moving his/her face. A state of the user at this step is shown in FIG. 55.

A near point distance measurement step 6: Next, the paper is marked with the index finger of the left hand for the position of the right eye corner. After marking, the face may be moved.

Figure 56:
FIG. 56 is a view showing a state of the user at a near point distance measurement step 6.

A state at this step is shown in FIG. 56.

Figure 57:
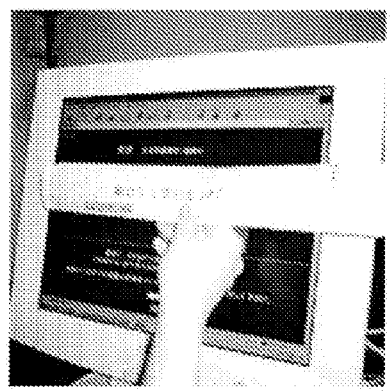
FIG. 57 is a view showing a state of the user at a near point distance measurement step 7.

A near point distance measurement step 7: At this step, the user presses a button "measure" on the upper left of the screen (FIG. 57).

Figure 58:
FIG. 58 is a view showing a state of the user at a near point distance measurement step 8.

A near point distance measurement step 8: The end of the paper is aligned with the position 0 of the "measure" appearing on the screen so as to measure a distance to the mark (FIG. 58). Three "measures" are displayed on the screen. If one measure is not sufficient, the paper is marked for the end of the measure and the remaining part is measured with the second one. If even two measures are not sufficient, the same operation is repeated for the third one.

Figure 59:
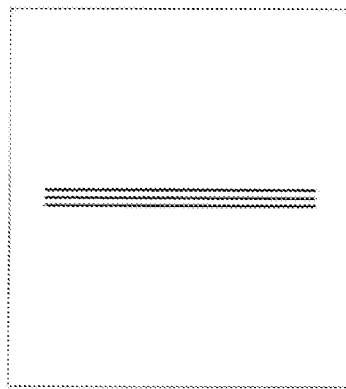
FIG. 59 is a schematic view of a near point distance measurement target displayed at a near point distance measurement step 9.

A near point distance measurement step 9: Once "Next" button is clicked, a near point distance measurement target with three horizontal lines is displayed on the screen (FIG. 59).

Figure 60:
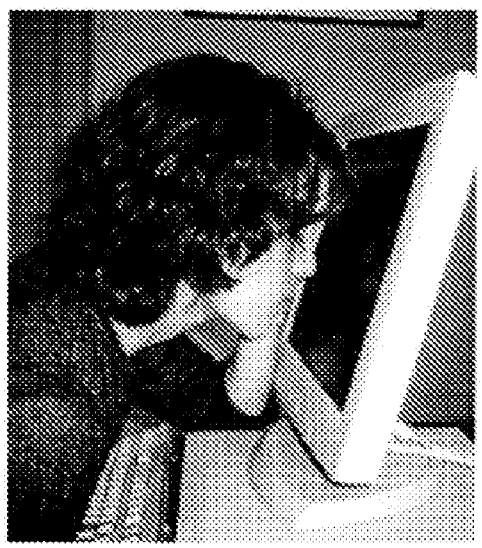
FIG. 60 is a view showing a state of the user at a near point distance measurement step 10.

A near point distance measurement step 10: The same check is carried out while the left eye is being covered with the left hand (FIG. 60).

A near point distance measurement step 11: When the length is measured, the check for the right eye is completed. Next, the left eye is checked in the same manner while the right eye is being covered with the right hand (not shown).

For the above-described near point distance measurement target, thin lines are used independently of vision of the subject.

Although the near point distance is measured for the target with three vertical lines and the target with three horizontal lines in the above description, the measurement is performed in the direction selected by the above-described astigmatism axis measurement and the direction perpendicularly crossing it. If the user is oblique astigmatic, the near point distance is measured in two directions at 45 degrees and 135 degrees.

The basic data measurement necessary for deciding a lens power is completed by the above operation. An eyeball optical model is constructed based on the basic data. In an eyeball optical model, an optical function of an eyeball within the range of accommodation of the user is detected so as to select a lens power. The selection of a lens power based on the eyeball optical model will be described in detail in a lens power deciding system described below.

Figure 61:
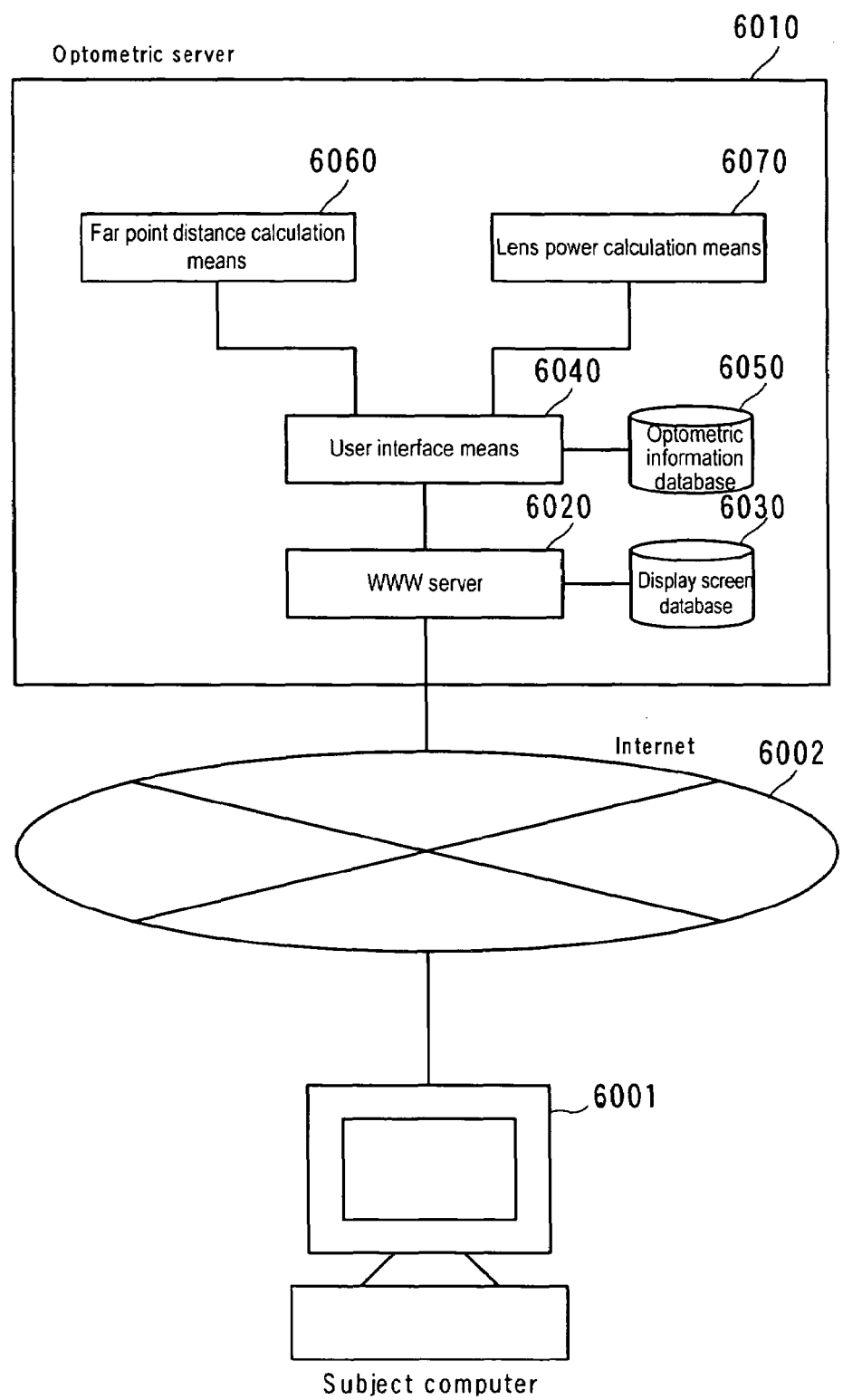
FIG. 61 is a diagram showing an example of a configuration of an optometry system equipped for the spectacle and contact lens selecting system according to a preferred embodiment of the present invention.

A second preferred embodiment of the lens power deciding step will be described by using an optometry system as shown in FIG. 61. As illustrated, in this optometry system, a computer 6001 used by the subject and an optometry server 6010 providing an optometry method of the present invention are also connected to each other through the Internet 6002.

The optometry server 6010 is for providing an optometry service to the subject computer 1, and includes a WWW server 6020, a display screen database 6030, user interface unit 6040, a subject database 6050, far point distance calculation unit 6060, and lens power calculation unit 6070.

The WWW server 6020 accepts access from the subject computer 6001 so as to provide an optometry function in accordance with an optometry procedure of the present invention. An HTTP server is used such that the subject computer 6001 can be accessed by a general-purpose Web browser.

The display screen database 6030 stores screen data that the WWW server 6020 presents to the accessed subject computer in accordance with the optometry procedure of the present invention. In this case, the first guidance screen, a subject's attribute entry screen, an astigmatism axis determination screen, a far point vision test screen, and a near point vision test screen are stored in an HTML format.

The user interface unit 6040 stores the attributes of the subject in the optometry information database 6050, activates the far point distance calculation unit 6060 to calculate a far point distance or activates the lens power calculation unit 6070 to calculate a lens power based on the information entered by the subject on the screen displayed by the WWW server 6020 on the subject computer 6001.

The user interface unit 6040 is activated from the WWW server 6020 by a CGI, whereas the far point distance calculation unit 6060 and the lens power calculation unit 6070 are activated from the user interface unit 6020. The optometry information database 6050 stores subject attribute data entered by the subject, selected direction data of the astigmatism axis determination chart(right and left eyes), visibility limit data based on the vision test chart (right and left eyes×two directions), near point distance data based on the near point distance measurement chart (right and left eyes×two directions), calculated far point distances (right and left eyes×two directions), and calculated lens powers (right and left eyes).

Figure 62:
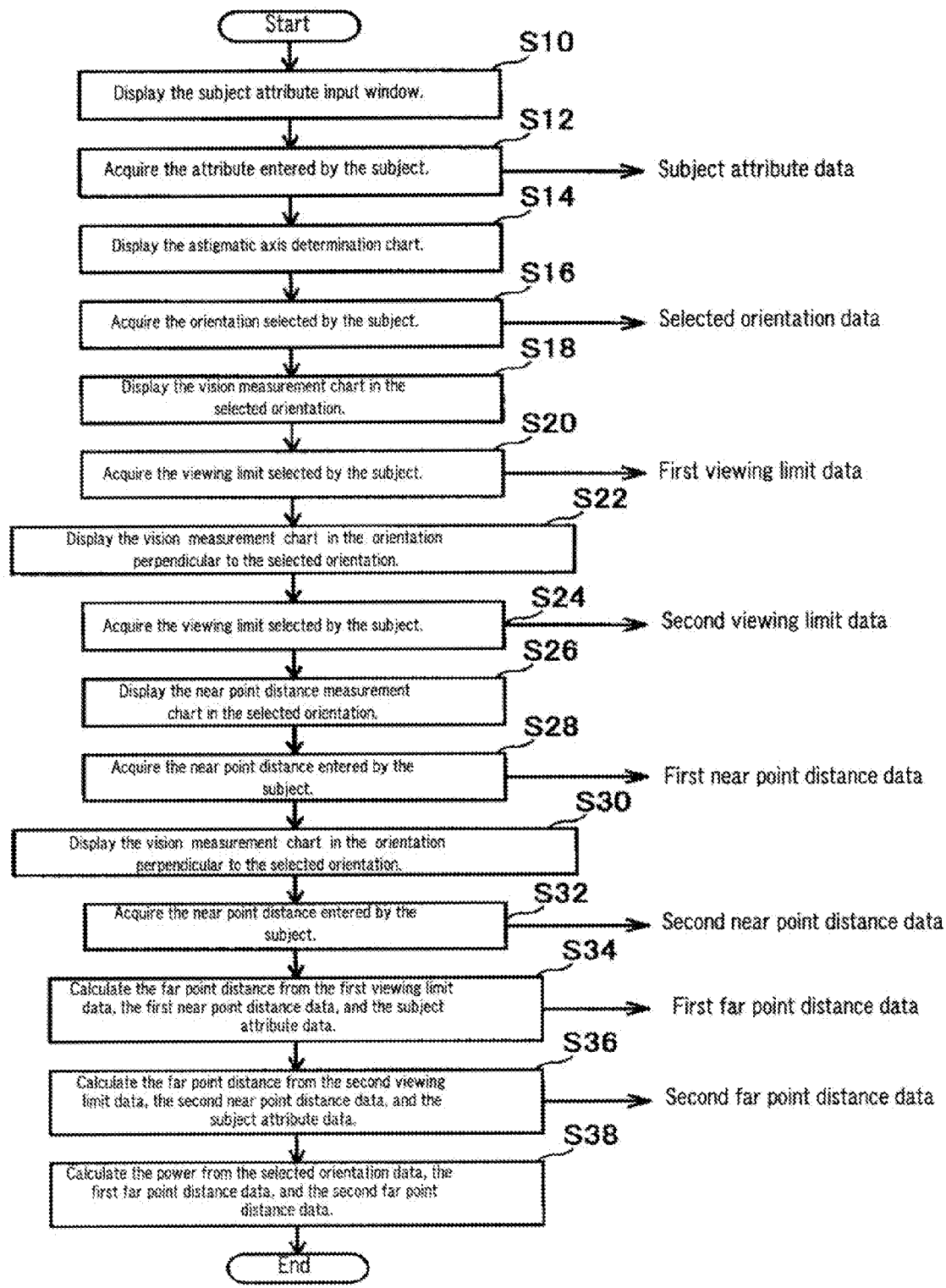
FIG. 62 is a view showing an example of a process flow of the optometry system.

Next, an example of a procedure of eye examination by such an optometry system will be described with reference to FIG. 62.

Figure 64:
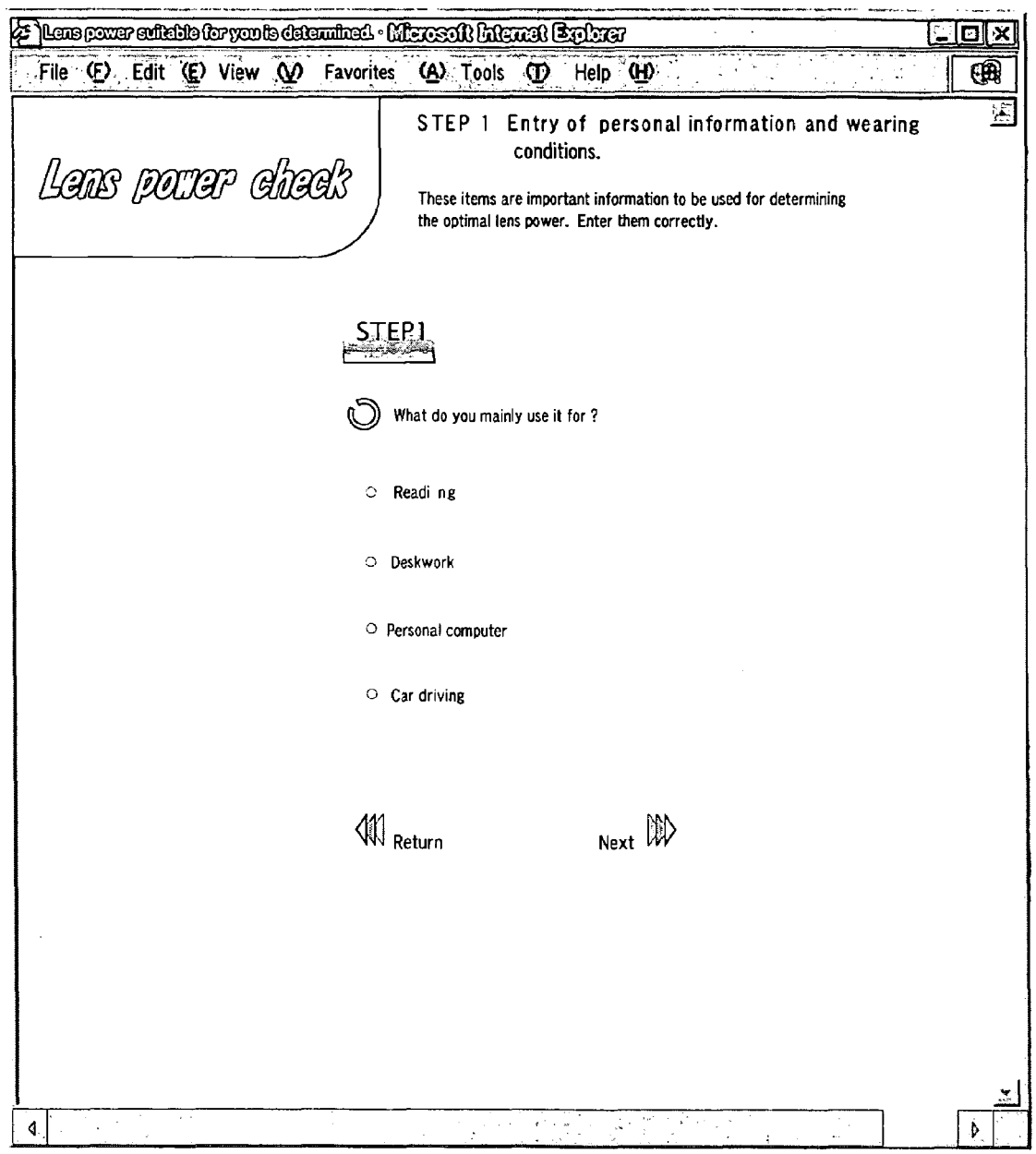
FIG. 64 is a view showing an example of display of a wearing condition entry screen.

First, the procedure displays a subject attribute input screen for acquiring the attributes of a subject (S10), and then acquires the attributes entered by the subject and stores them as the subject data (S12). The attributes of the subject include the personal information such as the age, the gender, and the height, and wearing condition information regarding the situation where the spectacles or the contact lenses are mainly used. FIG. 63 is an example of a display screen for acquiring personal information, and FIG. 64 is an example of a display screen for acquiring wearing conditions. Here, it is assumed that the "reading" in the wearing conditions is for near distances, the "deskwork" and "personal computer" for intermediate distances, and the "driving cars" for far distances.

Figure 65:
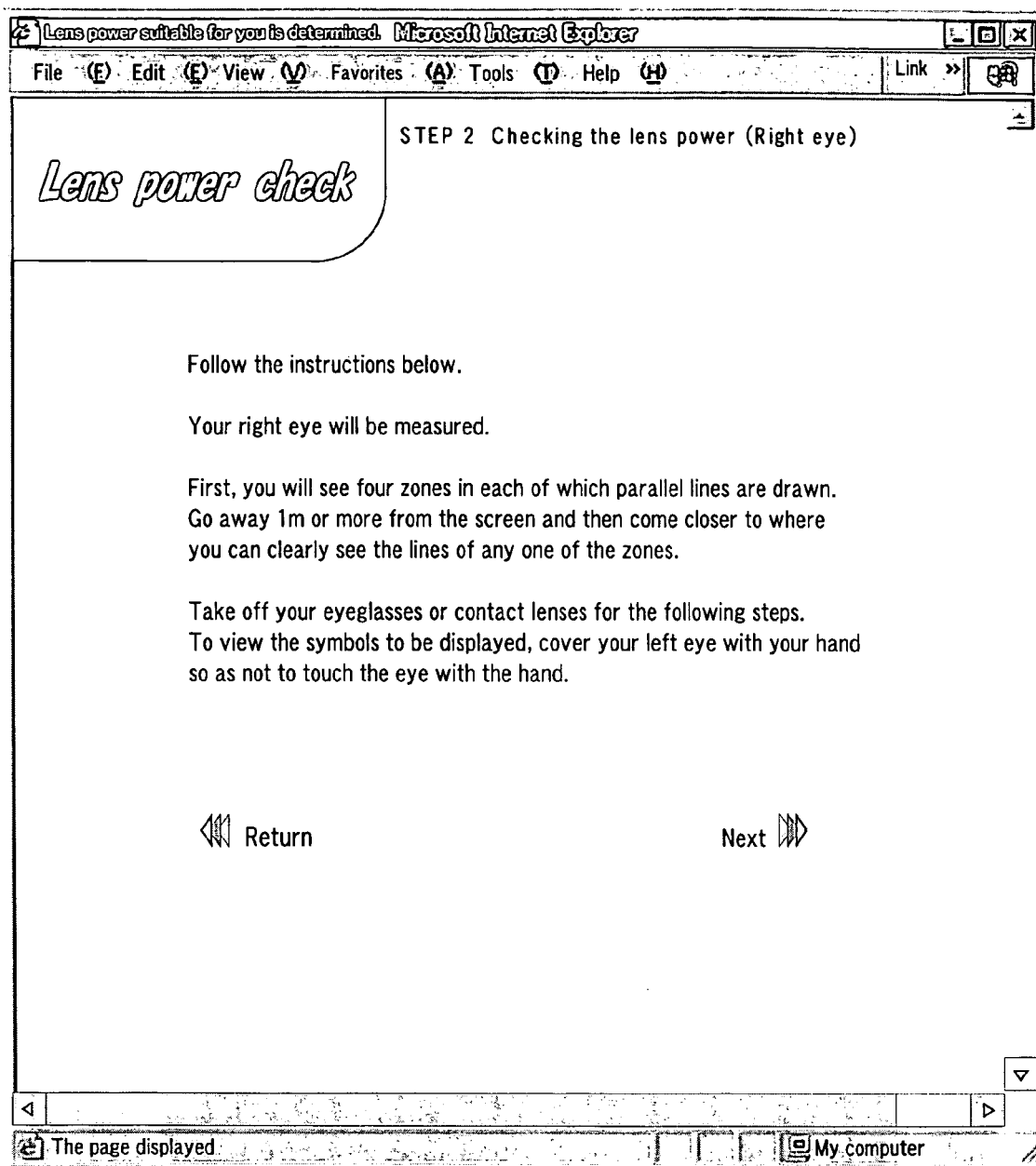
FIG. 65 is a view showing an example of display of an explanatory screen for astigmatism axis determination.
Figure 66:
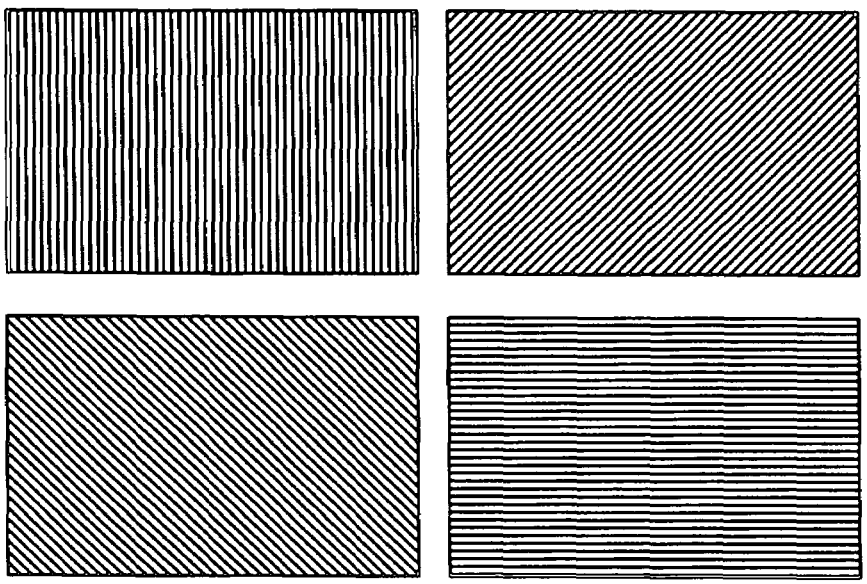
FIG. 66 is a view showing an example of display of an astigmatism axis determination screen.

Then, the procedure displays an astigmatic axis measurement chart for determining the astigmatic axis (S14) to acquire the orientation that the subject has selected and store it as selected orientation data (S16). FIG. 65 is an explanatory view illustrating an example of a screen for use with the astigmatic axis measurement, FIG. 66 showing an example of the astigmatic axis measurement screen.

As illustrated, the astigmatic axis measurement chart is made up of four groups of a plurality of parallel lines, each group having lines extended in one orientation at an angle of 45 degrees, 90 degrees, 135 degrees, and 180 degrees, respectively. A subject with astigmatism views the orientation which provides a sharper view and the orientations which provide a less-sharper blurry view, and is instructed to click on the zone in the orientation that provides a different view. The procedure instructs the subject to select the orientation that provides a different view as mentioned above. This is because astigmatism may possibly cause a 90 degree-inverted orientation to provide the sharper view depending on the distance to the object, and thus using the orientation that provides the sharper viewing at the first viewing would possibly cause an error in measurement of the astigmatic axis. Therefore, the present invention is designed not to determine the main axis of the astigmatic axis at this stage but to determine the orientation that is longer in distance as the main axis by comparing the two far point distances calculated using the targets in two orientations at the later stage where a far point distance is calculated.

In principle, a subject without astigmatism is probably provided with the same view in all the orientations. Thus, the subject who clicks on "All are viewed in the same way" or "Indistinguishable" is considered to have no astigmatism and undergoes the following measurements only on the horizontal and vertical main axes.

The astigmatic axis measurement chart has a green background and black lines, with the width of the lines being two pixels and the width between the lines being three pixels. A background color of white causes a miosis and a greater depth of field in the eyes due to its excessive brightness, thus causing a problem of providing reduced difference in the viewing of the four zones. This is why the eye-friendly green base color is used to reduce brightness. Black was used as the color of the lines because a number of subjects who underwent an eye examination experiment determined consequently that black could be easily viewed. The width of the lines is at least two pixels because particularly in the case of a CRT display, one pixel may provide a different viewing between the horizontal/vertical and the diagonal direction due to the occurrence of focus blurring caused by the electron gun. The width between the lines was set such that the spacing between the lines could be recognized from a distance of 1 m because an extremely short distance to the chart in the astigmatism measurement would invert the astigmatic axis by 90 degrees, possibly resulting in an error in the measurement. A vision of 1.0 (an angle of view of 0.1 degrees) indicates the capability of distinguishing a slit of 0.29 mm at a distance of 1 m, which generally corresponds to one pixel on a 14-inch liquid crystal display or a 17-inch CRT. Therefore, two pixels correspond to a vision of about 0.5. However, since those who take the eye test need spectacles, the spacing was further expanded to three pixels.

On the other hand, the four orientations were provided for the astigmatic axis because of the following reasons. That is, this makes it possible to select sufficiently practical spectacles or contact lenses even using the four orientations, and the determination needs to be made as easily as possible without any error because the subject makes the determination by himself or herself.

Figure 67:
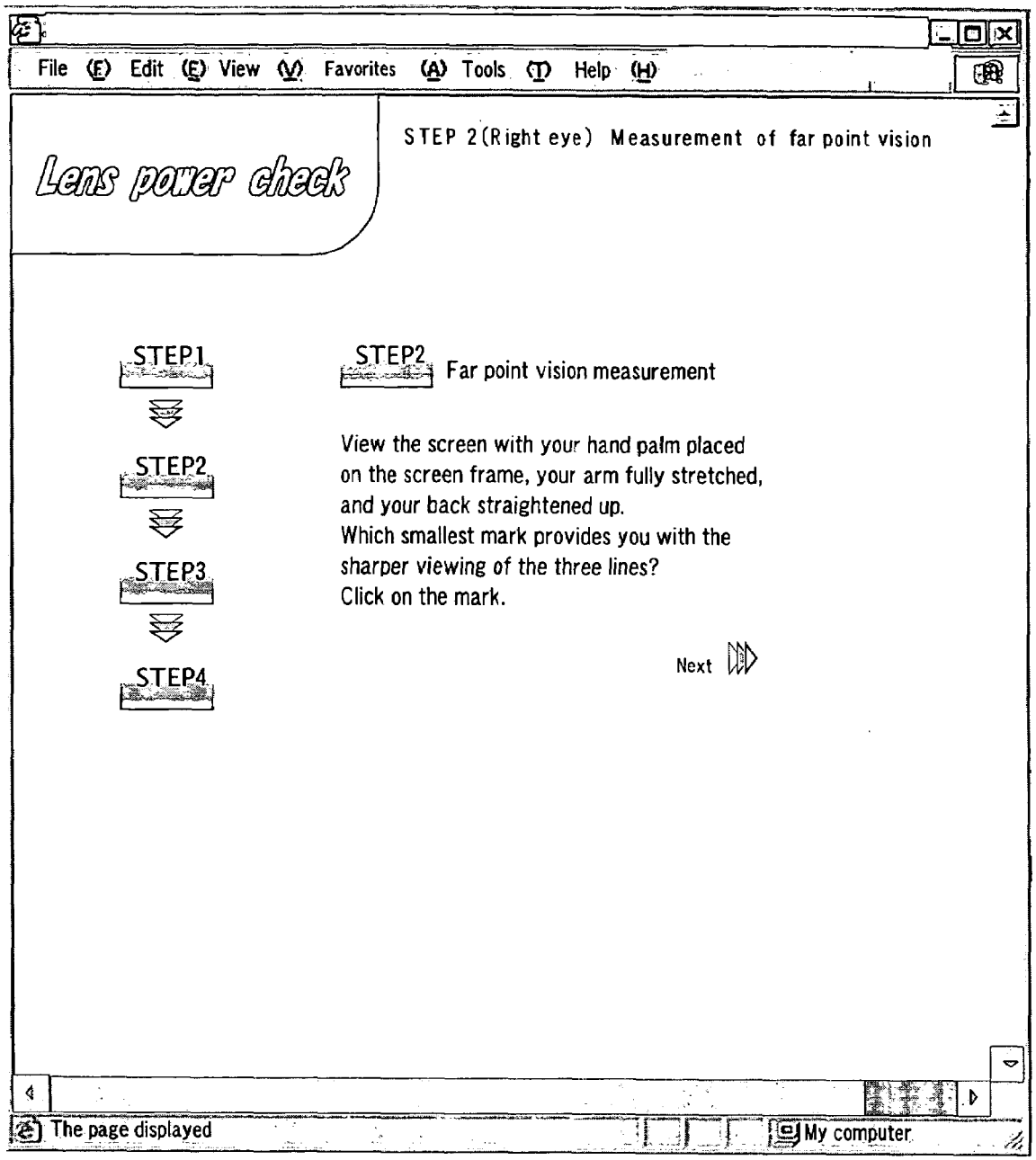
FIG. 67 is a view showing an example of display of an explanatory screen of a far point vision test.

Then, to measure the far point vision in the selected orientation that has been selected by the subject, the procedure displays the vision measurement chart for the selected orientation (S18) to acquire the viewing limit selected by the subject, which is then stored as first viewing limit data (S20). FIG. 67 is an explanatory view illustrating an example of a screen for a far point vision measurement, FIG. 68 showing an example of the far point vision measurement screen.

As illustrated, the vision measurement chart is a light and dark line image made up of three black lines and two white lines of a certain line width, a plurality of the charts being displayed in each of which the width of the lines are varied in I steps (from about 10 steps to 20 steps) corresponding to vision. On the vision measurement charts, the subject is instructed to click on the smallest mark that the subject can distinguish the three lines. Since the subject is permitted to select the mark that provides the viewing of three lines as described above, the subject can make a determination more easily as compared to the Landoldt ring that is viewed to visually distinguish a single gap.

The subject is instructed to measure the far point vision at a reach from the computer screen. This is because the length of the arm is proportional in length to the height, and thus the distance between the subject and the chart can be predicted in accordance with the data on the height entered in advance.

As described above, the measurement can be conveniently carried out because the subject does not need to measure the distance to the computer screen or adjust the screen display size.

Likewise, to measure the far point vision in the orientation perpendicular to the orientation selected by the subject, the procedure displays the vision measurement chart in the orientation perpendicular to the selected orientation (S22), and the viewing limit selected by the subject is acquired and stored as second viewing limit data (S24).

Figure 69:
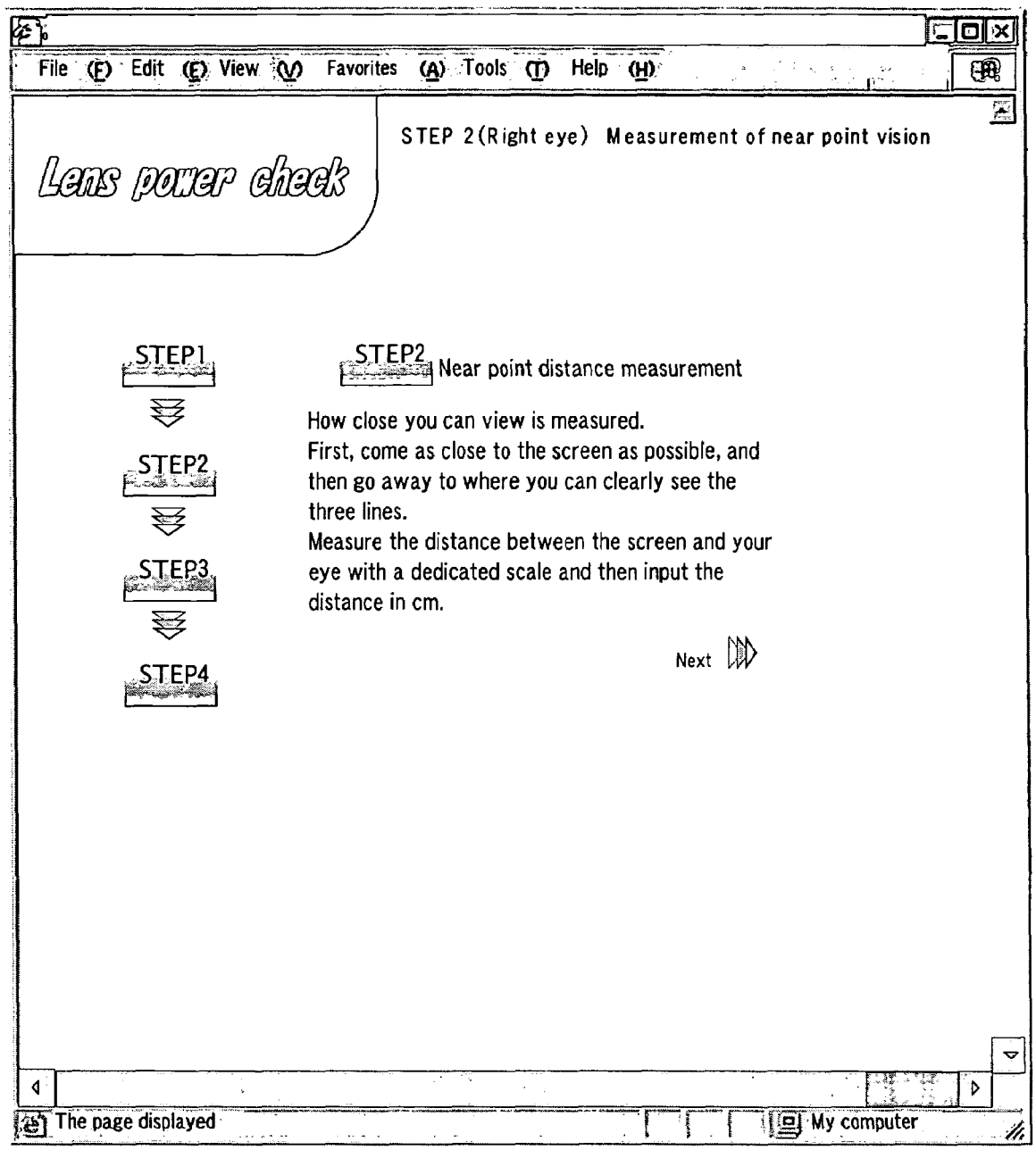
FIG. 69 is a view showing an example of display of an explanatory screen of near point distance measurement.
Figure 70:
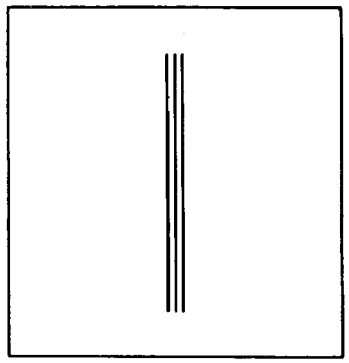
FIG. 70 is a view showing an example of a near point distance measurement screen.

Then, to measure the near point distance in the orientation selected by the subject, the procedure displays a near point distance measurement chart in the selected orientation (S26) to store the near point distance entered by the subject as the first near point distance data (S28). FIG. 69 is an explanatory view illustrating an example of a screen for a near point distance measurement, FIG. 70 shows an example of the near point measurement screen.

As illustrated, the near point distance measurement chart has three black lines provided on a green background. The message on the screen instructs first the subject to move as close to the screen as possible and then move away therefrom to a position at which the subject can clearly see the three lines and measures the distance between the eyes and the screen, thereafter instructing the subject to input the distance in centimeters.

The near point distance measurement chart uses thinner lines as compared to the aforementioned vision measurement chart regardless of vision of a subject, because the chart is viewed in close proximity to the computer screen. However, because of the difference in resolution due to age, thin lines are used for youths and slightly bolder lines are used for middle-aged and elderly people.

To measure the near point distance in the orientation perpendicular to the selected orientation selected by the subject, the procedure displays a near point distance measurement chart in the selected orientation (S30) to store the near point distance entered by the subject as the second near point distance data (S32).

Then, the procedure determines the far point distance from the first viewing limit data, the first near point distance data, and the subject limit data to store the resulting distance as the first far point distance data (S34). Likewise, the procedure determines the far point distance from the second viewing limit data, the second near point distance data, and the subject limit data to store the resulting distance as the second far point distance data (S36).

Figure 71:
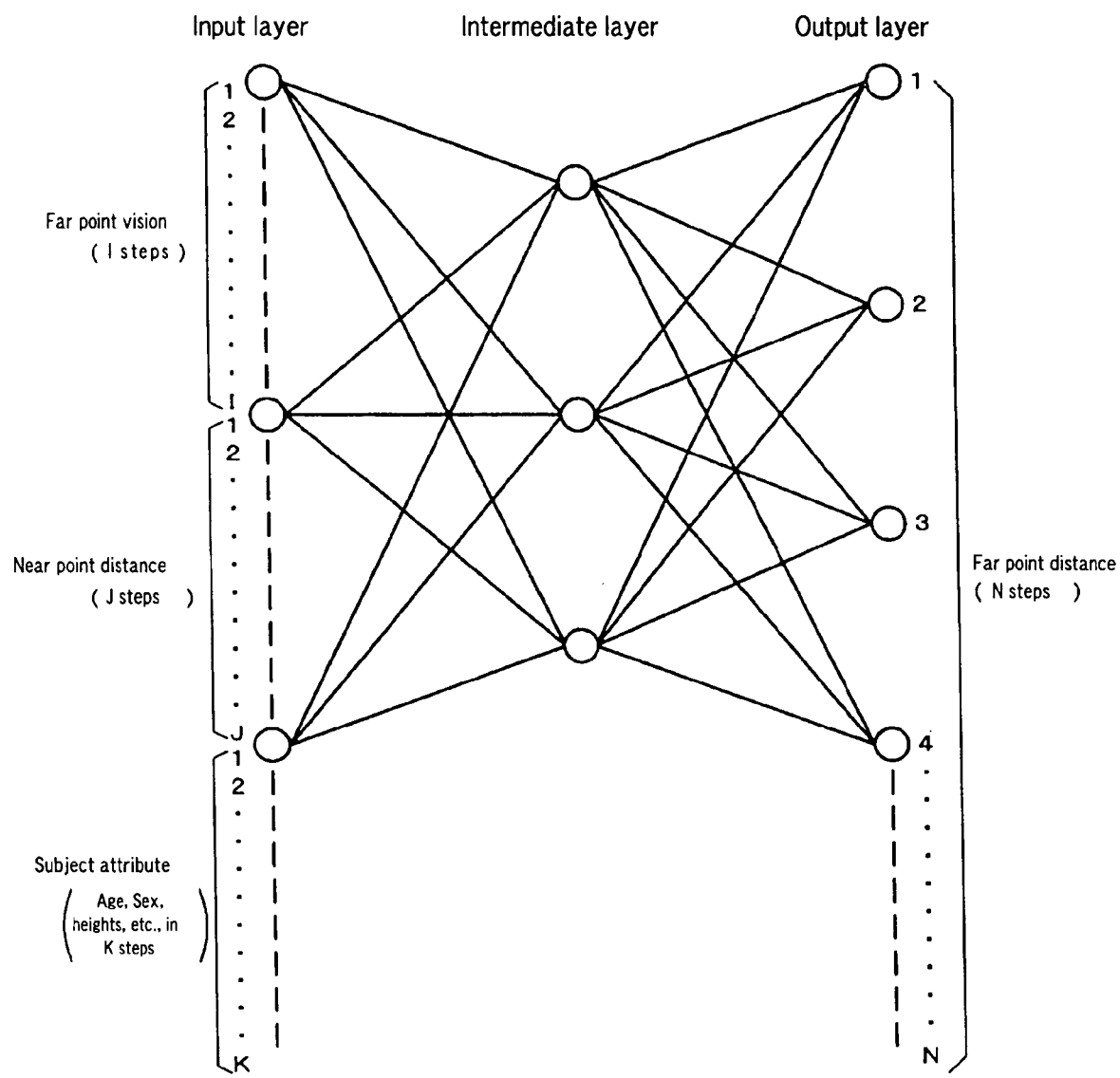
FIG. 71 is a view showing an example of a configuration of a neural network for far point distance calculation.

The far point distance is measured using a neural network which a number of subjects have taught in advance. FIG. 71 is a view illustrating an exemplary configuration of a neural network for operating the far point distance. As illustrated, the input layer has I steps of far point vision (the viewing limit selected by the subject on the vision measurement chart), J steps of near point distance (the near point distance measured by the subject on the near point distance measurement chart), and K steps of subject attributes (the age, the gender, and the height), while the output layer has N steps of far point distance. The age and gender are used as parameters because the accommodation ability of the eyes of the subject varies depending upon age and gender. The height, as described above, which is proportional to the length of the arm, is used as a substitute parameter in order to adjust the distance between the subject and the screen to the length of the arm. As the method of learning, the back-propagation method is used. However, the method is not limited thereto.

Here, to make the conversion into the lens power easier, the near point distance of the input parameters and the far point distance resulted from the operation are each converted to the value D (diopter) or the reciprocal of the distance measured in meters.

The neural network was designed to produce two independent learning models in the selected orientation of the astigmatic axis and the orientation perpendicular to the selected orientation to perform calculations for each of them separately.

Since different types of displays provide different ways of viewing the screens, the operation was performed using neural networks that had been separately taught depending upon the display being either a liquid crystal display or a CRT.

The astigmatic axis determination (S14) through the far point distance calculation (S36) described above are performed for both eyes, right and left eyes, so as to calculate diopters (S: spherical diopter, C: cylindrical diopter and AX: axis of astigmatism) from the obtained selected direction data, the first far point distance data, and the second far point distance data (S38).

Assuming that the first far point distance obtained at S34 is D1, its direction is AX1, the second far point distance obtained at S3$\epsilon$ is D2 and its direction is AX2, when $|D1|<|D2|$, S=D1, C=D2−D1, AX=AX1, and when $|D2|<|D1|$, S=D2, C=D1−D2, AX=AX2.

Although the case where a diopter of the eye is merely calculated is described in the above-described preferred embodiment, a diopter of a lens may be determined from the obtained diopter of the eye and the wearing conditions in the subject attribute data so as to accept an order of spectacles or contact lenses.

In this case, based on the wearing condition in the subject attribute data, a distance for which the spectacles or contact lenses are normally used is determined from any one of short-distance use (30 cm), intermediate-distance use (50 to 60 cm) and long-distance use (5 m) so as to determine a diopter of a recommended lens.

For example, for long-distance use, the far point distance D1 is corrected to be 5 m (−0.2 D). Therefore, a diopter of a recommended lens is D1+0.2 D.

An eyeball optical model generating unit for generating an eyeball optical model based on the lens power calculated by the lens power calculation unit and the attributes of the subject and a naked eye focal performance confirmation unit for confirming focal performance of a naked eye by using the generated eyeball optical model may be provided so as to check the validity of the calculated lens power. As a result, a lens power can be determined with higher accuracy.

Moreover, a post-correction focal performance calculation unit for calculating focal performance after vision correction with a recommended lens by using the generated eyeball optical model may be provided so as to determine the recommended lens. As a result, a lens power more suitable for the subject may be provided.

Furthermore, a sharpness score calculation unit for calculating a sharpness score at a predetermined distance from a focal state with the recommended lens, an image sample generating unit for generating an image sample at the calculated sharpness score, and an image sample display unit for displaying the generated image sample on the computer screen are provided such that the subject confirms the image sample with the recommended lens on. As a result, since the subject can check how well he/she can see with the lenses on, a more suitable a lens power is provided.

Although the far point distance calculation unit using a neural network that learns from a large number of subjects to obtain the far point distance from the far point vision, the near point distance, and the attributes of the subject is described, the present invention is not limited thereto. The far point distance may be calculated by using a fuzzy inference so as to obtain a membership function or an inference rule from the data of a large number of subjects. Moreover, from the data of a large number of subjects, the relationship between the far point vision and the far point distance may be obtained as an approximate formula including the near point distance and the attributes of the subject as parameters so as to be used to calculate the far point distance. In this manner, the advantages of the present invention can be obtained.

Although the near point distance serves as an input parameter in the calculation of the far point distance in the above-described preferred embodiment, the present invention is not limited thereto. The near point distance may be omitted. In this case, since the near point distance is proportional to the age, the advantages of the present invention can also be obtained.

Although it is described that the linear groups in four directions, each including a plurality of parallel lines, are displayed on one screen in the astigmatism axis determination chart such that the subject selects the zone that appears dissimilar in the above-described preferred embodiment, the present invention is not limited thereto. The linear groups in four directions may be individually displayed in a sequential manner so as to select the direction in which the zone appears dissimilar.

Although a plurality of charts, each being different in size, are arranged and displayed on one screen in the vision test chart such that the subject selects the limit of visibility in the above-described preferred embodiment, the present invention is not limited thereto. The charts in the respective sizes may be displayed in size order such that the limit of visibility is chosen by the subject.

Although the images of the selected direction in the astigmatism axis determination and the direction perpendicularly crossing it are displayed on the computer screen for the display of the vision test chart and the near point distance measurement chart in the above-described preferred embodiment, the present invention is not limited thereto. The images of four directions may be stored in the display screen database 6030 in advance such that the image is selected therefrom for display. Alternatively, image data for a specific direction may be stored, whereas the images of the other directions may be generated by rotating the image with a graphic tool based on the direction data. Moreover, graphic data of the image to be displayed may be stored such that the images are drawn and generated by a drawing tool based on the direction data. As described above, by using a method of generating images by a graphic tool, a load on the image display is increased. However, since an image in an arbitrary direction can be generated, a direction of the axis of astigmatism may be determined more accurately.

Similarly, for the display of a plurality of charts with varied line widths in the far point vision test, image data with a specific line width may be enlarged and reduced by a graphic tool or may be drawn and generated by a graphic tool.

Although it is described that the display size of the astigmatism axis determination chart, the vision test chart, and the near point measurement chart on the screen is not particularly changed by the computer settings in the above-described preferred embodiment, the present invention is not limited thereto. In order to obtain a lens power with higher accuracy, the screen settings of the computer may be acquired so as to change the display size of the screen based on them. The screen settings of the computer to be obtained are the type and the size of a display, the resolution settings of a computer, and other relevant parameters. They may be automatically obtained from property information of the computer or may be input as the subject attribute data.

As described above, images may also be enlarged or reduced by a graphic tool or may be drawn by a drawing tool in this case.

Furthermore, although it is described that an experimentally determined optimal color is used as a display color of the astigmatism axis determination chart, the vision test chart, or the near point distance measurement chart in the above-described preferred embodiment, the present invention is not limited thereto. A display color selecting function may be provided.

For example, color samples may be displayed in advance to the subject such that the subject can select the color that he/she likes, or a predefined color may be automatically selected by screen settings of the computer display.

Also for a display color of each of the charts, a plurality of display color patterns may be stored in advance such that a selection can be made therefrom. It is apparent that an image in a specific display color pattern may be color-converted by a graphic tool or may be drawn by a drawing tool.

Similarly, although it is described that an experimentally defined optimal brightness is used for a brightness of a background or a segment of the astigmatism axis determination chart, the vision test chart, and the near point measurement chart in the above-described preferred embodiment, the present invention is not limited thereto. A display brightness selecting function may be provided.

Also for a display brightness of each of the charts, a plurality of display brightness patterns may be stored in advance such that a selection can be made therefrom. It is apparent that an image in a specific display brightness pattern may be brightness-converted by a graphic tool or may be drawn by a drawing tool.

Although it is described that the attribute data of the subject is acquired each time the subject receives an optometry service in the above-described preferred embodiment, the present invention is not limited thereto. It is apparent that the attribute data may be pre-stored as a customer database such that necessary data is extracted from the database. As described above, the customer database is provided so as to store a history of the optometry services provided thus far and data of sold spectacles and contact lenses in addition to the subject attribute data described above. As a result, more accurate optometry in accordance with the characteristics of the subject can be performed so as to provide more accurate corrective lenses.

It is described that the eye examination is carried out primarily for short-sighted persons who are also astigmatic in the above-described preferred embodiment. However, since the near point distance is obtained in addition to the far point distance in this preferred embodiment, the eye examination may also be used for subjects who are farsighted or presbyopic.

More specifically, if the far point distance is extremely long and the near point distance is also long, there is a possibility that he/she may be farsighted or presbyopic. If the accommodation ability of eyes of the subject is obtained, the determination of farsightedness or presbyopia can be made based on it.

Therefore, for example, the age or gender of the subject is used as a substitute parameter for the accommodation ability of eyes. A neural network, which uses the far point distance, the near point distance, and the attributes of the subject (age and gender) as inputs and outputs the diopter of astigmatism and the diopter of long-sightedness, is made to learn a large number of subjects who are farsighted or presbyopic. By using it, the diopter of farsightedness or presbyopia may also be calculated.

Moreover, the accommodation ability of eyes of the subject may be actively measured by using a computer screen so as to determine the diopter of farsightedness or presbyopia based on it. For this determination, for example, a method of measuring the tracking ability of an image traveling on the computer screen, measuring the visibility when the subject moves changing a distance with the computer screen in a rapid cycle is conceivable. In this manner, not only short-sighted persons who are also astigmatic but also subjects who are farsighted or presbyopic may use the system. Therefore, an optometry system for everybody is obtained.

According to preferred embodiments of the present invention, the attributes of the subject are obtained. In addition, the astigmatic axis determination chart is displayed on the computer screen so as to obtain the direction selected by the subject. The vision test chart is displayed for the obtained direction and the direction perpendicularly crossing it so as to obtain the limit of visibility selected by the subject. The far point distances are calculated from the obtained limit of visibility and the obtained attributes of the subject so as to calculate the lens power from the obtained direction and two calculated far point distances. Therefore, the present invention is effective in that the subjects who are astigmatic can be dealt with and the eye examination can be performed in a simple manner by using the computer screen without requiring any special equipment.

Figure 72:
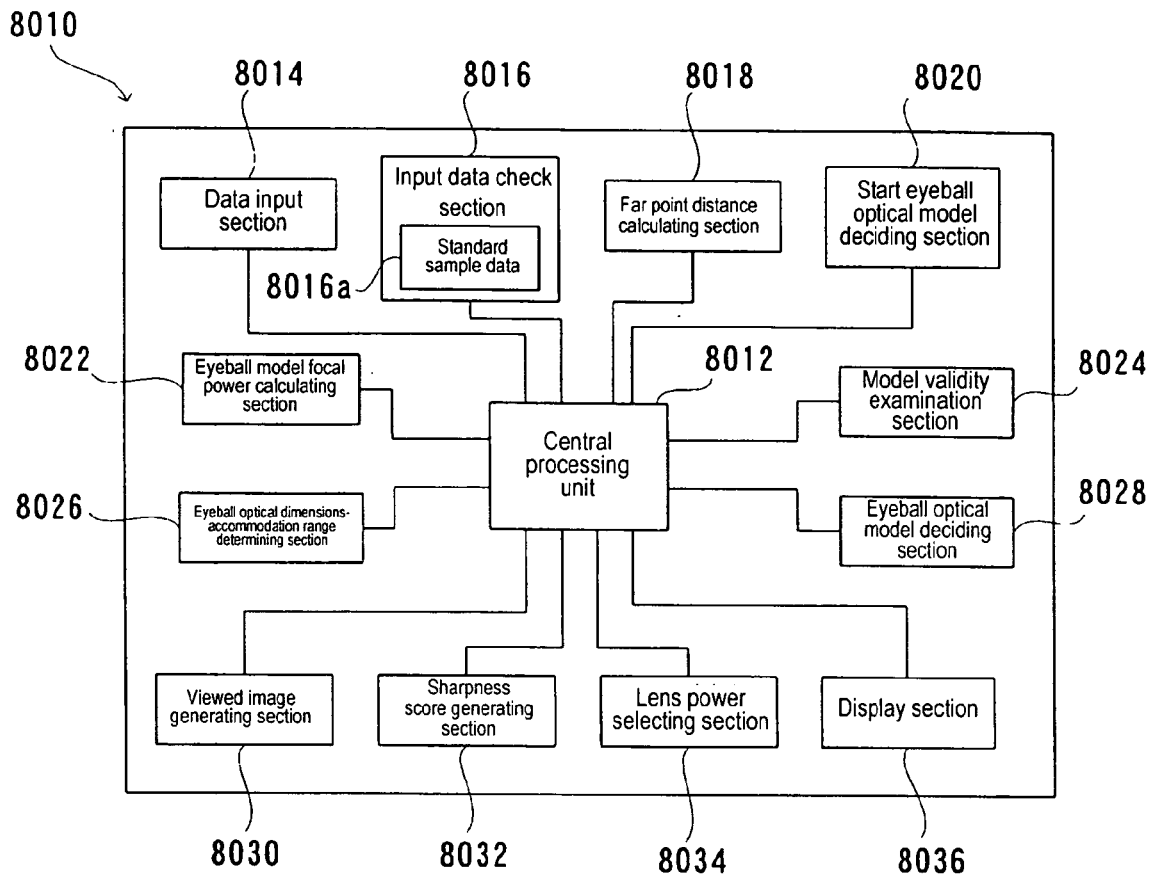
FIG. 72 is a view showing an example of a configuration of a lens power decision system equipped for the spectacle and contact lens selecting system according to a preferred embodiment of the present invention.

Next, a third preferred embodiment of the lens power deciding step described above will be described by using a lens power deciding system shown in FIG. 72. The lens power deciding system is for constructing an optical model of an eyeball of the user to decide a power of a corrective lens, and includes a central processing unit 8012. The central processing unit 8012 controls the operations of: a data input section 8014; an input data check section 8016; a far point distance calculating section 8018; a start eyeball optical model deciding section 8020; an eyeball optical model focal performance calculating section 8022; a model validity examining section 8024; an eyeball optical dimensions-accommodation range determining section 8026; an eyeball optical model deciding section 8028; a viewed image generating section 8030; a sharpness score generating section 8032; and a display section 8036. Hereinafter, the schema of each of the sections controlled by a central control unit 12 will be described.

The data input section 8014 is for inputting the age of a person who wants to wear corrective lenses, such as spectacles or contact lenses, the conditions of use of the corrective lenses, the axis of astigmatism, the far point vision, and the near point distance. The data input section 8014 includes equipment such as a keyboard, a mouse, or a touch panel to which a person directly inputs data or equipment configured to be able to receive data through a network by using a modem or a LAN card, and a program for controlling the equipment.

Figure 73:
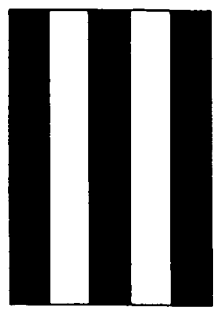
FIG. 73 includes schematic views, each showing a target for testing a far point vision where (a) shows the largest target, (b) shows a medium-sized target, and (c) is the smallest target.
Figure 73:
Figure 73:

The far point vision in this preferred embodiment does not mean a generally used power unit such as 1.5, but rather, another numerical unit. Hereinafter, the far point vision will be described in detail. On a display such as a computer, targets as shown in FIG. 73 are displayed. The subject fully extends his/her arms while touching a display with fingers. He/she fully extends the arms with the straight posture. In this state, the targets for measuring vision are sequentially displayed in the order of size on the display as shown in FIGS. 73(*a*) to 73(*c*). The subject selects the smallest one of the displayed targets, of which black three lines can be clearly seen. The number assigned to the target selected by the subject is determined as the far point vision. The far point distance is calculated from the far point vision.

The input data check section 8016 checks the consistency of the input value from a value of the data input to the data input section 8014. The input data check section 8016 stores therein a large amount of stored standard sample data 8016a in which data of the axis of astigmatism, the far point distance, and the near point distance are associated with each other on the basis of age. The input data check section 8016 determines whether a value of the data input to the data input section 8014 is valid as a result of comparison with the standard sample data 16a.

The far point distance calculating section 8018 calculates the far point distance from the far point vision corresponding to the data input to the data input section 8014. The far point distance calculating section 8018 stores data related to age, gender, height, far point vision, and the near point distance. Based on the input data of age, gender, height, far point vision, and near point distance, the far point distance calculating section 18 calculates the best far point distance that is the most suitable to the data.

The start eyeball optical model deciding section 8020 decides a start eyeball optical model based on the age of the subject and the approximated lens power.

Figure 74:
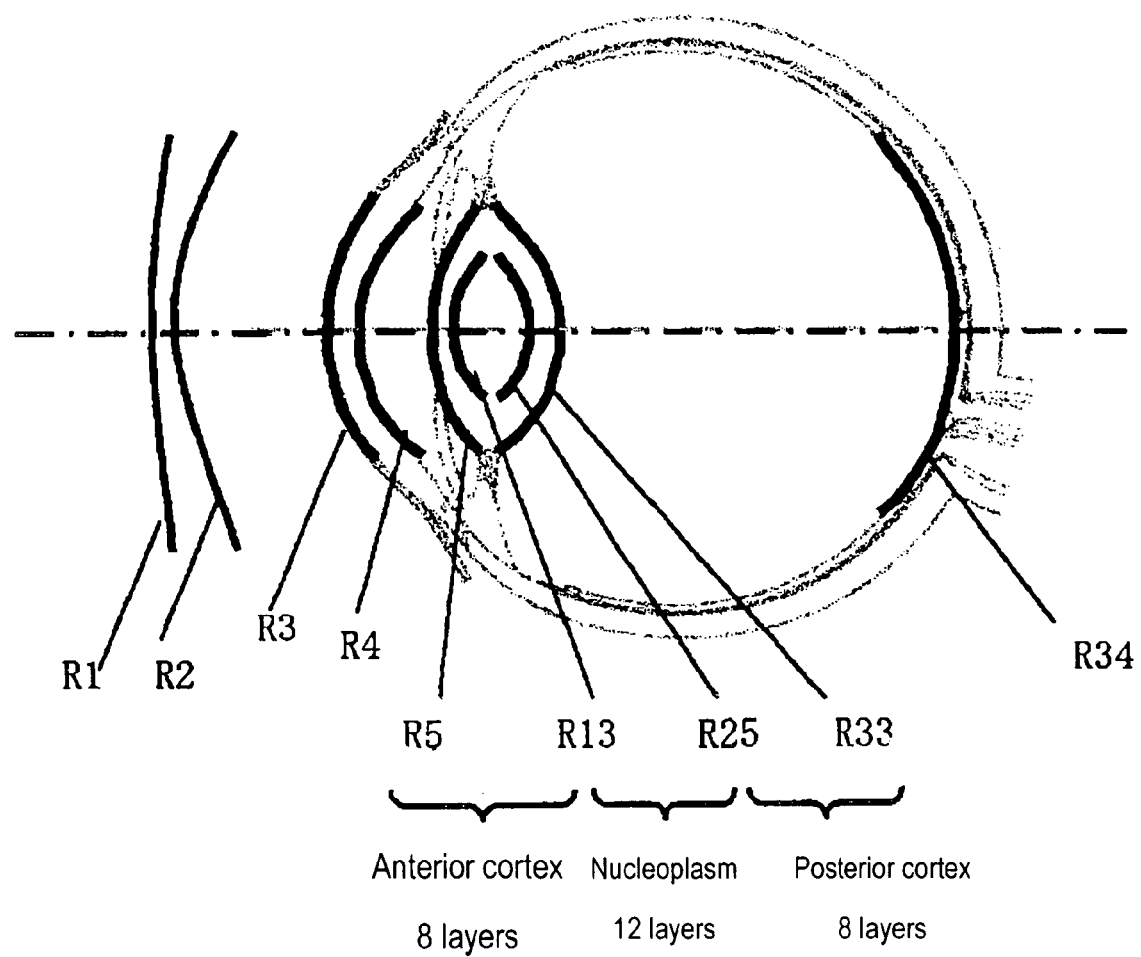
FIG. 74 is a schematic view showing an eyeball optical model.

Now, the eyeball optical model will be explained below. In the eyeball optical model, light-beam refractive elements of a human eye, as shown in FIG. 74, are configured as a mathematical/physical numerical model of a lens. As shown in FIG. 74, the eyeball optical model includes light-ray refractive elements of the eyeball such as the cornea, the anterior chamber, the lens of the eye, the vitreous body, and the retina. An eyeball optical model is constructed with respect to these light-beam refractive elements in accordance with the following optical dimensions.

Cornea: the radius of curvature R3 of the front surface, the thickness, the refractive index, and the radius of curvature R4 of the rear surface Anterior chamber: the thickness and the refractive index Lens of the eye: the radius of curvature of anterior cortex (the radii of curvature R5, R6, R7, R8, R9, and R12) and the thickness of the anterior cortex; the radius of curvature of nucleoplasm (the radii of curvature R13, R14, R15, R16, R17, R18, R19, R20, R21, R22, R23, R24) and the thickness of the nucleoplasm; and the radius of curvature of posterior cortex (the radii of curvature R25, R26, R27, R28, R29, R30, R31, R32, and R33) and the thickness of the posterior cortex and their respective refractive indices Vitreous body: the refractive index and the thickness Retina: Radius of curvature R34

The aforementioned optical dimensions are different from each other depending on the age and the accommodation ability of the eye of each individual. However, in this preferred embodiment, an eyeball optical model is pre-constructed as a standard pattern with reference to values from living body measurement data on Japanese people. For example, regarding the anterior chamber, Depth of anterior chamber: the depth of anterior chamber is 3.66 mm for the ages of 8-15, 3.71 mm for the ages of 16-30, 3.5 mm for the ages of 31-51, 3.18 mm for the ages of 51-77.

Length of the eye axis: the length of the eye axis shows a tendency contrary to the aging tendency of the depth of anterior chamber.

Lens of the eye: there is uneven distribution of refractive indices. The refractive index of the surface is irrelevant to age, but the refractive index of the nucleus of the lens of the eye increases a little by aging. The weight of thickness increased by aging is 174 mg for the ages of 20-39, 204 mg for the ages of 40-59, and 266 mg for the ages of 80-99.

Although the eyeball optical model is constructed based on the aforementioned values in this preferred embodiment, the eyeball optical model may also be constructed based on the values listed in the literature data. The following is an example of literature data applicable to the construction of an eyeball optical model.

(i) Concerning the Depth of the Anterior Chamber

According to "Study on the depth of anterior chamber" by Katsuo Aizawa, Japanese Ophthalmologic Society Journal Vol. 62, No. 11 (1958), the relationship between the depth of the anterior chamber and the age varies as follows:

3.66 mm for ages from 8 to 15, 3.71 mm for ages from 16 to 30, 3.51 mm for ages from 31 to 51, and 3.18 mm for ages from 51 to 77.

That is, the study indicates that the depth of the anterior chamber tends to gradually increase as the body grows from the youth and reach the maximum level when the body has grown up, and thereafter, gradually decrease as the body deteriorates.

(ii) Concerning the Length of the Eye Axis

According to "Study No. 1 on the essence of shortsightedness" by Tsutomu Sato, et al, Japanese Ophthalmologic Society Journal Vol. 63, No. 7 (1959), for the low degree of shortsightedness, the length of the eye axis gradually increases as the degree of myopia increases, showing a strong correlation therebetween.

(iii) Concerning the Weight of the Lens of the Eye

According to "The eye" by Davson Hugh (1909) and Graham L. T. Jr., New York; London Academic Press, the weight of the lens of the eye only increases with advancing age as follows:

174 mg for ages from 20 to 39, 204 mg for ages from 40 to 59, and 266 mg for ages from 80 to 99.

(iv) Concerning the Thickness and Diameter of the Lens of the Eye

According to Complete Collection of New Clinical Ophthalmology 3A, by Hiroshi Ichikawa, et al, 1993, KANEHARA & CO., LTD, the thickness and diameter of the lens of the eye increases with advancing age.

The eyeball optical model that has been pre-constructed by applying the aforementioned values is used as the start eyeball optical model determined by the start eyeball optical model deciding section 8020. The start eyeball optical model is not constructed for the combinations of all ages and approximate lens powers, but with attention being given to the fact that the start eyeball optical model has common eye characteristics for the same age and approximate lens power, such an eyeball optical model is pre-constructed to have a median value in each age class represented on the vertical axis and a median value in each approximate lens power class represented on the horizontal axis. The vertical axis representing M classes and the horizontal axis representing N classes allow for constructing M by N start eyeball optical models. That is, a table is used in which the vertical axis represents the age class (e.g., at five year intervals up to twenty years of age, and at 10 year intervals for 20 years of age or more) and the horizontal axis represents the approximate lens power (e.g., at intervals of 1.0 D). With this table, such a start eyeball optical model is pre-constructed for a combination of median values in each class (e.g., the 35 years of age and the lens power of the amount of correction required being −2.5 D).

Although M×N eyeball optical models are constructed as start eyeball optical models and the start eyeball optical model deciding section 8020 uses the eyeball optical model having the closest value as a start eyeball optical model among them in this preferred embodiment, it is not limited thereto. A start eyeball optical model may be constructed from the values of the constructed eyeball optical models based on the most suitable value of a light-beam refractive element from the measured age and approximated lens power.

The start eyeball optical model determined in the start eyeball optical model deciding section 8020 is used as an initial value in the eyeball optical model deciding section 8028 described below to perform an optical system design automation process for constructing an eyeball optical model that is accurate for the person. In this start eyeball optical model, the design automation process is terminated within a short time, and therefore, the processing time is reduced as compared with an optical system design automation process using an independent start eyeball optical model which is not based on the age or the approximated lens power. Moreover, the reliability of solutions (optical dimensions enabling the best focal state) is improved.

The eyeball optical model focal performance calculating section 8022 calculates focal performance of the eyeball optical model in a naked eye state of the subject or with corrective lenses. As a state of the eyeball for calculating a focal state, a state at the near point or the position within the range of accommodation ability in the vicinity of the near point, a state at the far point or the position within the range of accommodation ability in the vicinity of the far point, or a state at the position away from the near point and the far point is used.

The model validity examining section 8024 examines the validity of the eyeball optical model at the limit of accommodation on the near point side and/or on the far point side based on the focal performance calculated by the eyeball optical model focal performance calculating section 8022.

The eyeball optical dimensions-accommodation range determining section 8026 determines the range of accommodation of the eyeball at an accommodation midpoint from the input near point distance and the calculated far point distance. Furthermore, the eyeball optical dimensions-accommodation range determining section 8026 is configured to generate an image of the eyeball optical model in which the range of accommodation of the eyeball at the accommodation midpoint is determined.

The eyeball optical model deciding section 8028 adjusts the values of the optical dimensions of the start eyeball optical model such that the focal state in the eyeball of the subject at the midpoint of accommodation calculated from the near point distance and the far point distance of the subject is optimal, thereby determining the eyeball optical model that corresponds to a state of the eye of each person.

The viewed image generating section 8030 generates visual images viewed by the subject before and/or after the correction by unit of a corrective lens based on the result calculated in the eyeball optical model focal performance calculating section.

The sharpness score generating section 8032 derives the sharpness score that indicates mathematically the degree of sharpness of viewing by the subject before and/or after the correction by unit of a corrective lens.

The sharpness score indicates how sharply an image is viewed in an arbitrary numerical value and is calculated, for example, such that the higher numerical value indicates that the image is more sharply seen.

The lens power selecting section 8034 examines optical performance when the subject wears spectacles or contact lenses to select a lens power.

The display section 8036 is a display device for confirming an operating condition of a corrective lens deciding server 8010 or for confirming a value of the data input by the subject or the calculated data. As the display section 8036, a display connected to the computer or a display of the computer connected to the corrective lens deciding server 8010 via the data input section 8014 is used.

Figure 75:
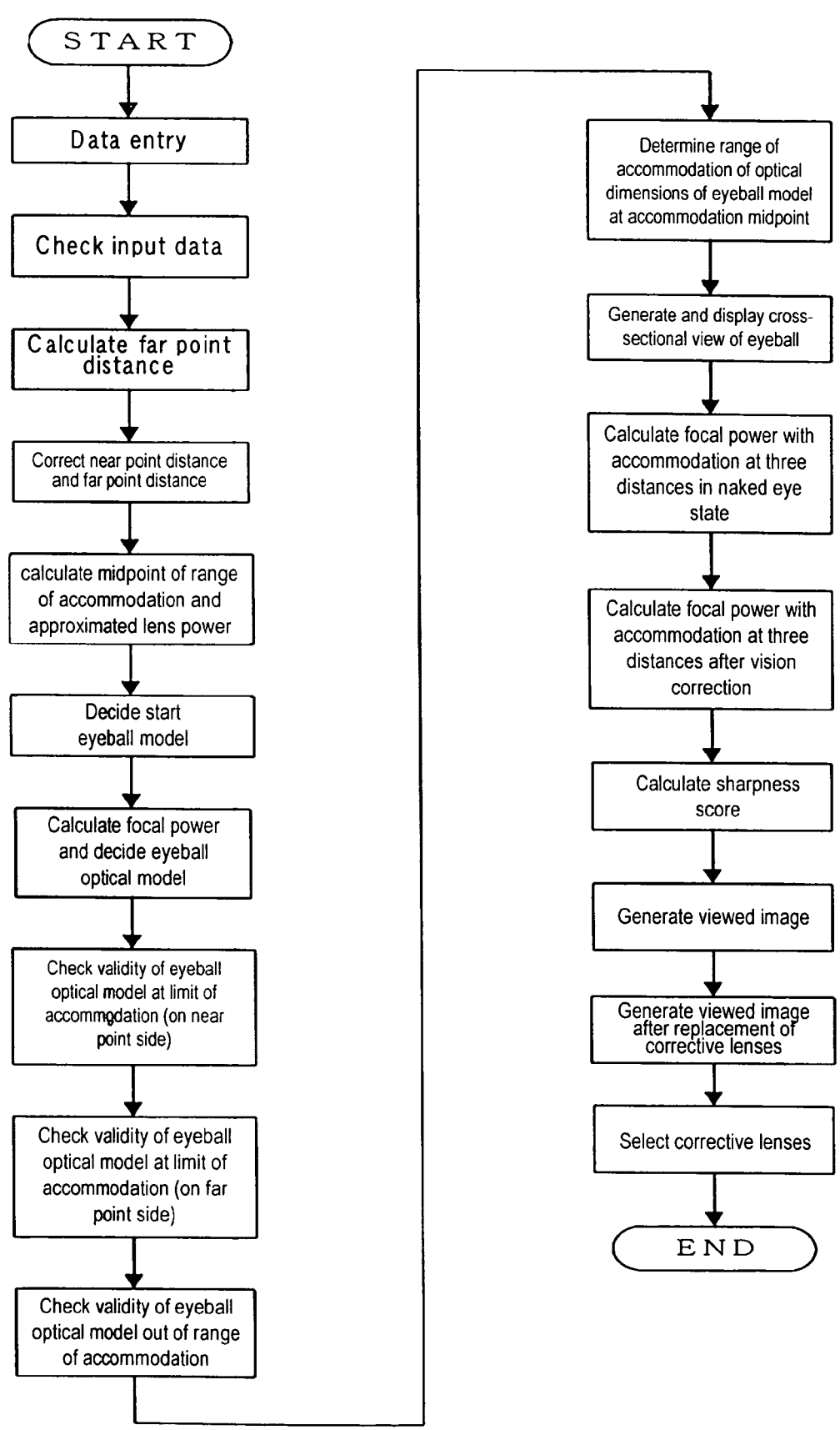
FIG. 75 is a flowchart showing an operation of a corrective lens deciding server according to a preferred embodiment of the present invention.

Next, an operation of the present invention will be described with reference to FIG. 75.

(1) The gender, the age, the axis of astigmatism, the near point distance, the far point vision, and the conditions of use of corrective lenses (for reading, deskwork, driving, and the like) of the subject are input by using the data input section 8014.

(2) The input data is examined by the input data check section 8016.

(3) The far point distance is calculated from the far point vision by the far point distance calculating section 8018.

(4) By using a relational table of the range of accommodation in terms of age, supposing an average range of accommodation at an assumed age, eyeball refractive values at the upper limit and the lower limit of the range of accommodation are derived. Based on them, the near point distance and the far point distance are corrected.

(5) A midpoint in the range of accommodation of the eyes of the subject is obtained from the near point distance and the far point distance. Furthermore, the approximated lens power is calculated.

(6) A start eyeball optical model is selected by the start eyeball optical model deciding section 8020 from the age and the value of the approximated lens power.

(7) The focal performance is calculated by the eyeball optical model focal performance calculating section 8022 using the selected start eyeball optical model. The ultimate eyeball optical model in an intermediate state of the accommodating function of the eyes is determined by the eyeball optical model deciding section 8028. More specifically, a light beam is directed on the eyeball optical model in the accommodation midpoint state by the eyeball optical model focal performance calculating section 8022 so as to calculate the focal performance of the light beam on a retina. The optical system design automation process is performed to achieve the best focal state. The optical dimensions are changed by the eyeball optical model deciding section 8028 to determine optimal solutions (optical dimensions). In the construction of the eyeball optical model at the accommodation midpoint, the automatic optical design calculation begins with the aforementioned start eyeball optical model to automatically determine the optical dimensions of a human eyeball so as to provide the optimal focal performance.

As used herein, the automatic optical design calculation refers to the automatic process for determining optical dimensions by light beam tracking using an automatic lens design program. As a typical example of these techniques, the dumped least squares method is available.

The calculation minimizes the sum of squares of the amount of deviation in position from the point of arrival of light on the retina while the values of the optical dimensions of the eyeball optical model are gradually varied (a radius of curvature and an intervals of surfaces are varied while a refractive index is unchanged; in the case of non-spherical surface, a radius of curvature of reference spherical surface and aspherical surface coefficient are varied) to satisfy a final performance condition (in this preferred embodiment, a focal state in which the cases where a plurality of beams of light are impinged from an infinitesimal point object located in the accommodation midpoint condition upon the pupil diameter (e.g., $\phi=3$ mm) of the eyeball optical model at various heights of incidence are calculated to track the refraction change of beams of light, thereby allowed to focus onto a point on the retina). This is the same as in an "eyeball optical model construction process of a person at the midpoint of accommodation" described below.

(8) The model validity examining section 8024 is used to check the validity of the eyeball optical model at the accommodation limit (on the near point side). In this validity check, the eyeball refractive power is increased (UP) by the amount of accommodation ability of a human eyeball, and then the automatic optical design calculation is performed to confirm a good focal performance.

As used herein, the "increasing (UP) the eyeball refractive power by the amount of accommodation ability" performs the following operations. Assuming that the far point distance is 1 m (−1.0 D) and the near point distance is 25 cm (−4.0 D), the accommodation midpoint position is 40 cm (−2.5 D) and an UP in the eyeball refractive power corresponding to the amount of correction of −1.5 D is required on the near point side with respect to the accommodation midpoint position. As described above, an increase in eyeball refractive power corresponding to this −1.5 D is provided as follows. While the boundary conditions for the automatic optical design are being controlled, a plurality of beams of light are directed from an infinitesimal point object located at a near point distance of 25 cm upon the pupil diameter (e.g., $\phi=3$ mm) of the eyeball optical model at various heights of incidence to track the beams of light. Thus, the automatic optical design is performed while the optical dimensions are being varied so as to focus the beams of light on a point on the retina.

Suppose that this has conceivably resulted in the convergence of the light on one point. In this case, it is determined that the optical model has been successfully simulated at the accommodation limit, and the eyeball optical model of the subject is valid at the accommodation midpoint.

(9) The model validity examining section 8024 checks the validity of the eyeball optical model at the accommodation limit (on the far point side). In the validity check, the eyeball refractive power is decreased (DOWN) by the amount of accommodation ability of a human eyeball, and then the automatic optical design calculation is performed to confirm good focal performance.

As used herein, the "decreasing (DOWN) the eyeball refractive power by the amount of accommodation ability" performs the following operations. Assuming that the far point distance is 1 m (−1.0 D) and the near point distance is 25 cm (−4.0 D), the accommodation midpoint position is 40 cm (−2.5 D) and a DOWN in the eyeball refractive power corresponding to the amount of correction of +1.5 D is required on the far point side with respect to the accommodation midpoint position. As described above, a decrease in eyeball refractive power corresponding to this +1.5 D is provided as follows. The boundary conditions for the automatic optical design controlled, a plurality of beams of light are directed from an infinitesimal point object located at a far point distance of 1 m upon the pupil diameter (e.g., $\phi=3$ mm) of the eyeball optical model at various heights of incidence to track the beams of light. Thus, the automatic optical design is performed while the optical dimensions are varied so as to focus the beams of light on a point on the retina.

Suppose that this has resulted in the convergence of the light on one point. In this case, it is determined that the optical model has been successfully simulated at the accommodation limit, and the eyeball optical model of the subject is valid at the accommodation midpoint.

(10) The model validity examining section 8024 checks the validity of the eyeball optical model outside the accommodation limits on the near and far point sides, i.e., outside the range of accommodation of the eyeball.

(11) The eyeball optical dimensions-accommodation range determining section 8026 finally determines the range of accommodation of the eyeball optical dimensions for the eyeball optical model at the accommodation midpoint position.

(12) An image of the decided eyeball optical model, for example, a cross-sectional view of an eyeball as shown in FIG. 74 is generated by the eyeball optical dimensions-accommodation range determining section 8026. The description for the eyeball optical model may be displayed therewith.

(13) The focal performance with the accommodation at three distances in a naked eye state of the subject is calculated by the eyeball optical model focal performance calculating section 8022.

The eyeball optical model at the accommodation midpoint position and the range of accommodation of the optical dimensions are determined as follows.

The model validity examining section 8024 performs processing for checking the validity of the eyeball optical model at the accommodation limit on the near point side and on the far point side. These checks determine, as a result of the processing for constructing an eyeball optical model of the person at the accommodation midpoint, that the eyeball optical model is valid at the accommodation midpoint position. The eyeball optical model is then used in the focal performance calculation processing, discussed later, which is accompanied by accommodation at the three distances with the eye uncorrected, and the focal performance calculation processing which is accompanied by accommodation at the three distances with the eye corrected. "The three distances" are chosen such that the viewed image is substantially changed, e.g. 0.3 m (for reading), 0.5 m −0.6 m (for deskwork), and 5 m (for car driving). The range of changes in optical dimensions at the accommodation limits (in particular, the range of changes in thickness of the lens of the eye within which the lens of the eye is made thinner or thicker, in the radius of curvature of the front surface, and in the radius of curvature of the rear surface) has also been determined by the model validity examining section 8024 performing the processing for checking the validity of the eyeball optical model at the accommodation limit. The determination of the range of changes enables simulation of the accommodation of the eye according to the distance to an object. The amount of an increase (UP) or a decrease (DOWN) in eyeball refractive power from the accommodation midpoint position is determined according to the distance to an object to perform the automatic optical design while the boundary conditions are controlled, similar to the processing of the model validity examining section 8024 for checking the validity of eyeball optical model at the accommodation limit (on the far distance side).

The optical dimensions determined as described above represent the condition of the eye in which the eyeball virtually performs focus accommodation.

The calculation is repeated until no more improvement is made in focal performance, and the resulting optical dimensions are determined as the best focal performance at the distance to the object.

To evaluate the focal performance, several hundreds of beams of light equally dispersed are directed from an infinitesimal point object located at a certain distance upon the pupil diameter (e.g., $\phi=3$ mm) of the eyeball optical model to track the beams of light, thereby calculating where the beams of light are focused on the retina. To evaluate the degree of blurring, a two-dimensional Fourier transform is performed on the intensity distribution of a point image on the retina, thereby calculating the spatial frequency characteristics (OTF) to evaluate the image.

(14) The focal performance with the accommodation at three distances described above for the optical model after vision correction with corrective lenses is calculated and examined by the eyeball optical model focal performance calculating section 8022.

That is, an actual spectacle lens (with known radii of curvature of the front and rear surfaces of the lens and a known refractive index of the glass material) is placed in front of the eyeball optical model to perform a calculation similar to the focal performance calculation processing with the eye uncorrected.

From the approximate lens power and the wearing conditions, an appropriate virtual lens is determined to perform an optical simulation on the focal performance with the spectacle/contact lens being worn.

On the other hand, when the balance between the sharpness scores at the three distances unsatisfactory, the lens power is slightly varied to perform the optical simulation again.

(15) The sharpness score generating section 8032 is used to vary the optical dimensions of the eye within the range of accommodation ability to create the condition in which the focal performance is optimally provided, calculating the sharpness score at that time. The relationship between the sharpness score and the viewed image is illustrated in FIG. 76. The sharpness score is calculated based on the results of focal condition calculated by the eyeball optical model focal performance calculating section 8022.

Several hundred beams of light equally dispersed are directed from an infinitesimal point object located at a certain distance upon the pupil diameter (e.g., $\phi=3$ mm) of the eyeball optical model to track the beams of light, thereby calculating where the beams of light are focused on the retina. A value obtained by a two-dimensional Fourier transform being performed on the intensity distribution of the point image is called the spatial frequency characteristics (OTF). Checking how the intensity is distributed on the retina enables evaluation of the degree of blurring. The spatial frequency is a value which represents the fineness of a stripe pattern and is defined as the number of stripes per unit length.

For a visual system, the spatial frequency is represented by the number of stripes per visual angle of 1 degree. For example, assuming that the spacing of the stripes is w (degrees), the spatial frequency is given that u=1/w (cycles/deg).

The value of w used for evaluating blurring is determined from the resolution of the retina, which enables the sharpness score to be calculated based on the value of u provided at that time.

(16) The viewed image generating section 8030 is then used to generate and display visual images at the three distances before and after the correction with the recommended lens (FIG. 77). By this process, the user can confirm on the screen the viewing quality with the uncorrected eye and with the recommended lens being worn.

The viewed image generating section 8030 is used to prepare images at the three distances which are photographed at high resolution. Generation of the view images is performed such that N by N size smoothing filter processing is performed on these images pixel by pixel to blur the images. The degree of blurring is adjusted by the value of N (at a minimum of 3), filter weighting, and the number of processing times. The spatial frequency analysis is performed on the images that have been filtered in order to determine the degree of blurring, which is in turn associated with the sharpness score that has been determined through the calculation of the sharpness score. Several images are prepared which correspond to the sharpness scores. Furthermore, the score values are calculated and correspond to the images obtained by the special smoothing filter processing being performed once on the prepared images.

The score value determined by the calculation of the sharpness score is used to directly display the corresponding image or to filter the displayed image corresponding to its sharpness score.

(17) Furthermore, images showing the respective views at three distances are presented for comparison by the viewed image generating section 8030 while replacing lens. More specifically, a lens power is changed to perform an optical simulation with spectacles or contact lenses on. Then, the optical dimensions are changed within the range of accommodation of the eyeball to optimize the focal performance. A sharpness score is then calculated.

If a sharpness score at a specific lens power has already been calculated by the lens power selecting section 8034, the sharpness score may be obtained using the data.

(18) The subject visually determines a corrective lens at a corrective power that he/she desires from the displayed viewed image and a sharpness score, such that the number and code of the desired corrective lens to be used is selected by the data input section 8014.

As described above, this lens power deciding system includes the input unit for inputting information related to a state of the eyes of the user, the eyeball optical model deciding unit for deciding an eyeball optical model in accordance with the information related to the input state of the eyes, the eyeball accommodation range determination unit for examining optical performance of the eyeball within the range of accommodation of the user in the decided eyeball optical model to determine the range of accommodation of the eyeball, and the lens power selecting unit for examining the optical performance when the user wears spectacles or contact lenses to select a lens power. Therefore, a lens power of spectacles or contact lenses fitted to eyes of each person is determined.

In the above description, the spectacle and contact lens selecting system, the spectacle virtual try-on system, and the remote subjective vision test system are described as independent spectacle order/sales centers, respectively. In practice, however, they are integrated on a single computer or server to share the database, or they are integrated by performing a distributed processing with a plurality of computers or servers such that the user information, the frame selection information, the vision test information, and other relevant information are intercommunicated through a LAN and other suitable network. As a result, the user accesses from a single user client to a single site to receive a series of order/sales services of spectacles or contact lenses.

The lens power may be determined by using a lens power obtained by the lens power deciding system or by using a lens power obtained by the optometry system.

Moreover, due to the spectacle and contact lens selecting system obtained by the integration of the lens power deciding function by the remote subjective vision test system, the lens power deciding system or the optometry system as described above and the frame selecting function by the above-described spectacle virtual try-on system, lenses fitted to eyes of each person can be remotely selected. In addition, frames can be selected after visual confirmation of a wearing state of each person. Therefore, the user is assured to receive the order/sales services of spectacles or contact lenses through a network such as the Internet.

Although the user client, the spectacle order/sales center and the external payment transaction agency are connected by the Internet in the above-described preferred embodiment, the present invention is not limited thereto. Alternatively, the spectacle order/sales center and the external payment transaction agency may be partially or entirely connected through a LAN or a WAN within a specific organization. Moreover, the present invention is not limited to the case where the optometry service is provided for the subject through the network. The spectacle and contact lens selecting system, according to the present invention may be installed in a store to provide the order/sales service of spectacles in a stand-alone fashion.

Although the spectacle and contact lens selecting system is described in the above-described preferred embodiments, according to the spectacle and contact lens selecting method including the respective unit in the spectacle and contact lens selecting system of the present invention as steps, the effects of the present invention can be obtained independently of a hardware configuration.

Since the method of the present invention can be achieved by a general-purpose personal computer, a computer program describing the method of the present invention in an executable manner in the personal computer may be provided for the user so as to provide a selection service of spectacles or contact lenses. It is apparent that the computer program may be provided by a recording medium such as a CD-ROM or may be provided for the user by downloading it through the Internet or other suitable network.

As described above, according to the present invention, easy selection of spectacles and contact lenses fitted to eyes of each person is ensured.

While the present invention has been described with respect to preferred embodiments, it will be apparent to those skilled in the art that the disclosed invention may be modified in numerous ways and may assume many embodiments other than those specifically set out and described above. Accordingly, it is intended by the appended claims to cover all modifications of the invention which fall within the true spirit and scope of the invention.

The invention claimed is:

1. A spectacle and contact lens selecting system comprising:
    an input unit for inputting information related to a state of eyes of a user;
    an eyeball optical model deciding unit for deciding an eyeball optical model corresponding to the information related to the state of the eyes input by the input unit;
    an eyeball accommodation range determination unit for examining optical performance of an eyeball within a range of accommodation of the user in the eyeball optical model decided by the eyeball optical model deciding unit to determine the range of accommodation of the eyeball;
    a lens power selecting unit for examining optical performance when the user wears spectacles or contact lenses so as to select a lens power; and
    a wearing state display unit for generating and displaying a wearing state of the spectacles or the contact lenses to be selected.

2. The spectacle and contact lens selecting system according to claim 1, wherein
    the input unit is configured so as to permit the user to input information regarding the eyes of the user including at least a wearing condition of the user, an age, a near point distance, a far point distance, and a vision at a constant distance.

3. The spectacle and contact lens selecting system according to claim 1, wherein
    the eyeball optical model deciding unit includes a start eyeball optical model deciding unit for deciding a start eyeball optical model based on the information of the eyes of the user including at least an age and an approximated lens power.

4. The spectacle and contact lens selecting system according to claim 1, wherein
    the eyeball optical model deciding unit is configured such that at least one of a focal state in the eyeball of the user at an accommodation midpoint calculated from a near point distance and a far point distance of the user and a focal state in the eyeball of the user in a non-accommodative state calculated from the far point distance of the user is optimized.

5. The spectacle and contact lens selecting system according to claim 1, further comprising an eyeball optical model validity examination unit for examining validity of the eyeball optical model at a limit of accommodation on at least one of a near point side and a far point side.

6. The spectacle and contact lens selecting system according to claim 1, wherein
    the eyeball accommodation range determination unit is configured to determine a range of accommodation of optical dimensions of the eyeball at an accommodation midpoint.

7. The spectacle and contact lens selecting system according to claim 1, further comprising an eyeball optical model image generating unit for generating and displaying an image of an eyeball optical model in which the range of accommodation of the eyeball is determined.

8. The spectacle and contact lens selecting system according to claim 1, further comprising an eyeball optical model focal performance examination unit for examining focal performance of the eyeball optical model at a near point or a location within a range of accommodation ability in the vicinity of the near point, at a far point or a location within the range of accommodation ability in the vicinity of the far point, or at a location away from the near point and the far point in a naked eye state of the user.

9. The spectacle and contact lens selecting system according to claim 8, wherein
the eyeball optical model focal performance examination unit includes a unit for examining a focal state of the eyeball optical model of the user at the near point or the location within the range of accommodation ability in the vicinity of the near point, at the far point or the location within the range of accommodation ability in the vicinity of the far point, or the location away from the near point and the far point after vision correction with the spectacles or the contact lenses.

10. The spectacle and contact lens selecting system according to claim 1, wherein
the spectacle and contact lens wearing state display unit includes a sharpness score generating unit for generating a sharpness score of visibility of the user at least one of before and after vision correction with the spectacles or the contact lenses.

11. The spectacle and contact lens selecting system according to claim 1, further comprising a viewed image generating unit for generating an image to be viewed by the user at least one of before and after vision correction with the spectacles or the contact lenses.

12. The spectacle and contact lens selecting system according to claim 1, wherein
the wearing state display unit includes an image acquisition unit for acquiring an image of the user, and an image synthesizing unit for synthesizing an image of spectacles or contact lenses to be selected and the acquired image of the user.

* * * * *